United States Patent
Kasina et al.

(10) Patent No.: US 9,090,633 B2
(45) Date of Patent: Jul. 28, 2015

(54) SUBSTITUTED 4-(ARYLAMINO) SELENOPHENOPYRIMIDINE COMPOUNDS AND METHODS OF USE THEREOF

(71) Applicant: KASINA LAILA INNOVA PHARMACEUTICALS PRIVATE LIMITED, Vijayawada (IN)

(72) Inventors: Sudhakar Kasina, Mercer Island, WA (US); Ganga Raju Gokaraju, Vijayawada (IN); Venkateswarlu Somepalli, Vijayawada (IN); Rama Raju Gokaraju, Vijayawada (IN); Venkata Kanaka Ranga Raju Gokaraju, Vijayawada (IN); Kiran Bhuphatiraju, Vijayawada (IN); Trimurtulu Golakoti, Vijayawada (IN); Krishanu Sengupta, Vijayawada (IN); Venkata Krishna Raju Alluri, Vijayawada (IN)

(73) Assignee: Kasina Laila Innova Pharmaceuticals Private Limited, Vijayawada (IN)

( * ) Notice: Subject to any disclaimer, the term of this patent is extended or adjusted under 35 U.S.C. 154(b) by 132 days.

(21) Appl. No.: 13/912,431

(22) Filed: Jun. 7, 2013

(65) Prior Publication Data
US 2013/0287767 A1    Oct. 31, 2013

Related U.S. Application Data

(63) Continuation-in-part of application No. PCT/IN2011/000832, filed on Dec. 7, 2011, and a continuation-in-part of application No. 13/896,538, filed on May 17, 2013, now Pat. No. 8,815,879, which is a continuation-in-part of application No. PCT/IN2011/000801, filed on Nov. 17, 2011.

(30) Foreign Application Priority Data

Nov. 18, 2010  (IN) .......................... 2468/CHE/2010
Dec. 9, 2010   (IN) .......................... 3764/CHE/2010

(51) Int. Cl.
| | |
|---|---|
| C07D 517/04 | (2006.01) |
| C07D 517/14 | (2006.01) |
| A61K 31/519 | (2006.01) |
| A61K 45/06 | (2006.01) |
| C07D 421/12 | (2006.01) |
| C07D 471/04 | (2006.01) |
| C07D 487/04 | (2006.01) |
| C07D 491/048 | (2006.01) |
| C07D 495/04 | (2006.01) |
| C07D 498/04 | (2006.01) |
| C07D 513/04 | (2006.01) |
| A61K 31/4353 | (2006.01) |

(52) U.S. Cl.
CPC .......... *C07D 517/04* (2013.01); *A61K 31/4353* (2013.01); *A61K 31/519* (2013.01); *A61K 45/06* (2013.01); *C07D 421/12* (2013.01); *C07D 471/04* (2013.01); *C07D 487/04* (2013.01); *C07D 491/048* (2013.01); *C07D 495/04* (2013.01); *C07D 498/04* (2013.01); *C07D 513/04* (2013.01); *C07D 517/14* (2013.01)

(58) Field of Classification Search
None
See application file for complete search history.

(56) References Cited

U.S. PATENT DOCUMENTS

| | | | |
|---|---|---|---|
| 6,620,804 | B2 | 9/2003 | Chang et al. |
| 6,919,338 | B2 | 7/2005 | Mortlock et al. |
| 7,417,055 | B2 | 8/2008 | Cannizzaro et al. |
| 2008/0021031 | A1 | 1/2008 | Shia et al. |
| 2009/0163494 | A1 | 6/2009 | Hong et al. |
| 2010/0004208 | A1 | 1/2010 | Chaplin et al. |
| 2010/0272678 | A1 | 10/2010 | Gokaraju et al. |
| 2013/0287767 | A1 | 10/2013 | Gokaraju et al. |

OTHER PUBLICATIONS

Gopal et al. (Journal of Photochemistry and Photobiology B: Biology 81: 181-189, 2005).*
"International Search Report issued for PCT/IN2011/000801 dated May 23, 2012".
"International Search Report issued for PCT/IN2011/000832 dated Jul. 7, 2012".
Aumann, et al., "On the stability of 2-aminoselenophene-3-carboxylates: potential dual-acting selenium-containing allosteric enhancers of A1 adenosine receptor binding", Org. Biomol. Chem., 2007,5, 1276-1281, Mar. 15, 2007.

* cited by examiner

*Primary Examiner* — Bong-Sook Baek
(74) *Attorney, Agent, or Firm* — Kramer Amado, P.C.

(57) ABSTRACT

The invention discloses 4-(arylamino)selenophenopyrimidine derivatives of formula (I), hydrates, solvates, isomers, or pharmaceutically acceptable salts thereof; process for their preparation and methods of treating or inhibiting or controlling a cell proliferative disorders, particularly cancer using said compounds. Pharmaceutical compositions comprising 4-(arylamino)selenophenopyrimidine derivatives of formula (I) are useful for the treatment, inhibition, or control of cancer.

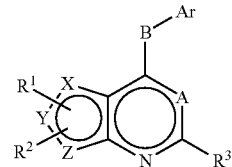

Formula I

32 Claims, No Drawings

SUBSTITUTED 4-(ARYLAMINO) SELENOPHENOPYRIMIDINE COMPOUNDS AND METHODS OF USE THEREOF

RELATED APPLICATIONS

This application is a continuation-in-part of parent International Application No. PCT/IN2011/000832, filed on Dec. 7, 2011, now published as WO 2012/077135. International Application No. PCT/IN2011/000832 claims priority to Indian Patent Application No. 3764/CHE/2010, filed on Dec. 9, 2010.

This application is also a continuation-in-part of U.S. patent application Ser. No. 13/896,538, filed on May 17, 2013, which is a continuation-in-part of International Application No. PCT/IN2011/000801, filed on Nov. 17, 2011, now published as WO 2012/066578. International Application No. PCT/IN2011/000801 claims priority to Indian Patent Application No. 3468/CHE/2010, filed on Nov. 18, 2010.

The entire disclosure of each prior application is incorporated by reference in its entirety.

FIELD OF THE DISCLOSURE

The disclosure relates to substituted 4-(arylamino)selenophenopyrimidine compounds, processes for their preparation, methods of treating or inhibiting or controlling cancer, and methods of making pharmaceutical compositions for the treatment or inhibition or control of cancer.

BACKGROUND

Cancer is a disease resulting from an abnormal growth of tissue. Certain cancers have the potential to invade into local tissues and also metastasize to distant organs. This disease can develop in a wide variety of different organs, tissues and cell types. Therefore, the term "cancer" refers to a collection of over a thousand different diseases. Over 4.4 million people worldwide were diagnosed with breast, colon, ovarian, lung, or prostate cancer and over 2.5 million people died of these devastating diseases. In the United States alone, over 1.25 million new cases and over 500,000 deaths from cancer were in 2005. The majority of these new cases will be cancers of the colon (~100,000), lung (~170,000), breast (~210,000) and prostate (~230,000). Both the incidence and prevalence of cancer is predicted to increase by approximately 15% over the next ten years, reflecting an average growth rate of 1.4%.

Cancer treatments are of two major types, either curative or palliative. The main curative therapies for cancer are surgery and radiation. These options are generally successful only if the cancer is found at an early localized stage. Once the disease has progressed to locally advanced cancer or metastatic cancer, these therapies are less effective and the goal of therapy aims at symptom palliation and maintaining good quality of life. The most prevalent treatment protocols in either treatment mode involve a combination of surgery, radiation therapy and/or chemotherapy.

Cytotoxic drugs (also known as cytoreductive agents) are used in the treatment of cancer, either as a curative treatment or with the aim of prolonging life or palliating symptoms. Cytotoxics may be combined with radiotherapy and/or surgery, as neo-adjuvant treatment (initial chemotherapy aimed at shrinking the tumor, thereby rendering local therapy such as surgery and radiation more effective) or as adjuvant chemotherapy (used in conjunction or after surgery and/or localized therapy). Combinations of different drugs are frequently more effective than single drugs: they may provide an advantage in certain tumors of enhanced response, reduced development of drug resistance and/or increased survival. It is for these reasons that the use of combined cytotoxic regimens in the treatment of many cancers is very common. Cytotoxic agents in current use employ different mechanisms to block proliferation and induce cell death. They can be generally categorized into the following groups based on their mechanism of action: the microtubule modulators that interfere with the polymerization or depolymerization of microtubules (e.g. docetaxel, paclitaxel, vinblastine, vinorelbine); anti-metabolites including nucleoside analogs and other inhibitors of key cellular metabolic pathways (e.g. capecitabine, gemcitabine, methotrexate); agents that interact directly with DNA (e.g. carboplatin, cyclophosphamide); anthracycline DNA intercalators that interfere with DNA polymerase and Topoisomerase II (e.g. doxorubicin, epirubicin); and the non-anthracycline inhibitors of Topoisomerase activity (e.g. topotecan, irinotecan, and etoposide). Even though different cytotoxic drugs act via different mechanisms of action, each generally leads to at least transient shrinkage of tumors. Cytotoxic agents continue to represent an important component in an oncologist's arsenal of weapons for use in fighting cancer. The majority of drugs currently undergoing late Phase II and Phase III clinical trials are focusing on known mechanisms of action (tubulin binding agents, anti-metabolites, DNA processing), and on incremental improvements in known drug classes (for example the taxanes or the camptothecins). A small number of cytotoxic drugs based on novel mechanisms have recently emerged. Modes of action for these cytotoxics include inhibition of enzymes involved in DNA modification (e.g. histone deacetylase (HDAC)), inhibition of proteins involved in microtubule movement and cell cycle progression (e.g. kinesins, aurora kinase), and novel inducers of the apoptotic pathway (e.g. bcl-2 inhibitors).

Even though cytotoxic agents remain in the forefront of approaches to treat patients with advanced solid tumors, their limited efficacy and narrow therapeutic indices result in significant side effects. Moreover, basic research into cancer has led to the investigation of less toxic therapies based on the specific mechanisms central to tumor progression. Such studies could lead to effective therapy with improvement of the quality of life for cancer patients. Thus, a new class of therapeutic agents has emerged, referred to as cytostatics. Cytostatics direct their action on tumor stabilization and are generally associated with a more limited and less aggravating side effect profile. Their development has resulted from the identification of specific genetic changes involved in cancer progression and an understanding of the proteins activated in cancer such as tyrosine kinases and serine/threonine kinases.

EGFR over expression occurs frequently in human epithelial malignancies and its activation plays a significant role in the development and progression of human cancers, since EGFR signaling pathways are associated with cell proliferation, survival promotion and apoptosis inhibition. Therefore, EGFR is a very attractive molecular target for cancer therapy. Over the past 20 years, numerous small molecular inhibitors and monoclonal antibodies targeting EGFR have been successfully developed. The 4-anilinoquinazolines derivatives, Iressa (Gefitinib) and Tarceva (Erlotinib (FIG. 1), are two selective EGFR inhibitors approved by the FDA in 2003 and 2004 respectively for locally advanced or metastatic non-small-cell lung cancer (NSCLC) therapy. Clinical data show that 10-20% of all NSCLC patients partially respond to these two EGFR inhibitors, but only Erlotinib prolongs the survival of patients with recurrent NSCLC. Moreover, most of the patients who responded to initial treatment eventually developed resistance to the EGFR inhibitors. Thus there is an urgent unmet medical need to design and develop new, broad therapeutic index and more potent anti-tumor active compounds.

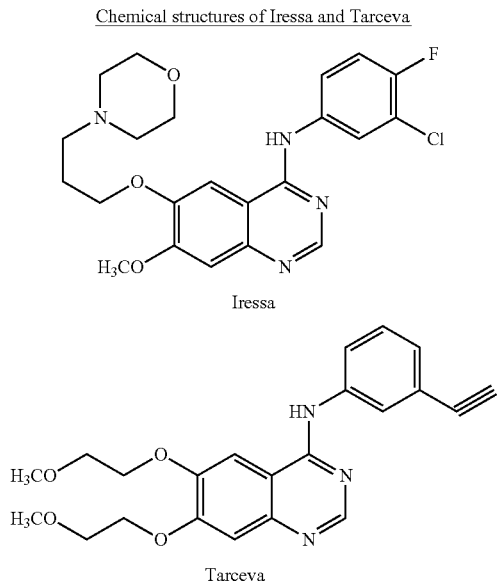

Chemical structures of Iressa and Tarceva

The technical problem to be addressed in the present disclosure may therefore be seen in providing alternative compounds having good anti-cancer activity or an inhibitory activity on EGFR tyrosine kinases or other kinases, thus offering new therapeutic options for the treatment of diseases, in particular cancer and other proliferative disorders.

SUMMARY

The present disclosure provides substituted 4-(arylamino) selenophenopyrimidine compounds of formula (I) and pharmaceutically acceptable salts thereof.

In another aspect, the disclosure provides the geometrical isomers/optical isomers/diastereomers, hydrates, solvates of the compounds of formula (I).

In another aspect, the disclosure provides a process for preparing the compounds of formula (I).

In another aspect, the disclosure provides pharmaceutical compositions comprising atleast one 4-(arylamino)selenophenopyrimidine compound selected from the above formula (I) and derivatives thereof, in combination with atleast one pharmaceutically acceptable excipient/carrier/diluents.

In another aspect, the disclosure provides pharmaceutical compositions comprising atleast one 4-(arylamino)selenophenopyrimidine compound selected from the above formula (I) and derivatives thereof, in combination with atleast one pharmaceutically acceptable excipient/carrier/diluents and optionally atleast one anti-tumor agent.

In another aspect, the present disclosure provides a method of treating or inhibiting or controlling a cell proliferative disorder, particularly cancer in a patient in need of such treatment, comprising administering to the patient an effective amount of a compound of formula (I) or their compositions as defined above.

Various embodiments disclosed herein relate to selenophene compounds of formula (I):

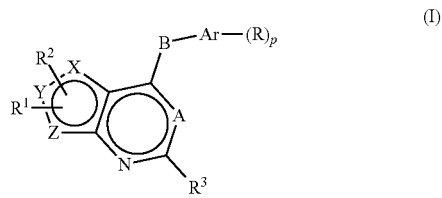

wherein X, Y, and Z are independently selected from the group consisting of selenium and carbon, with the proviso that one of X, Y, and Z is selenium;

A is N or C—$R^4$, wherein $R^4$ is selected from the group consisting of hydrogen, halogen, hydroxy, formyl, carboxylic acid, amino, nitro, cyano, sulfonic acid, thiole, trihalomethyl, sulfonamide, $C_{1-6}$alkyl, $C_{1-6}$ secondary alkyl, $C_{1-6}$ tertiary alkyl, $C_{2-6}$ alkenyl, $C_{2-6}$alkynyl, $C_{1-4}$alkylcarbonyl, $C_{1-4}$alkoxycarbonyl, aminocarbonyl, $C_{1-6}$ alkylaminocarbonyl, di($C_{1-6}$ alkyl)aminocarbonyl, $C_{1-6}$haloalkyl, $C_{1-6}$ hydroxyalkyl, $C_{1-6}$ alkoxy, $C_{1-6}$haloalkoxy, $C_{1-6}$ hydroxyalkoxy, $C_{3-7}$cycloalkyl, $C_{3-7}$cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, and $C_{1-6}$ alkylsulfonyl;

B is selected from the group consisting of S, S(O), S(O)$_2$ and NR$^5$; wherein R$^5$ is selected from the group consisting of hydrogen, alkyl, alkoxy and haloalkyl; and Ar is selected from the group consisting of an optionally substituted benzene ring, an optionally substituted napththalene ring; an optionally substituted 6-membered aromatic ring containing one, two or three nitrogen atoms; and an optionally substituted 5-membered aromatic ring containing at least one heteroatom selected from the group consisting of sulfur, oxygen, selenium, and nitrogen, with the proviso that said 5-membered aromatic ring contains no more than one oxygen, sulfur, or selenium atom. In various embodiments of the compounds of formula (I), A is N and B is NR$^5$.

In various embodiments of the compounds of formula (I), p is 0, 1, 2, 3, 4, or 5; and R, $R^1$, $R^2$, and $R^3$ are independently selected from the group consisting of hydrogen, halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$alkenyl, $C_{2-6}$alkynyl, $C_{1-4}$ alkyl carbonyl, $C_{1-4}$ alkoxycarbonyl, aminocarbonyl, $C_{1-6}$ alkylaminocarbonyl, di($C_{1-6}$ alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$cycloalkyl, $C_{3-7}$cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$ alkyl)amino]alkyl, $C_{1-6}$ alkylsulfinyl, $C_{1-6}$ alkylsulfonyl, an optionally substituted aryl ring, an optionally substituted heteroaryl ring, and an optionally substituted heterocycloalkyl ring. In certain embodiments, $R^1$ and $R^2$ may additionally be selected from the group consisting of a group having the formula:

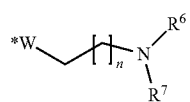

wherein n is 0, 1, 2, 3, 4, or 5; * indicates the point of attachment to the selenophene ring in formula I; W is selected from the group consisting of $CH_2$, O, S, or NH; and $R^6$ and $R^7$ are independently selected from the group consisting of hydrogen, amino, trihalomethyl, $C_{1-6}$ alkyl, $C_{1-6}$ secondary alkyl, $C_{1-6}$ tertiary alkyl, $C_{2-6}$ alkenyl, $C_{2-6}$ alkynyl, $C_{1-4}$ alkylcarbonyl, $C_{1-4}$ alkoxycarbonyl, aminocarbonyl, $C_{1-6}$ alkylaminocarbonyl, di($C_{1-6}$ alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$ cycloalkyl, $C_{3-7}$ cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ [($C_{1-6}$ alkylamino)alkyl, $C_{1-6}$ [di($C_{1-6}$ alkyl)amino]alkyl.

In some embodiments of the compounds of formula (I), $R^1$ and $R^2$ may be joined to form a group having the formula:

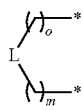

wherein m and o are independently 0, 1, 2, 3 or 4; * indicates the point of attachment to the selenophene ring in formula I; L is selected from the group consisting of $CH_2$, O, S and $NR^8$; and $R^8$ is selected from the group consisting of hydrogen, amino, trihalomethyl, $C_{1-6}$ alkyl, $C_{1-6}$ secondary alkyl, $C_{1-6}$ tertiary alkyl, $C_{2-6}$ alkenyl, $C_{2-6}$ alkynyl, $C_{1-4}$ alkylcarbonyl, $C_{1-4}$ alkoxycarbonyl, aminocarbonyl, $C_{1-6}$ alkylaminocarbonyl, di($C_{1-6}$ alkyl) aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$ cycloalkyl, $C_{3-7}$ cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$ alkyl)amino]alkyl, and a group of the formula:

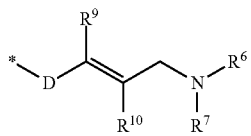

wherein * indicates the point of attachment to N in $NR^8$; D is selected from the group consisting of $C_{1-6}$ alkyl, C(O), S(O), and $S(O)_2$; and $R^9$ and $R^{10}$ are selected from the group consisting of hydrogen, halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$ alkenyl, $C_{2-6}$ alkynyl, $C_{1-4}$ alkylcarbonyl, $C_{1-4}$ alkoxycarbonyl, aminocarbonyl, $C_{1-6}$ alkylaminocarbonyl, di($C_{1-6}$ alkyl) aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$ cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$ alkyl)amino]alkyl, $C_{1-6}$ alkylsulfinyl, and $C_{1-6}$ alkylsulfonyl; and $R^6$ and $R^7$ are joined, and taken together with the atom to which they are attached, form a 5- to 7-membered optionally substituted cycloalkyl or cycloheteroalkyl ring.

In further embodiments of the compounds of formula (I), $R^1$ and $R^2$ are joined, and taken together with the atoms to which they are attached, form an optionally substituted aryl ring, an optionally substituted 6-membered aromatic ring containing one, two or three nitrogen atoms; or an optionally substituted 5-membered aromatic ring containing one or more heteroatoms selected from the group consisting of sulfur, oxygen, and nitrogen, with the proviso that no more than one oxygen or sulfur atom is present.

In various embodiments of the selenophene compound of formula (I), X is selenium and both Y and Z are carbon; Y is selenium and both X and Z are carbon; or Z is selenium and both X and Y are carbon.

Various embodiments disclosed herein relate to a process for the preparation of selenophene compounds of formula (I). In certain embodiments, selenophene compounds of formula (I) are prepared by reacting a compound of formula II or a derivative thereof with formic acid and sulfuric acid to obtain a compound of formula III;

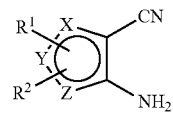
Formula II

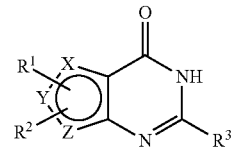
Formula III

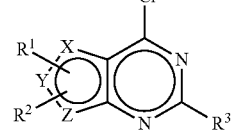
Formula IV reacting the compound of formula III with a chlorinating agent in the presence of DMF or a base to obtain a compound of formula IV; and reacting the compound of formula IV with an unsubstituted or substituted aromatic amino compound in the presence of a solvent and optionally in the presence of a base to obtain a compound of formula I.

In other embodiments, selenophene compounds of formula (I) are prepared by reacting a compound of formula II with dimethylformamide-dimethylacetal (DMF-DMA) in the presence of a solvent to obtain a compound of formula V; and

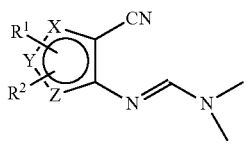
Formula V reacting the compound of formula V with an unsubstituted or substituted aromatic amino compound to obtain a compound of formula I.

In further embodiments, selenophene compounds of formula (I) are prepared by reacting a compound of formula II with a trialkyl orthoformate in the presence of a solvent to obtain a compound of formula VI, where $R^{11}$ is alkyl; and

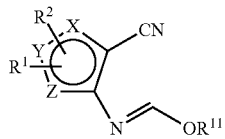

Formula VI reacting the compound of formula VI with an unsubstituted or substituted aromatic amino compound to obtain a compound of formula I.

Various embodiments disclosed herein relate to selenophene compounds of formula (VII):

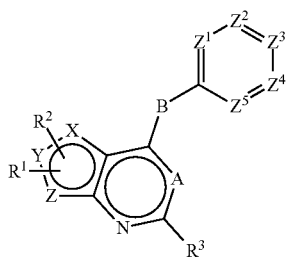

VII wherein A, B, X, Y, Z, $R^1$, $R^2$, and $R^3$ are as defined above with reference to formula (I); and $Z^1$, $Z^2$, $Z^3$, $Z^4$, and $Z^5$ are independently selected from the group consisting of N and C—$R^{11}$, wherein each $R^{11}$ is independently selected from the group consisting of hydrogen, halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$ alkenyl, $C_{2-6}$alkynyl, $C_{1-4}$ alkyl carbonyl, $C_{1-4}$ alkoxycarbonyl, aminocarbonyl, $C_{1-6}$ alkylaminocarbonyl, di($C_{1-6}$alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$ cycloalkyl, $C_{3-7}$ cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, $C_{1-6}$ alkylsulfonyl, optionally substituted phenyl ring, optionally substituted benzyl, and an optionally substituted five membered heteroaromatic ring containing one or more heteroatoms selected from sulfur, oxygen, nitrogen and selenium, with the proviso that no more than one oxygen or sulfur or selenium atom is present in said optionally substituted five membered heteroaromatic ring;

wherein said phenyl ring, said benzyl, and said 5-membered heteroaromatic ring are optionally substituted by halogen, hydroxy, formyl, carboxylic acid, amino, nitro, cyano, sulfonic acid, thiol, trihalomethyl, sulfonamide, $C_{1-6}$alkyl, $C_{1-6}$ secondary alkyl, $C_{1-6}$ tertiary alkyl, $C_{2-6}$alkenyl, $C_{2-6}$alkynyl, $C_{1-4}$ alkyl carbonyl, $C_{1-4}$ alkoxycarbonyl, aminocarbonyl, $C_{1-6}$ alkylaminocarbonyl, di($C_{1-6}$alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$ cycloalkyl, $C_{3-7}$ cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, $C_{1-6}$ alkylsulfonyl.

In various embodiments, $Z^1$, $Z^2$, $Z^3$, $Z^4$, and $Z^5$ in selenophene compounds of formula (VII) define a benzene, pyridine, pyrazine, pyrimidine, pyridazine, or triazine ring. In certain embodiments disclosed herein, $Z^1$, $Z^2$, $Z^3$, $Z^4$, and $Z^5$ are each C—$R^{11}$, i.e., $Z^1$, $Z^2$, $Z^3$, $Z^4$, and $Z^5$ define a benzene ring.

In some embodiments, $Z^1$, $Z^2$, $Z^3$, $Z^4$, and $Z^5$ are independently selected from the group consisting of N and C—$R^{11}$, with the proviso that one of $Z^1$, $Z^2$, $Z^3$, $Z^4$, and $Z^5$ is N, i.e., $Z^1$, $Z^2$, $Z^3$, $Z^4$, and $Z^5$ define a pyridine ring. In other compounds, $Z^1$, $Z^2$, $Z^3$, $Z^4$, and $Z^5$ are independently selected from the group consisting of N and C—$R^{11}$, with the proviso that $Z^1$ and $Z^2$ are each N; or $Z^2$ and $Z^3$ are each N; i.e., $Z^1$, $Z^2$, $Z^3$, $Z^4$, and $Z^5$ define a pyridazine ring.

In some embodiments, $Z^1$, $Z^2$, $Z^3$, $Z^4$, and $Z^5$ are independently selected from the group consisting of N and C—$R^{11}$, with the proviso that $Z^1$ and $Z^3$ are each N, $Z^1$ and $Z^5$ are each N, or $Z^2$ and $Z^4$ are each N; i.e., $Z^1$, $Z^2$, $Z^3$, $Z^4$, and $Z^5$ define a pyrimidine ring. In some cases, $Z^1$, $Z^2$, $Z^3$, $Z^4$, and $Z^5$ are independently selected from the group consisting of N and C—$R^{11}$, with the proviso that $Z^1$ and $Z^4$ are each N; i.e., $Z^1$, $Z^2$, $Z^3$, $Z^4$, and $Z^5$ define a pyrazine ring.

Various embodiments disclosed herein relate to selenophene compounds of formula (VIII):

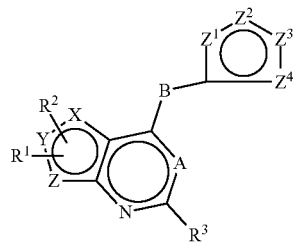

VIII wherein $Z^1$, $Z^2$, $Z^3$, and $Z^4$ are independently selected from the group consisting of S, O, N, NH, and C—$R^{11}$, with the proviso that at least one of $Z^1$, $Z^2$, $Z^3$, and $Z^4$ is not C—$R^{11}$, and no more than one of $Z^1$, $Z^2$, $Z^3$, and $Z^4$ is O or S;

wherein each $R^{11}$ is independently selected from the group consisting of hydrogen, halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$ alkenyl, $C_{2-6}$alkynyl, $C_{1-4}$ alkyl carbonyl, $C_{1-4}$ alkoxycarbonyl, aminocarbonyl, $C_{1-6}$ alkylaminocarbonyl, di($C_{1-6}$alkyl)aminocarbonyl, $C_{1-6}$ haloalkyl, $C_{1-6}$ hydroxyalkyl, $C_{1-6}$ alkoxy, $C_{1-6}$haloalkoxy, $C_{1-6}$ hydroxyalkoxy, $C_{3-7}$cycloalkyl, $C_{3-7}$cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, $C_{1-6}$ alkylsulfonyl, optionally substituted phenyl ring, optionally substituted benzyl, and an optionally substituted five membered heteroaromatic ring containing one or more heteroatoms selected from sulfur, oxygen, nitrogen and selenium, with the proviso that no more than one oxygen or sulfur or selenium atom is present in said optionally substituted five membered heteroaromatic ring;

wherein said phenyl ring, said benzyl, and said 5-membered heteroaromatic ring are optionally substituted by halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$alkenyl, $C_{2-6}$alkynyl, $C_{1-4}$ alkyl carbonyl, $C_{1-4}$ alkoxycarbonyl, aminocarbonyl, $C_{1-6}$ alkylaminocarbonyl, di($C_{1-6}$alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$cycloalkyl, $C_{3-7}$ cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, $C_{1-6}$ alkylsulfonyl.

Various embodiments disclosed herein relate to selenophene compounds of formula (VIII), wherein $Z^1$, $Z^2$, $Z^3$, and $Z^4$ define a thiophene, furan, pyrrole, oxazole, isoxazole, imidazole, pyrazole, thiazole, or isothiazole ring. Various embodiments disclosed herein relate to compounds of formula (VIII), wherein $Z^1$, $Z^2$, $Z^3$, and $Z^4$ are independently selected from the group consisting of S and C—$R^{11}$, with the proviso that one of $Z^1$, $Z^2$, $Z^3$, and $Z^4$ is S; i.e., $Z^1$, $Z^2$, $Z^3$, and $Z^4$ define a thiophene ring. In some compounds of formula (VIII), $Z^1$, $Z^2$, $Z^3$, and $Z^4$ are independently selected from the group consisting of O and C—$R^{11}$, with the proviso that one of $Z^1$, $Z^2$, $Z^3$, and $Z^4$ is O; i.e., $Z^1$, $Z^2$, $Z^3$, and $Z^4$ define a furan ring. In other compounds of formula (VIII), $Z^1$, $Z^2$, $Z^3$, and $Z^4$ are independently selected from the group consisting of NH and C—$R^{11}$, with the proviso that one of $Z^1$, $Z^2$, $Z^3$, and $Z^4$ is NH; i.e., $Z^1$, $Z^2$, $Z^3$, and $Z^4$ define a pyrrole ring.

In various embodiments of compounds of formula (VIII), $Z^1$, $Z^2$, $Z^3$, and $Z^4$ are independently selected from the group consisting of N, NH and C—$R^{11}$, with the proviso that the optionally substituted 5-membered aromatic ring contains a N—NH bond; i.e., $Z^1$, $Z^2$, $Z^3$, and $Z^4$ define a pyrazole ring. In other embodiments of compounds of formula (VIII), $Z^1$, $Z^2$, $Z^3$, and $Z^4$ are independently selected from the group consisting of N, NH and C—$R^{11}$, with the proviso that $Z^1$ is N, and either $Z^3$ or $Z^4$ is NH; i.e., $Z^1$, $Z^2$, $Z^3$, and $Z^4$ define an imidazole ring.

In various compounds of formula (VIII), $Z^1$, $Z^2$, $Z^3$, and $Z^4$ are independently selected from the group consisting of N, O, and C—$R^{11}$, with the proviso that either $Z^1$ is N, and either $Z^3$ or $Z^4$ is O; or $Z^1$ is O, and either $Z^3$ or $Z^4$ is N; i.e., $Z^1$, $Z^2$, $Z^3$, and $Z^4$ define an oxazole ring. In other compounds of formula (VIII), $Z^1$, $Z^2$, $Z^3$, and $Z^4$ are independently selected from the group consisting of N, O, and C—$R^{11}$, with the proviso that either $Z^1$ is N and $Z^2$ is O; $Z^1$ is O and $Z^2$ is N; or $Z^2$ is N and $Z^3$ is O; i.e., $Z^1$, $Z^2$, $Z^3$, and $Z^4$ define an isoxazole ring.

In various compounds of formula (VIII), $Z^1$, $Z^2$, $Z^3$, and $Z^4$ are independently selected from the group consisting of N, S, and C—$R^{11}$, with the proviso that $Z^1$ is N, and either $Z^3$ or $Z^4$ is S; or $Z^1$ is S, and either $Z^3$ or $Z^4$ is N; i.e., $Z^1$, $Z^2$, $Z^3$, and $Z^4$ define a thiazole ring. In other compounds of formula (VIII), $Z^1$, $Z^2$, $Z^3$, and $Z^4$ are independently selected from the group consisting of N, S, and C—$R^{11}$, with the proviso that either $Z^1$ is N and $Z^2$ is S; or $Z^1$ is S and $Z^2$ is N; or $Z^2$ is N and $Z^3$ is S; i.e., $Z^1$, $Z^2$, $Z^3$, and $Z^4$ define an isothiazole ring.

The present disclosure also relates to compounds of formula (IX) and pharmaceutically acceptable salts thereof:

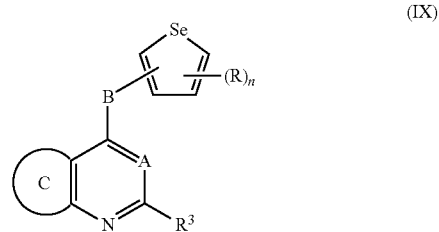

(IX)

wherein:
ring C is a 5-membered heteroaromatic fused ring containing at least one heteroatom selected from the group consisting of sulfur, oxygen, nitrogen and selenium, with the proviso that no more than one oxygen or sulfur or selenium atom is present; or a mono- or bicyclic saturated heterocyclic fused ring having 3 to 10 carbon atoms and at least one ring member selected from the group consisting of N, O, S, SO and $SO_2$;
wherein ring C is optionally substituted by at least one group independently selected from the group consisting of hydrogen, halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$alkenyl, $C_{2-6}$ alkynyl, $C_{1-4}$alkyl carbonyl, $C_{1-4}$alkoxycarbonyl, aminocarbonyl, $C_{1-6}$ alkylaminocarbonyl, di($C_{1-6}$alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$cycloalkyl, $C_{3-7}$ cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino) alkyl, $C_{1-6}$ [di($C_{1-6}$alkyl)amino]alkyl, $C_{1-6}$ alkylsulfinyl, $C_{1-6}$ alkylsulfonyl, and a aryl, heteroaryl or heterocycloalkyl ring; said aryl, heteroaryl and heterocycloalkyl ring being optionally substituted by halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$alkenyl, $C_{2-6}$alkynyl, $C_{1-4}$alkyl carbonyl, $C_{1-4}$alkoxycarbonyl, aminocarbonyl, $C_{1-6}$alkylaminocarbonyl, di($C_{1-6}$alkyl) aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$cycloalkyl, $C_{3-7}$cycloalkoxy, $C_{1-6}$alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, $C_{1-6}$ alkylsulfonyl; and
A, B, R, and $R^3$ in formula IX are the same as A, B, R, and $R^3$ in formula I.

Various embodiments disclosed herein provide a process for preparing the compounds of formula (IX), further described in International Application No. PCT/IN2011/000801, filed on Nov. 17, 2011, now published as WO 2012/066578 and incorporated herein by reference. In certain embodiments, a selenophene compound of formula (IX) or a salt thereof is prepared by reacting a compound of formula X with a compound of formula XI in the presence of a solvent and optionally in the presence of a base selected from the group consisting of organic and inorganic bases. In various embodiments, A and $R^3$ in formula X are the same as A and $R^3$ in formula I, and ring C in formula X is a fused thiophene, furan, pyrrole, selenophene, oxazole, isoxazole, imidazole, pyrazole, thiazole, or isothiazole ring. In various embodiments, B and R in formula XI are the same as B and R in formula I.

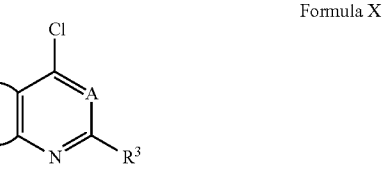

Formula X

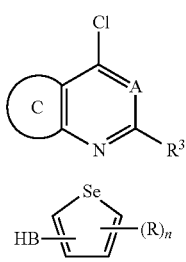

Formula XI

Further methods of manufacturing a compound of formula IX are disclosed in International Application No. PCT/IN2011/000801, filed on Nov. 17, 2011, now published as WO 2012/066578 and incorporated herein by reference.

DETAILED DESCRIPTION OF VARIOUS EMBODIMENTS

Various exemplary embodiments will now be described in detail, so that various aspects of the disclosure may be more fully understood and appreciated.

The present disclosure describes pharmaceutical compounds which are analogs of 4-(phenylamino)quinazoline. These compounds utilize selenophene as a backbone moiety instead of a benzene ring, to significantly increase activity of the analogs for possible cure in the early stage diagnosis, and significantly increase efficacy in the treatment of, late stage cancer. The reason that the selenophene ring system was chosen in place of an aromatic phenyl ring system is because selenium being larger atom in a five membered ring could resemble phenyl ring in the shape and size and attain phenyl ring structure in space. The receptors involved in recognizing the 4-(phenylamino)quinazoline for example in gefitinib can also be recognized by the 4-(arylamino)selenophenopyrimidine for biological response. In addition, selenium as an organometallic compound has anticancer properties. Selenium is a well-recognized essential trace element in human, with doses of 55-90 µg required to maintain a healthy diet in humans (Aumann, K. M.; Scammells, P. J.; White, J. M.; Schiesser, C. H. Org. Biomol. Chem., 2007, 5, 1276-1281). The selenium therefore, can be incorporated as an organometallic compound via aromatic selenophene ring system replaced for an aromatic phenyl system with significantly increased efficacy.

The proposed novel analogs will attain conformation that fits to the receptors on the tumor cell membrane in a Specific Conformational Perturbation (SCP) to afford physiological response. With this new designs all the molecules in a prearranged specific conformation will bind to the receptors one hundred percent of the time, while the drug in the market Iressa may be due to its Non Specific Conformational Perturbation (NSCP) will have relatively low probability of binding hundred percent of the time leading to no physiological response and hence decreased activity.

This would in turn afford high specificity with a larger window of the Therapeutic Index (TI). In general, for the treatment of cancer patients, a larger therapeutic index is preferred. This is because; one would like to start the therapeutic regimen with a very high Maximum Tolerated Dose (MTD) such that the cancer cells would be hit hard in the first chemotherapy itself. Otherwise, the surviving cancer cells would repair the DNA damage and subsequently metastasize to the other organs. In addition, the cancer cells that survived from the first treatment would become resistant to the second chemotherapy, again, if needed. And besides, due to weakness of the immune system from the first chemotherapy, a suboptimal dose would be given in the second treatment that would contribute to toxicity.

As a part of developing novel anti-cancer compounds, several 4-(arylamino)selenophenopyrimidine compounds of general formula (I) have been prepared and tested for their efficacy against different cancer cell lines. It was found that these 4-(arylamino)selenophenopyrimidine compounds of the general formula (I) showed good inhibition in cell proliferation of human carcinoma cells such as lung carcinoma A549 cells, colorectal carcinoma HT29 cells, prostate DU145 cells, breast carcinoma (estrogen receptor negative) MDA-MB-231 cells, hepatocellular carcinoma HepG2 cells and cervical carcinoma HeLa cells in vitro. Surprisingly, the inventors found that in comparison with gefitinib (Iressa), 4-(arylamino)selenophenopyrimidine analog (compound 33) of general formula (I) showed better efficacies in inhibiting cell proliferation of different human tumor cells in vitro (Table 1 & 2). The IC50 values of the compound 33 are 28.38, 29.47, 13.11, 20.45, 10.41 and 23.09 µM on A549, DU145, HT29, MDA-MB-231, HepG2 and HeLa cells, respectively. In contrast, the IC50 values of Gefitinib (Iressa) are 57.1, 31.47, 46.9, 45.40, 35.53, and 50.12 µM on A549, DU145, HT29, MDA-MB-231, HepG2 and HeLa cells, respectively. The observations suggest that the compound 33 is 101%, 6.8%, 257.8%, 122%, 241%, 117% more potent than Gefitinib (Iressa) in inhibiting A549, DU145, HT29, MDA-MB-231, HepG2 and HeLa tumor cells proliferation, respectively in vitro. Hence, the novel analog (Compound 33) is significantly better than the marketed drug gefitinib (Iressa), in terms of its in vitro efficacy and the results are summarized in Tables 1 & 2.

Even though various selected compounds have been used as exemplary embodiments, the invention encompasses all compounds of the formula (I) and their derivatives.

Accordingly, the disclosure provides substituted 4-(arylamino)selenophenopyrimidine compounds represented by the following formula (I) and pharmaceutically acceptable salts thereof;

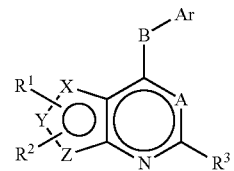

Formula (I)

wherein

X is selenium, Y and Z are carbons; or

Y is selenium, X and Z are carbons; or

Z is selenium, X and Y are carbons;

A is N or C—$R^4$, wherein $R^4$ is selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy-$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino-$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl;

B is selected from S, S(O), S(O$_2$) or NR$^5$; wherein R$^5$ is selected from hydrogen, alkyl, alkoxy or haloalkyl;

Ar is aryl or heteroaryl ring; the aryl is benzene ring or napththalene ring and heteroaryl is 6-membered aromatic ring containing one, two or three nitrogen atoms; or the heteroaryl is 5-membered aromatic ring containing one or more heteroatoms selected from sulfur, oxygen, and nitrogen, with proviso that no more than one oxygen or sulfur atom is present; such rings include pyridine, pyridazine, pyrazine, pyrimidine, thiophene, furan, pyrrole, pyrazole, imidazole, oxazole, isoxazole, thiazole and isothiazole;

Ar ring is optionally substituted by one, two or more groups independently selected from hydrogen, halogen, hydroxy, formyl, carboxylic acid, amino, nitro, cyano, sulfonic acid, thiole, trihalomethyl, sulfonamide, C$_{1-6}$alkyl, C$_{1-6}$secondaryalkyl, C$_{1-6}$tertiaryalkyl, C$_{2-6}$alkenyl, C$_{2-6}$alkynyl, C$_{1-4}$alkylcarbonyl, C$_{1-4}$alkoxycarbonyl, aminocarbonyl, C$_{1-6}$alkylaminocarbonyl, di(C$_{1-6}$alkyl)aminocarbonyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{1-6}$alkylamino, di(C$_{1-6}$alkyl)amino, aminoC$_{1-6}$alkyl, amino-C$_{1-6}$alkoxy, C$_{1-6}$alkylamino C$_{1-6}$alkyl, di(C$_{1-6}$alkyl)aminoC$_{1-6}$alkyl, C$_{1-6}$alkylsulfinyl, C$_{1-6}$alkylsulfonyl, and a aryl, heteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, C$_{1-6}$alkyl, C$_{2-6}$alkenyl, C$_{2-6}$alkynyl, C$_{1-4}$alkylcarbonyl, C$_{1-4}$alkoxy-carbonyl, aminocarbonyl, C$_{1-6}$alkylaminocarbonyl, di(C$_{1-6}$alkyl)aminocarbonyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{1-6}$alkylamino, di(C$_{1-6}$alkyl)amino, amino-C$_{1-6}$alkyl, aminoC$_{1-6}$alkoxy, C$_{1-6}$alkylaminoC$_{1-6}$alkyl, di(C$_{1-6}$alkyl)aminoC$_{1-6}$alkyl, C$_{1-6}$alkylsulfinyl, C$_{1-6}$alkylsulfonyl;

R$^1$, R$^2$, and R$^3$ are independently selected from hydrogen, halogen, hydroxy, formyl, carboxylic acid, amino, nitro, cyano, sulfonic acid, thiole, trihalomethyl, sulfonamide, C$_{1-6}$alkyl, C$_{1-6}$secondaryalkyl, C$_{1-6}$tertiaryalkyl, C$_{2-6}$alkenyl, C$_{2-6}$alkynyl, C$_{1-4}$alkyl-carbonyl, C$_{1-4}$alkoxycarbonyl, aminocarbonyl, C$_{1-6}$alkylaminocarbonyl, di(C$_{1-6}$alkyl)aminocarbonyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{1-6}$alkylamino, di(C$_{1-6}$alkyl)amino, aminoC$_{1-6}$alkyl, aminoC$_{1-6}$alkoxy, C$_{1-6}$alkylamino C$_{1-6}$alkyl, di(C$_{1-6}$alkyl)aminoC$_{1-6}$alkyl, C$_{1-6}$alkylsulfinyl, C$_{1-6}$alkylsulfonyl, and a aryl, heteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, C$_{1-6}$alkyl, C$_{2-6}$alkenyl, C$_{2-6}$alkynyl, C$_{1-4}$alkylcarbonyl, C$_{1-4}$alkoxycarbonyl, aminocarbonyl, C$_{1-6}$alkyl-aminocarbonyl, di(C$_{1-6}$alkyl)aminocarbonyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{1-6}$alkylamino, di(C$_{1-6}$alkyl)amino, aminoC$_{1-6}$alkyl, aminoC$_{1-6}$alkoxy, C$_{1-6}$alkyl-aminoC$_{1-6}$alkyl, di(C$_{1-6}$alkyl)amino C$_{1-6}$alkyl, C$_{1-6}$alkylsulfinyl, C$_{1-6}$alkylsulfonyl; or R$^1$, and R$^2$ is independently selected from the following formula;

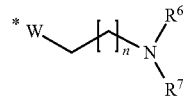

wherein n is an integer selected from 0, 1 to 5; preferably 2; * indicates the point of attachment to the selenophene ring in formula I; W is selected from CH$_2$, O, S, or NH; R$^6$ and R$^7$ is independently selected from hydrogen, amino, trihalomethyl, C$_{1-6}$alkyl, C$_{1-6}$secondaryalkyl, C$_{1-6}$tertiaryalkyl, C$_{2-6}$alkenyl, C$_{2-6}$alkynyl, C$_{1-4}$alkylcarbonyl, C$_{1-4}$alkoxycarbonyl, aminocarbonyl, C$_{1-6}$alkylaminocarbonyl, di(C$_{1-6}$alkyl)aminocarbonyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{1-6}$alkylamino, di(C$_{1-6}$alkyl)amino, aminoC$_{1-6}$alkyl, aminoC$_{1-6}$alkoxy, C$_{1-6}$alkylamino C$_{1-6}$alkyl, di(C$_{1-6}$alkyl)aminoC$_{1-6}$alkyl; or R$^1$ and R$^2$ are joined, and taken together with the atoms to which they are attached, form a 5- to 7-membered optionally substituted carbocyclic or perhydroheterocyclic ring and are selected from the formula;

wherein n is an integer selected from 0 to 4; m is an integer selected from 0 to 4; * indicates the point of attachment to the R$^1$ and R$^2$ in formula I; L is selected from CH$_2$, O, S and NR$^8$; where in R$^8$ is selected from hydrogen, amino, trihalomethyl, C$_{1-6}$alkyl, C$_{1-6}$secondaryalkyl, C$_{1-6}$tertiaryalkyl, C$_{2-6}$alkenyl, C$_{2-6}$alkynyl, C$_{1-4}$alkylcarbonyl, C$_{1-4}$alkoxycarbonyl, aminocarbonyl, C$_{1-6}$alkylaminocarbonyl, di(C$_{1-6}$alkyl)aminocarbonyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{1-6}$alkylamino, di(C$_{1-6}$alkyl)amino, aminoC$_{1-6}$alkyl, aminoC$_{1-6}$alkoxy, C$_{1-6}$alkylamino C$_{1-6}$alkyl, di(C$_{1-6}$alkyl)aminoC$_{1-6}$alkyl;

or R$^8$ is selected from the following formula;

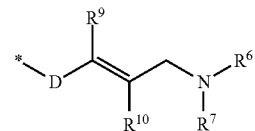

* indicates the point of attachment to N in NR$^8$; wherein D is selected from C$_{1-6}$alkyl, —C(=O), —S(=O), —S(=O)$_2$; R$^9$ and R$^{10}$ is selected from hydrogen, halogen, hydroxy, formyl, carboxylic acid, amino, nitro, cyano, sulfonic acid, thiole, trihalomethyl, sulfonamide, C$_{1-6}$alkyl, C$_{1-6}$secondaryalkyl, C$_{1-6}$tertiaryalkyl, C$_{2-6}$alkenyl, C$_{2-6}$alkynyl, C$_{1-4}$alkylcarbonyl, $C_{1-4}$alkoxycarbonyl, aminocarbonyl, $C_{1-6}$alkyl-aminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkyl-amino $C_{1-6}$alkyl, di($C_{1-6}$alkyl)amino$C_{1-6}$alkyl, $C_{1-6}$alkylsulfinyl, $C_{1-6}$alkylsulfonyl; or $R^6$ and $R^7$ are joined, and taken together with the atoms to which they are attached, form a 5- to 7-membered optionally substituted cycloalkyl or cycloheteroalkyl ring; or $R^1$ and $R^2$ are joined, and taken together with the atoms to which they are attached, form optionally substituted aryl or optionally substituted heteroaryl ring fused with selenophene; aryl is benzene ring and heteroaryl is 6-membered aromatic ring containing one, two or three nitrogen atoms; or the heteroaryl is 5-membered aromatic ring containing one or more heteroatoms selected from sulfur, oxygen, and nitrogen, with proviso that no more than one oxygen or sulfur atom is present; such rings include pyridine, pyridazine, pyrazine, pyrimidine, thiophene, furan, pyrrole, pyrazole, imidazole, oxazole, isoxazole, thiazole and isothiazole.

In certain embodiments, the disclosure provides substituted 4-(arylamino)selenophenopyrimidine compounds represented by the following formula (I),

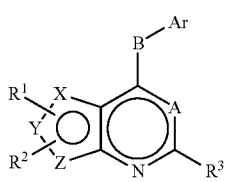

Formula (I)

wherein
X is selenium, when Y and Z are carbons; or
Y is selenium, when X and Z are carbons; or
Z is selenium, when X and Y are carbons; and is selected from the following;

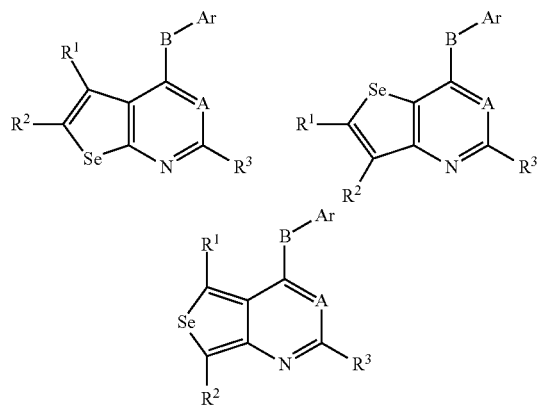

In another embodiment, the disclosure provides substituted 4-(arylamino)selenophenopyrimidine compounds represented by the formula (I), wherein A is N; B is $NR^5$ and Ar is aryl or heteroaryl ring; aryl ring is substituted or unsubstituted benzene as shown below;

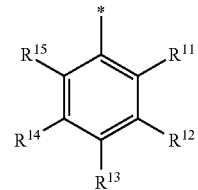

wherein
indicates the point of attachment to B of formula (I) and is selected from the following;

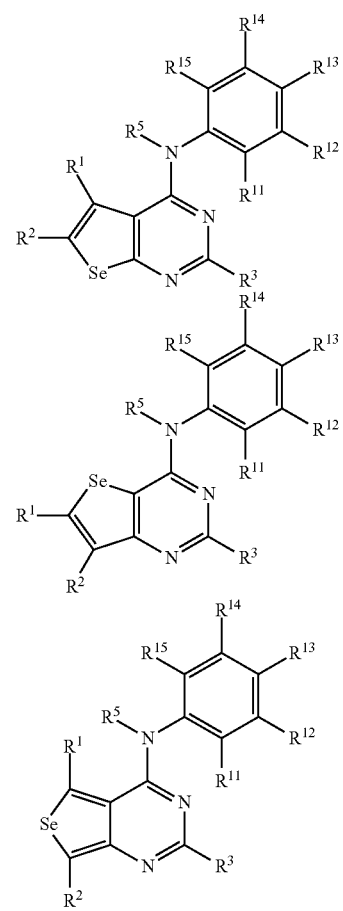

$R^{11}$, $R^{12}$, $R^{13}$, $R^{14}$, and $R^{15}$
is independently selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkyl-carbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino $C_{1-6}$alkyl, di($C_{1-6}$alkyl)amino$C_{1-6}$alkyl, $C_{1-6}$alkylsulfinyl, $C_{1-6}$alkylsulfonyl, and a phenyl, benzyl, a five membered heteroaromatic ring containing one or more heteroatoms selected from sulfur, oxygen, nitrogen and selenium, with proviso that no more than one oxygen or sulfur or selenium atom is present; phenyl or 5-membered heteroaromatic ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino-$C_{1-6}$alkoxy, $C_{1-6}$alkylamino $C_{1-6}$alkyl, di($C_{1-6}$alkyl)amino$C_{1-6}$alkyl, $C_{1-6}$alkylsulfinyl, $C_{1-6}$alkylsulfonyl;

In a preferred embodiment, the disclosure provides substituted 4-(arylamino)selenophenopyrimidine compounds represented by the formula (I), wherein A is N; B is $NR^5$ and Ar is heteroaryl ring; heteroaryl is 6-membered or 5-membered heteroaromatic ring; 6-membered heteroaromatic rings include pyridine, pyradazine, pyrimidine and pyrazine. The 6-membered heteroaromatic ring is selected from;

(a) optionally substituted pyridine;

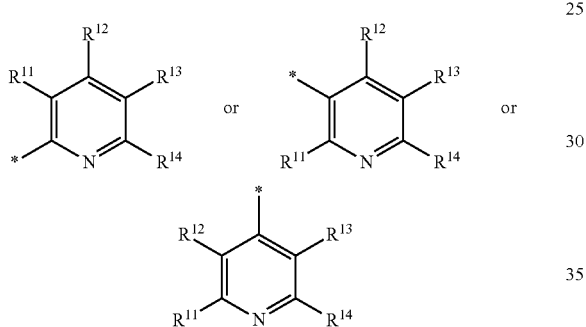

wherein:
* indicates the point of attachment to B of formula (I) and is selected from the following;

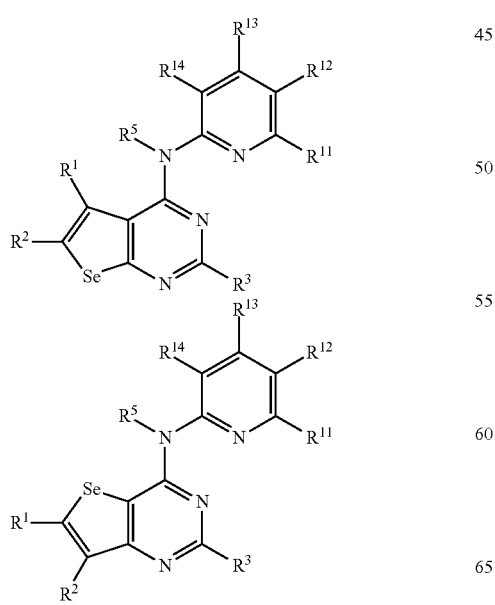

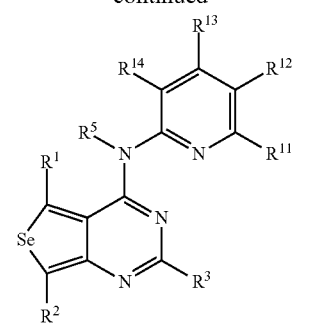

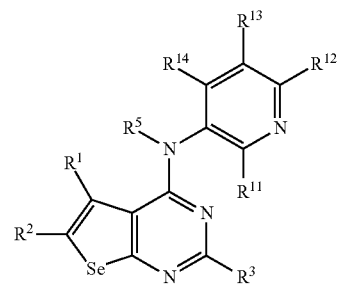

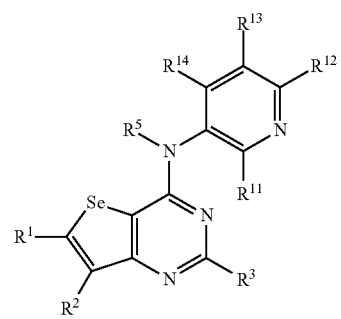

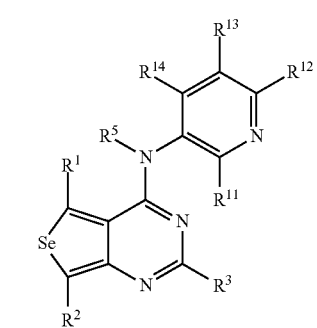

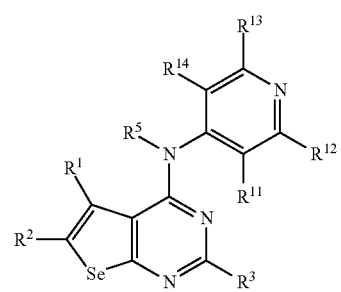

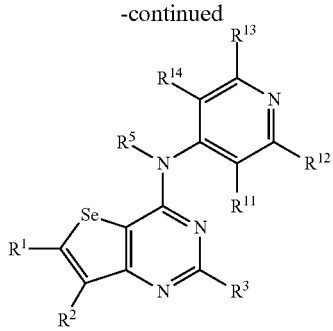

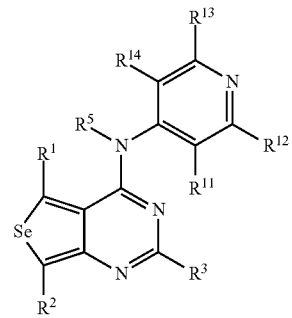

R$^1$, R$^2$, R$^3$, R$^5$, R$^{11}$, R$^{12}$, R$^{13}$, and R$^{14}$
is independently selected from the groups specified above;
(b) optionally substituted pyradazine;

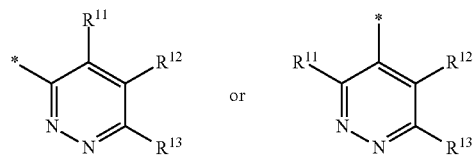

wherein
* indicates the point of attachment to B of formula (I) and is selected from the groups specified above following;

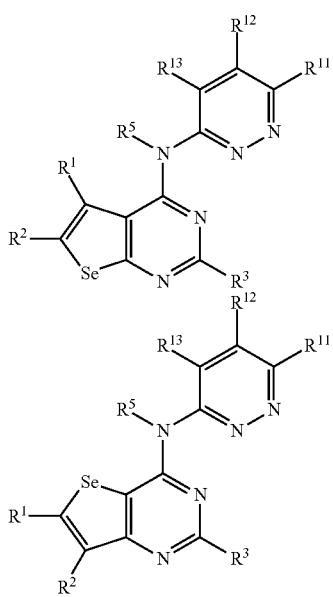

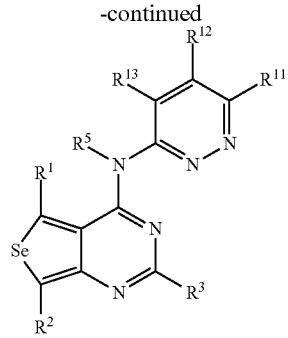

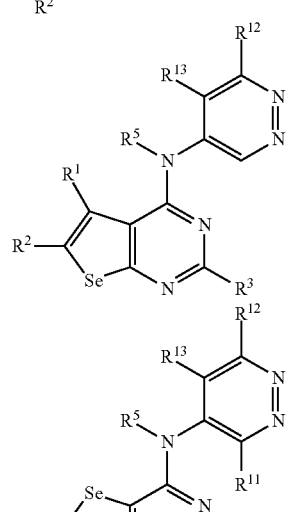

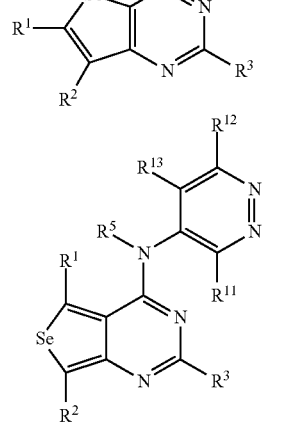

R$^1$, R$^2$, R$^3$, R$^5$, R$^{11}$, R$^{12}$, and R$^{13}$
is independently selected from the groups specified above;
(c) optionally substituted pyrimidine;

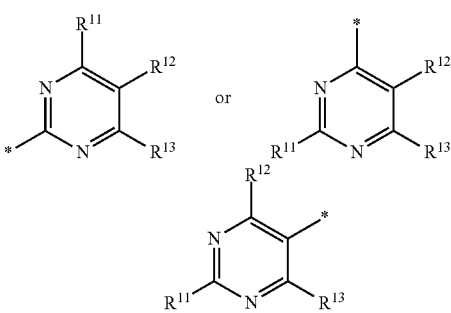

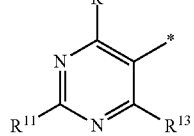

wherein;
* indicates the point of attachment to B of formula (I) and is selected from the following;
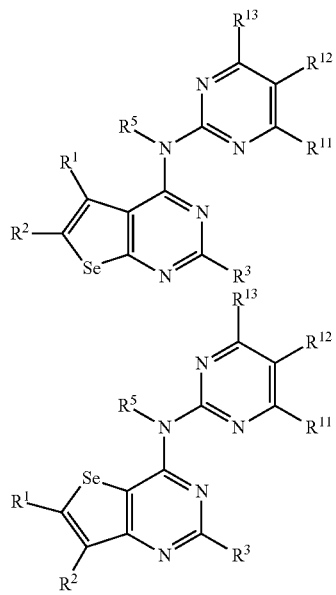
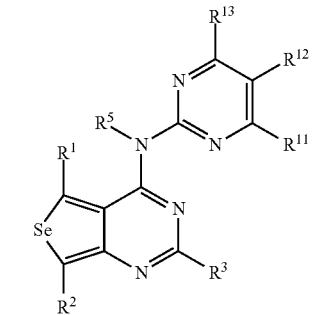
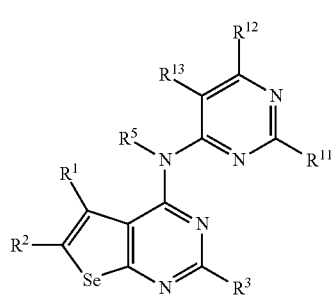
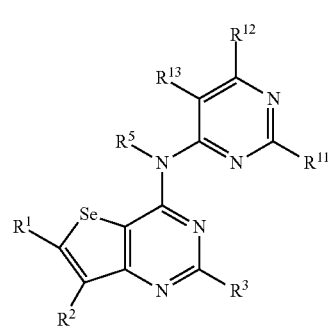
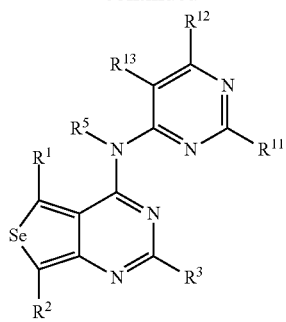
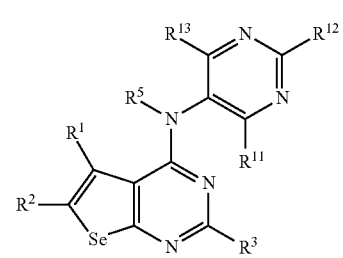
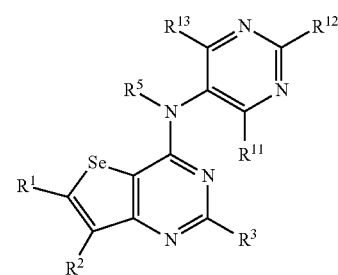
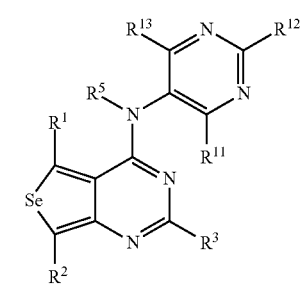
$R^1$, $R^2$, $R^3$, $R^5$, $R^{11}$, $R^{12}$, and $R^{13}$
is independently selected from the groups specified above;
(d) optionally substituted pyrazine;
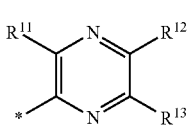
wherein;
* indicates the point of attachment to B of formula (I) and is selected from the following;

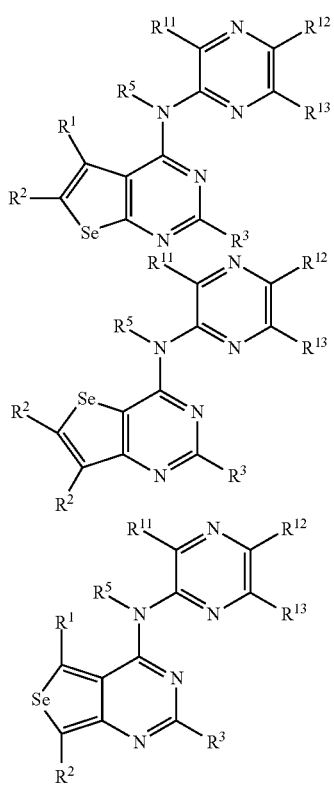

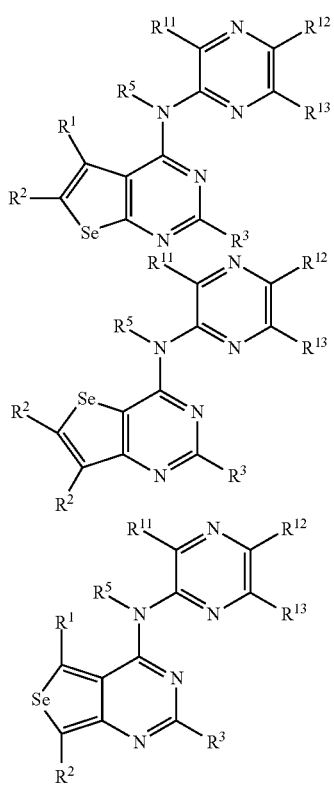

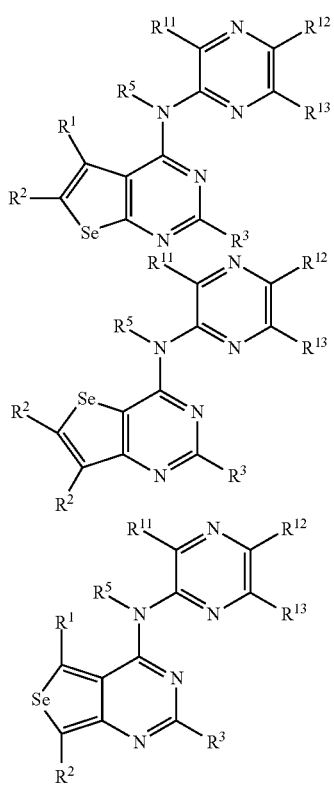

R¹, R², R³, R⁵, R¹¹, R¹², and R¹³
is independently selected from the groups specified above.

In another embodiment, the disclosure provides substituted 4-(arylamino)selenophenopyrimidine compounds represented by the formula (I), wherein Ar is 5-membered heteroaromatic ring containing one or more heteroatoms selected from sulfur, oxygen and nitrogen; such rings include thiophene, furan, pyrrole, pyrazole, imidazole, oxazole, isoxazole, thiazole and isothiazole. The 5-membered aromatic ring is selected from;

(a) optionally substituted thiophene;

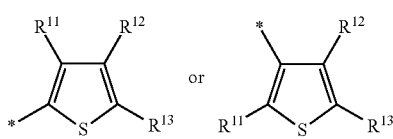

wherein;
* indicates the point of attachment to B of formula (I) and is selected from the following;

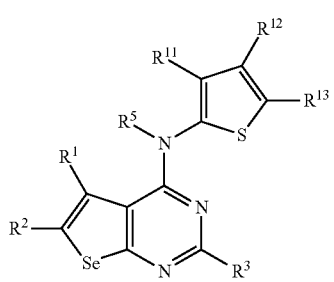

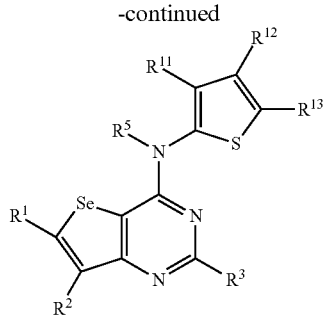

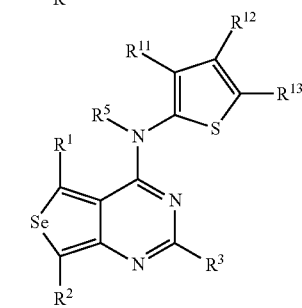

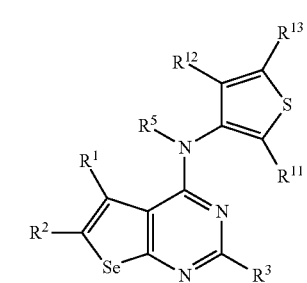

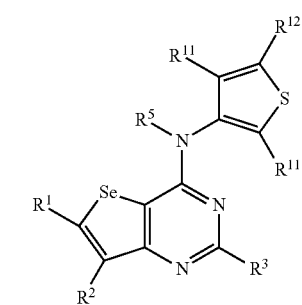

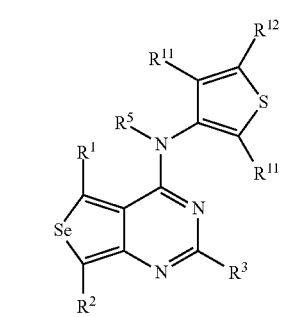

R¹, R², R³, R⁵, R, R¹², and R¹³
is independently selected from the groups specified above;

(b) optionally substituted furan;
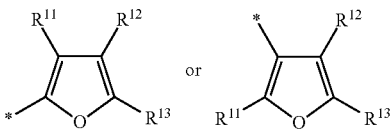
wherein;
* indicates the point of attachment to B of formula (I) and is selected from the following;
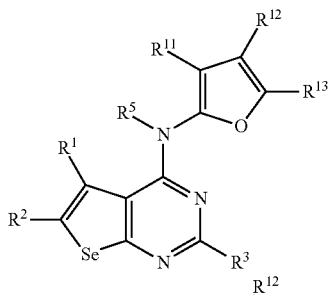
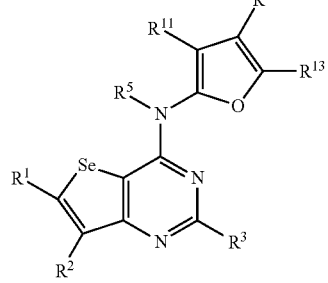
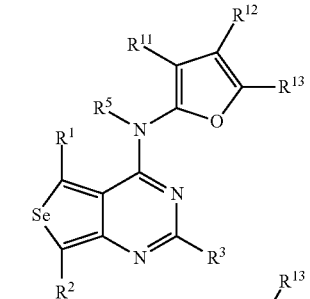
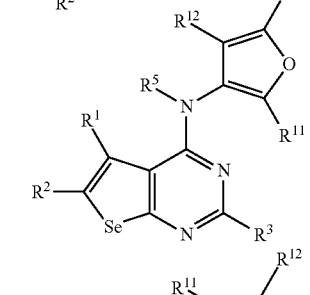
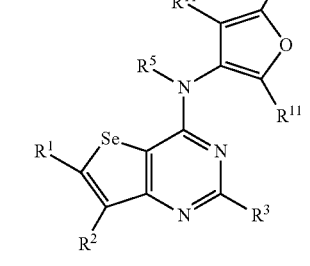
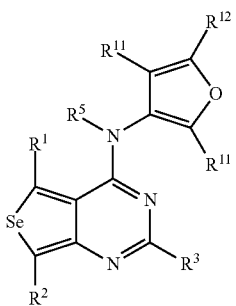
$R^1$, $R^2$, $R^3$, $R^5$, $R^{11}$, $R^{12}$, and $R^{13}$ is independently selected from the groups specified above;
(c) optionally substituted pyrrole;
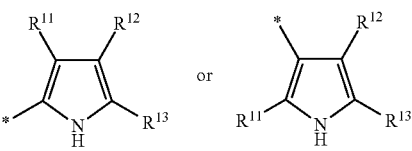
wherein;
* indicates the point of attachment to B of formula (I) and is selected from the following;
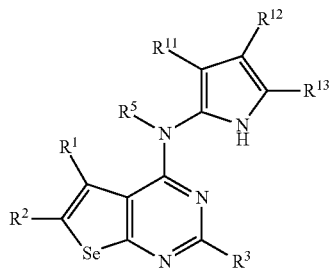
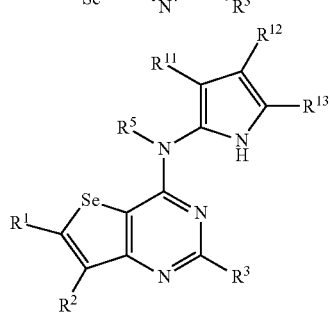
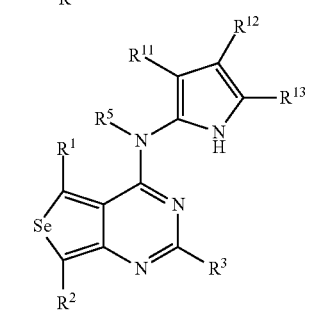

-continued

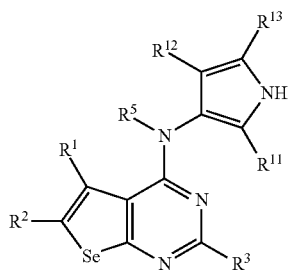

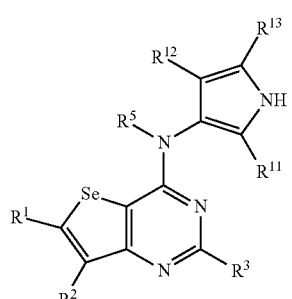

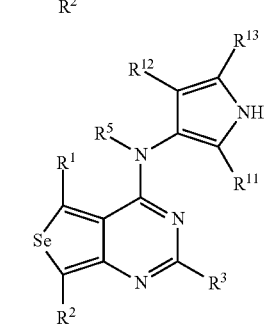

$R^1$, $R^2$, $R^3$, $R^5$, $R^{11}$, $R^{12}$, and $R^{13}$
is independently selected from the groups specified above;
(d) optionally substituted pyrazole;

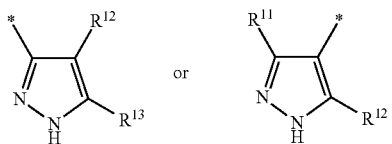

wherein;
* indicates the point of attachment to B of formula (I) and is selected from the following;

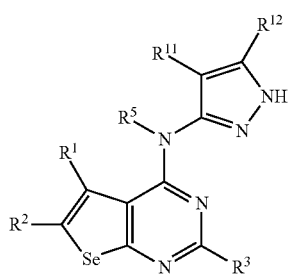

-continued

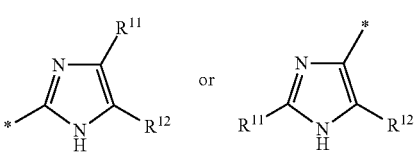

$R^1$, $R^2$, $R^3$, $R^5$, $R^{11}$, and $R^{12}$
is independently selected from the groups specified above;
(e) optionally substituted imidazole;

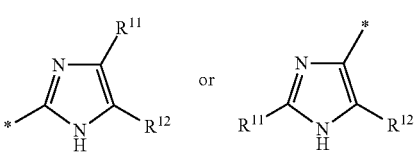

wherein;
* indicates the point of attachment to B of formula (I) and is selected from the following;
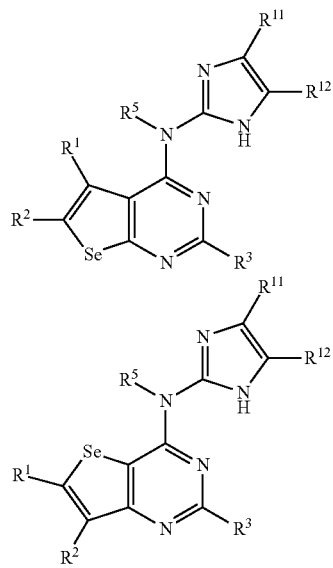
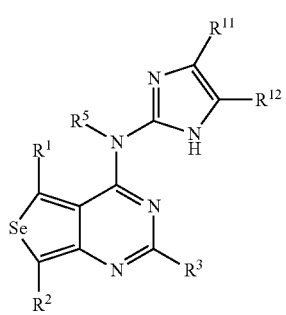
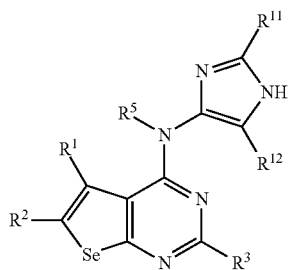
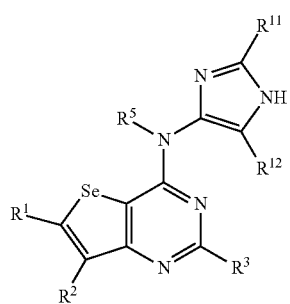
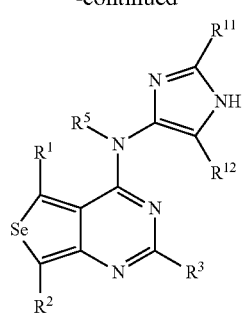
$R^1$, $R^2$, $R^3$, $R^5$, $R^{11}$, and $R^{12}$ is independently selected from the groups specified above;
(f) optionally substituted oxazole;
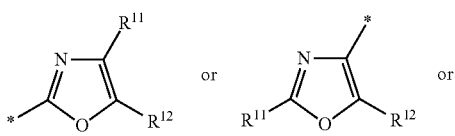
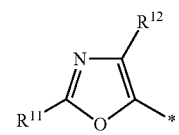
wherein;
* indicates the point of attachment to B of formula (I) and is selected from the following;
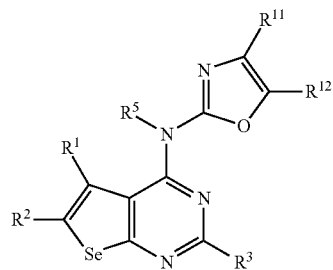
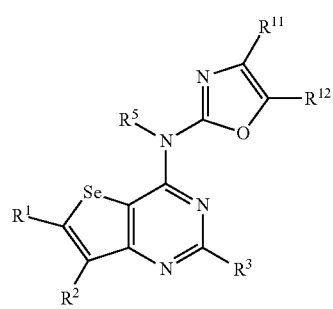

31
-continued
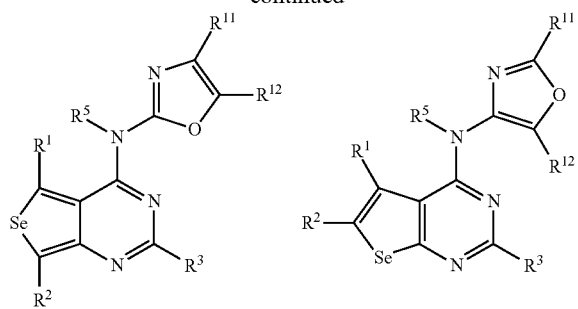
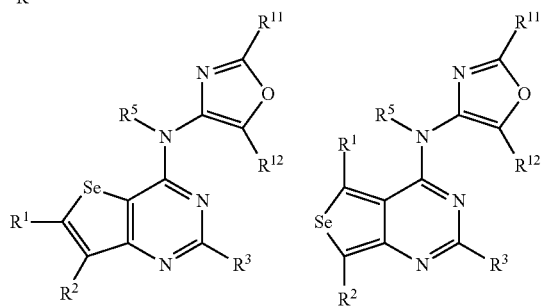
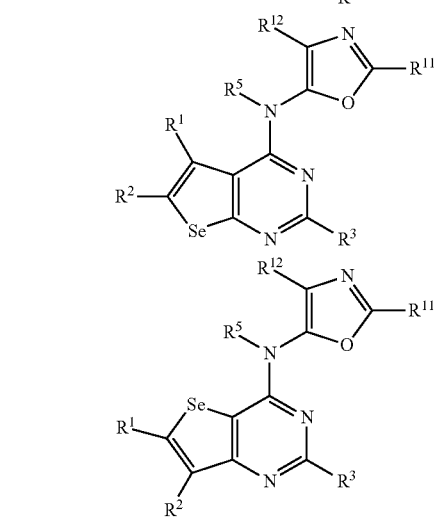
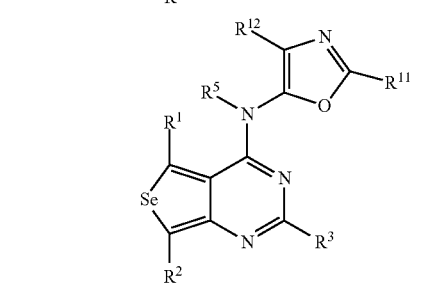
$R^1$, $R^2$, $R^3$, $R^5$, $R^{11}$, and $R^{12}$ is independently selected from the groups specified above;
(g) optionally substituted isoxazole;
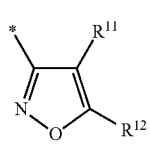 or 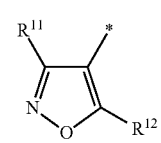 or
32
-continued
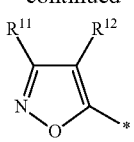
wherein;
* indicates the point of attachment to B of formula (I) and is selected from the following;
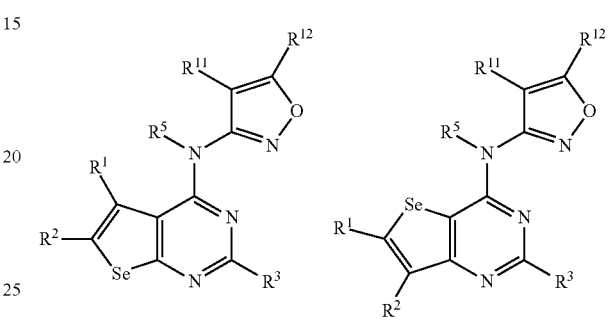
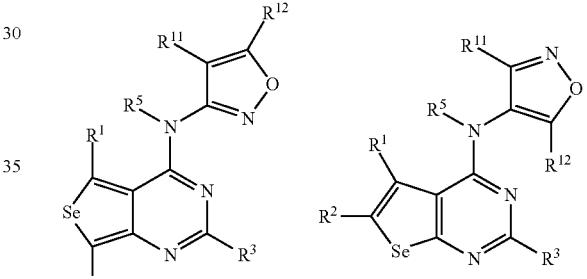
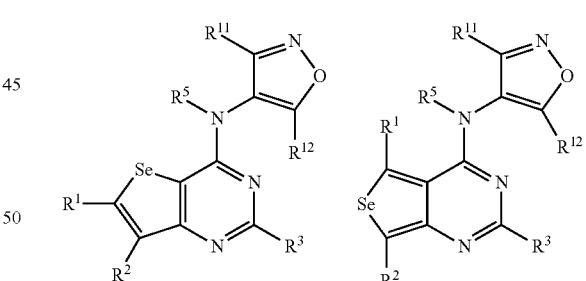
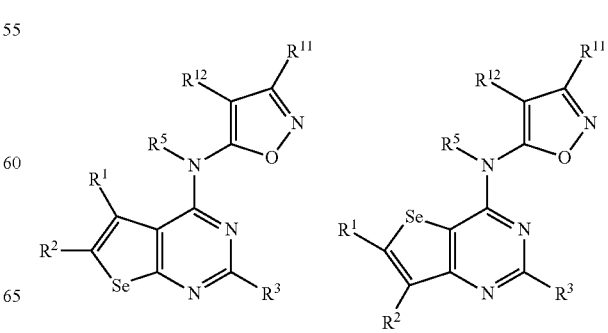

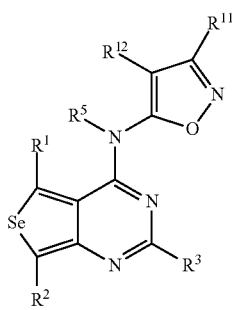
R$^1$, R$^2$, R$^3$, R$^5$, R$^{11}$, and R$^{12}$
is independently selected from the groups specified above;
(h) optionally substituted thiazole;
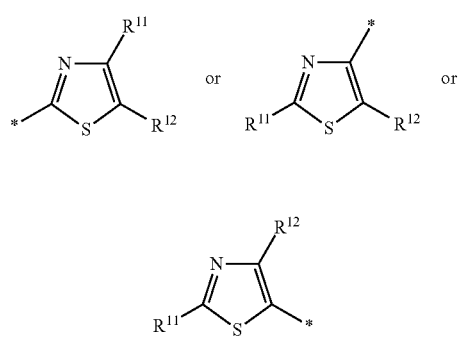
wherein;
* indicates the point of attachment to B of formula (I) and is selected from the following;
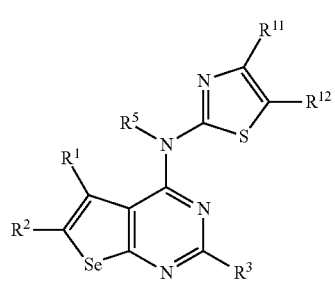
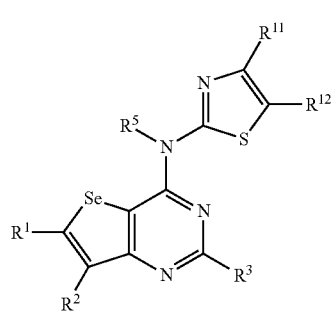
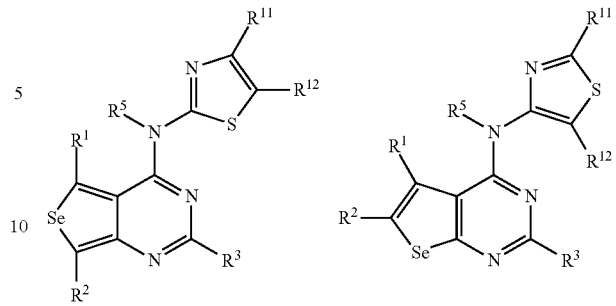
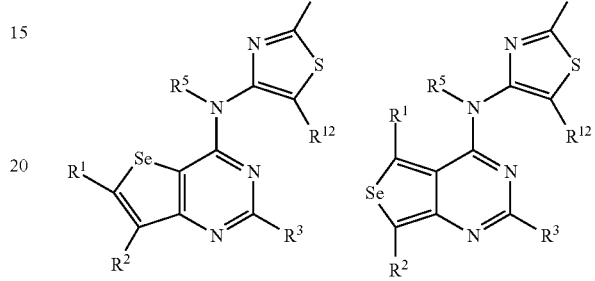
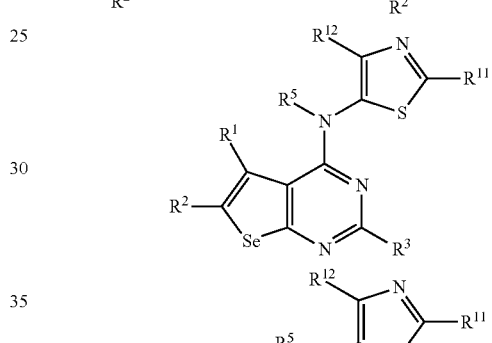
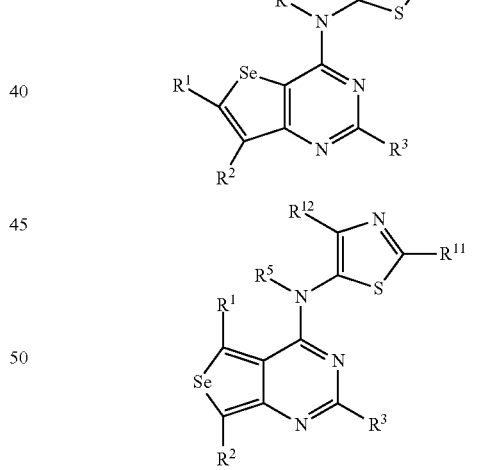
R$^1$, R$^2$, R$^3$, R$^5$, R$^{11}$, and R$^{12}$
is independently selected from the groups specified above;
(i) optionally substituted isothiazole;
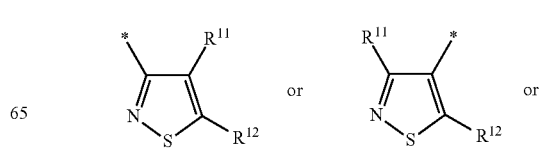

-continued

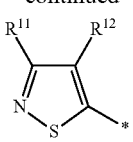

wherein;

* indicates the point of attachment to B of formula (I) and is selected from the following;

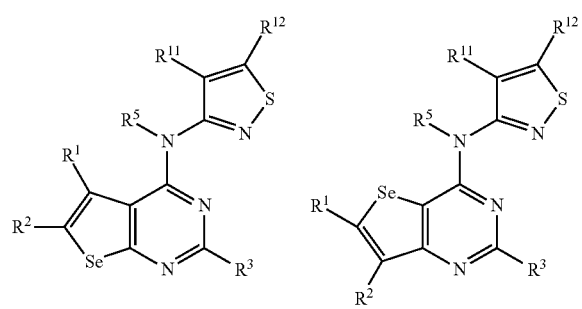

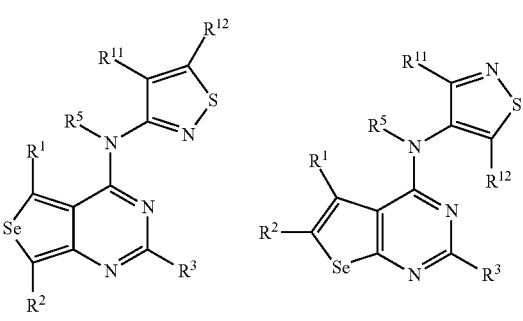

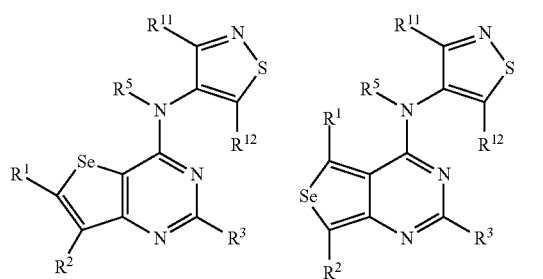

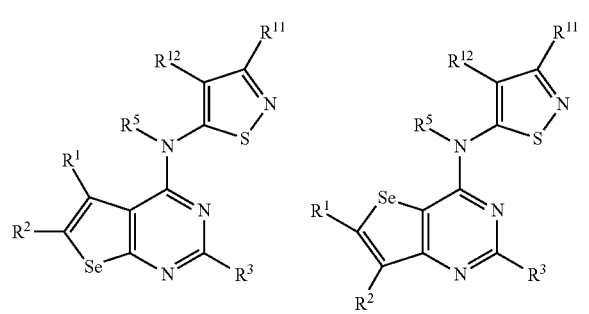

-continued

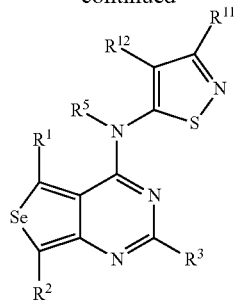

$R^1$, $R^2$, $R^3$, $R^5$, $R^{11}$, and $R^{12}$
is independently selected from the groups specified above.

In other preferred embodiment, the disclosure provides substituted 4-(arylamino)selenophenopyrimidine compounds represented by the following formula (I),

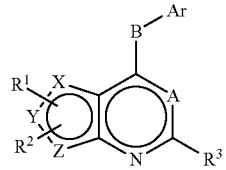

Formula (I)

wherein $R^1$ and $R^2$
are joined, and taken together with the atoms to which they are attached, form optionally substituted aryl or optionally substituted heteroaryl ring fused with selenophene and is selected from;

(a) optionally substituted aryl fused;

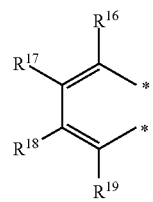

wherein;

* indicates the point of attachment to $R^1$ and $R^2$ in formula I and is selected from the following;

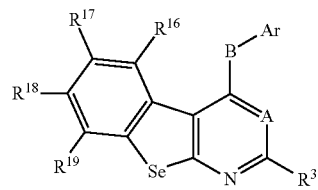

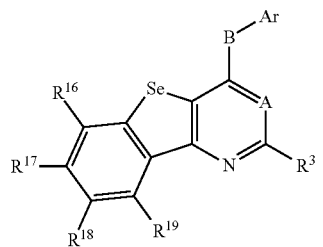

R$^{16}$, R$^{17}$, R$^{18}$ and R$^{19}$ is independently selected from hydrogen, halogen, hydroxy, formyl, carboxylic acid, amino, nitro, cyano, sulfonic acid, thiole, trihalomethyl, sulfonamide, C$_{1-6}$alkyl, C$_{1-6}$secondaryalkyl, C$_{1-6}$tertiaryalkyl, C$_{2-6}$alkenyl, C$_{2-6}$alkynyl, C$_{1-4}$alkylcarbonyl, C$_{1-4}$alkoxycarbonyl, aminocarbonyl, C$_{1-6}$alkylaminocarbonyl, di(C$_{1-6}$alkyl)aminocarbonyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{1-6}$alkylamino, di(C$_{1-6}$alkyl)amino, aminoC$_{1-6}$alkyl, aminoC$_{1-6}$alkoxy, C$_{1-6}$alkylaminoC$_{1-6}$alkyl, di(C$_{1-6}$alkyl)aminoC$_{1-6}$alkyl, C$_{1-6}$alkylsulfinyl, C$_{1-6}$alkylsulfonyl, and a phenyl, benzyl, a five membered heteroaromatic ring containing one or more heteroatoms selected from sulfur, oxygen, nitrogen and selenium, with proviso that no more than one oxygen or sulfur or selenium atom is present; phenyl or 5-membered heteroaromatic ring optionally substituted by halogen, hydroxy, formyl, carboxylic acid, amino, nitro, cyano, sulfonic acid, thiole, trihalomethyl, sulfonamide, C$_{1-6}$alkyl, C$_{2-6}$alkenyl, C$_{2-6}$alkynyl, C$_{1-4}$alkylcarbonyl, C$_{1-4}$alkoxycarbonyl, aminocarbonyl, C$_{1-6}$alkylaminocarbonyl, di(C$_{1-6}$alkyl)aminocarbonyl, haloC$_{1-6}$alkyl, hydroxyC$_{1-6}$alkyl, C$_{1-6}$alkoxy, haloC$_{1-6}$alkoxy, hydroxy C$_{1-6}$alkoxy, C$_{3-7}$cycloalkyl, C$_{3-7}$cycloalkoxy, C$_{1-6}$alkylamino, di(C$_{1-6}$alkyl)amino, aminoC$_{1-6}$alkyl, aminoC$_{1-6}$alkoxy, C$_{1-6}$alkylaminoC$_{1-6}$alkyl, di(C$_{1-6}$alkyl) aminoC$_{1-6}$alkyl, C$_{1-6}$alkylsulfinyl, C$_{1-6}$alkylsulfonyl;

(b) optionally substituted pyridine fused;

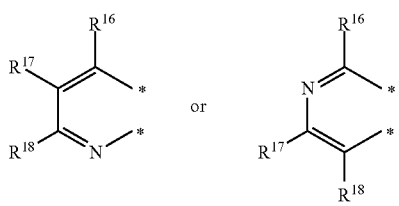

wherein;

* indicates the point of attachment to R$^1$ and R$^2$ in formula I and is selected from the following;

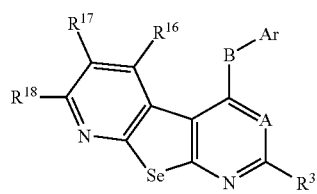

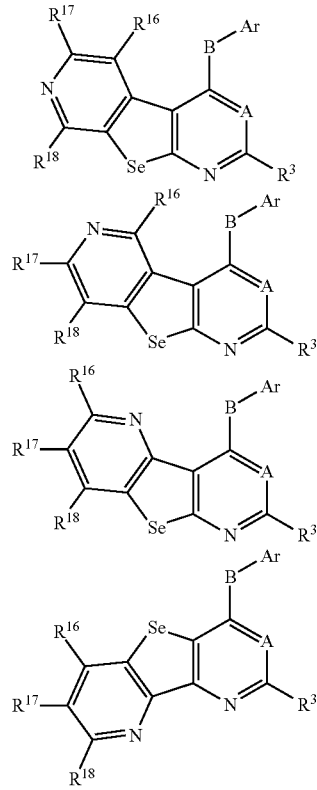

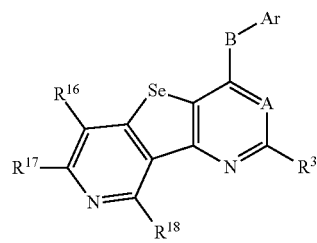

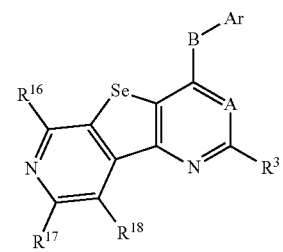

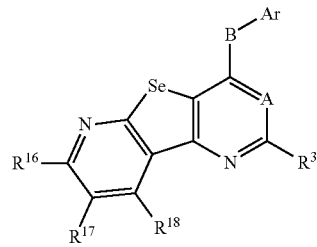

R$^3$, R$^{16}$, R$^{17}$, and R$^{18}$ is independently selected from the groups specified above.

(c) optionally substituted furan fused;

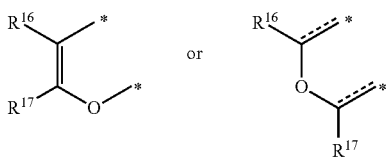 or wherein;

* indicates the point of attachment to $R^1$ and $R^2$ in formula I and is selected from the following;

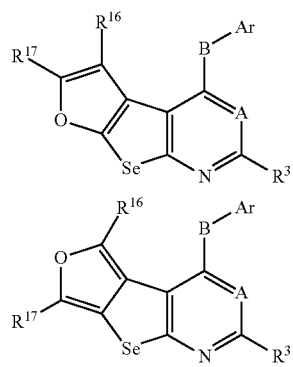

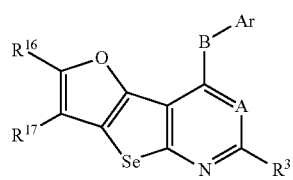

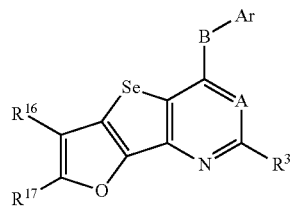

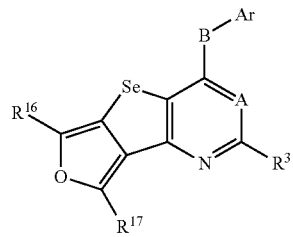

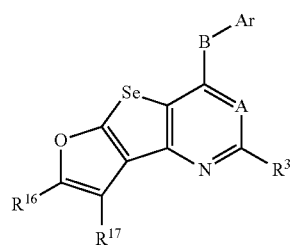

$R^3$, $R^{16}$, and $R^{17}$ is independently selected from the groups specified above.

(d) optionally substituted thiophene fused;

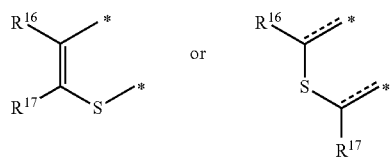 or wherein;

* indicates the point of attachment to $R^1$ and $R^2$ in formula I and is selected from the following;

$R^3$, $R^{16}$, and $R^{17}$ is independently selected from the groups specified above.

(e) optionally substituted selenophene fused;

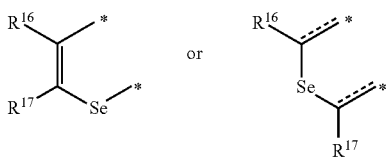

wherein;
* indicates the point of attachment to $R^1$ and $R^2$ in formula I and is selected from the following;

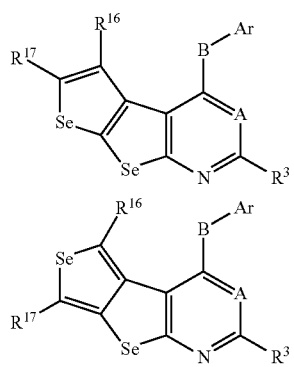

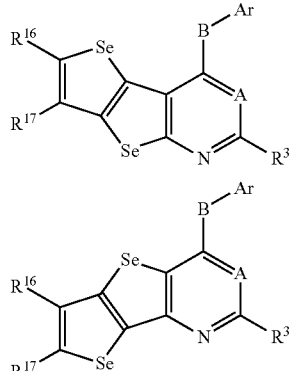

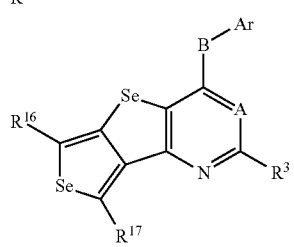

$R^3$, $R^{16}$, and $R^{17}$ is independently selected from the groups specified above.

(f) optionally substituted pyrrole fused;

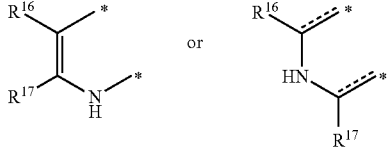

wherein;
* indicates the point of attachment to $R^1$ and $R^2$ in formula I and is selected from the following;

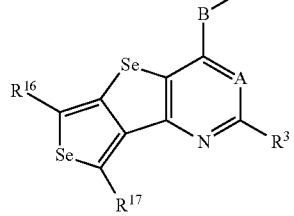

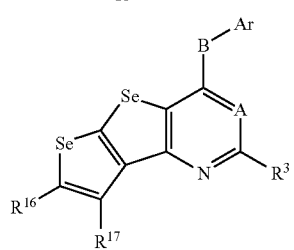

$R^3$, $R^{16}$, and $R^{17}$ is independently selected from the groups specified above.

In other preferred embodiment, the disclosure provides substituted 4-(arylamino)selenophenopyrimidine compounds represented by the following formula (I), Formula (I)

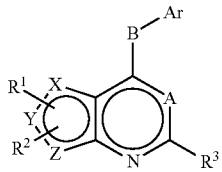

wherein
R¹ and R²
are joined, and taken together with the atoms to which they are attached, form optionally substituted cycloalkyl or optionally substituted heterocycloalkyl ring fused with selenophene and is selected from;
(a) optionally substituted 6-membered cycloalkyl fused;

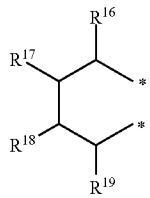

wherein;
* indicates the point of attachment to R¹ and R² in formula I and is selected from the following;

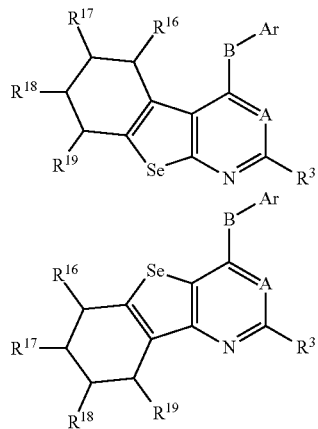

R³, R¹⁶, R¹⁷, R¹⁸ and R¹⁹
is independently selected from the groups specified above.
(b) optionally substituted 5-membered cycloalkyl fused;

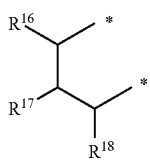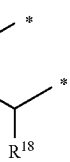

wherein;
* indicates the point of attachment to R¹ and R² in formula I and is selected from the following;

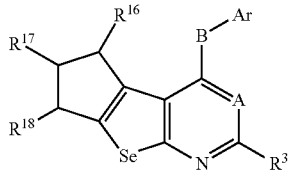

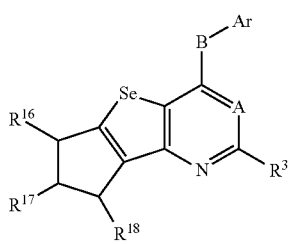

R³, R¹⁶, R¹⁷ and R¹⁸
is independently selected from the groups specified above.
(c) optionally substituted 6-membered heterocycloalkyl fused;

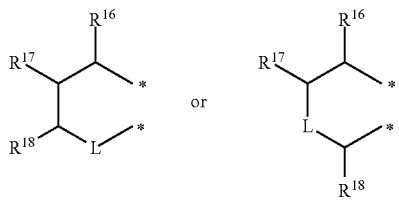

wherein;
* indicates the point of attachment to R¹ and R² in formula I, L is selected from NR⁸; and R¹⁶, R¹⁷, R¹⁸ and R⁸ is independently selected from the groups specified above;

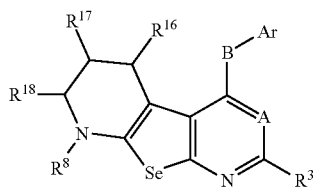

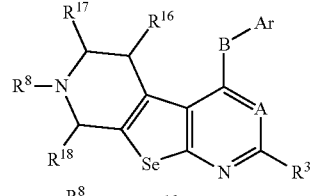

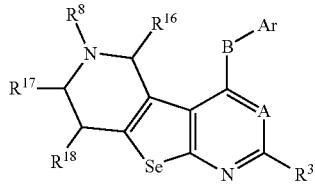

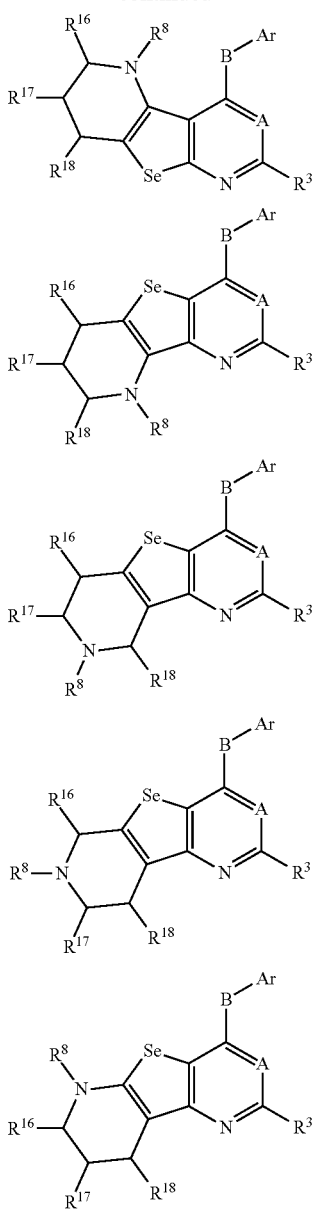

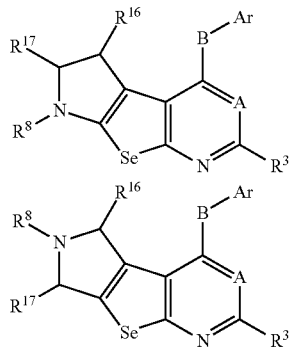

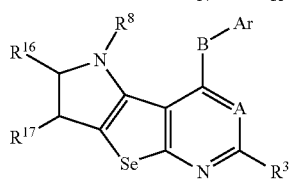

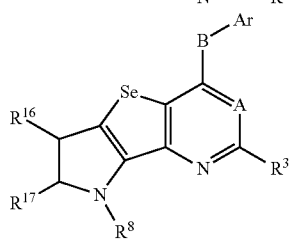

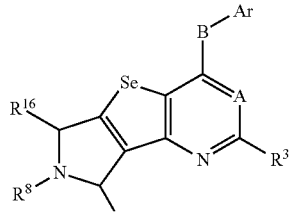

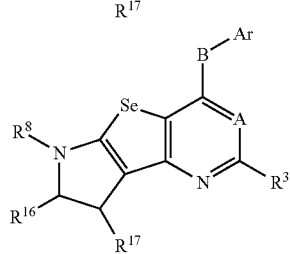

$R^3$, $R^8$, $R^{16}$, $R^{17}$ and $R^{18}$
is independently selected from the groups specified above.

(d) optionally substituted 5-membered heterocycloalkyl fused;

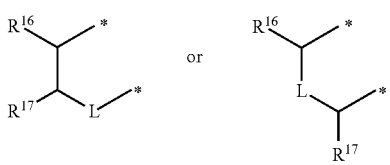

wherein;

* indicates the point of attachment to $R^1$ and $R^2$ in formula I, L is selected from $NR^8$; and $R^{16}$, $R^{17}$ and $R^8$ is independently selected from the groups specified above.

$R^3$, $R^8$, $R^{16}$ and $R^{17}$
is independently selected from the groups specified above.

Unless otherwise stated, the following definitions apply for the substituents and residues used throughout this specification and claims:

"Alkyl" as used herein in general represents a normal alkyl, secondary alkyl or tertiary alkyl having 1 to 6 carbon atoms. Non-limiting examples include methyl, ethyl, n-propyl, isopropyl, n-butyl, isobutyl, sec-butyl, tert-butyl, pentyl, isopentyl, neopentyl, hexyl, isohexyl. The same applies to radicals such as alkylcarbonyl, alkoxy, alkylamino, dialkylamino, alkylsulfonyl, haloalkyl and the like.

"Alkenyl" as used herein in general represents a straight-chain or branched unsaturated hydrocarbon radical having 2 to 6 carbon atoms and one carbon-carbon double bond. Non-limiting examples include —CH=CH$_2$, —CH=CHCH$_3$, —C(CH$_3$)=CH$_2$, —CH$_2$CH=CH$_2$, —CH=C(CH$_3$)$_2$, —C(CH$_3$)=CHCH$_3$, —CH$_2$CH=CHCH$_3$, —CH$_2$C(CH$_3$)

=CH₂, —CH₂CH₂CH=CH₂, —CH₂CH=CHCH₂CH₃, —CH₂CH₂CH=CHCH₃, —CH₂CH=C(CH₃)₂, —CH₂CH₂C(CH₃)=CH₂, —CH=CHCH₂CH₂CH₃ etc.

"Alkynyl" as used herein in general represents a straight-chain or branched unsaturated hydrocarbon radical having 2 to 6 carbon atoms and one carbon-carbon triple bond. Non-limiting examples include —C≡CH, —C≡CCH₃, —CH₂C≡CH, —C≡CH₂CH₃, —CH₂CH₂C≡CH, —CH₂C≡CCH₃ etc.

"Alkoxy" as used herein illustratively and preferably represents methoxy, ethoxy, n-propoxy, iso-propoxy, n-butoxy and tert-butoxy etc.

"Alkylcarbonyl" as used herein in general represents a straight-chain or branched alkyl radical having 1 to 6 carbon atoms which is bonded via a carbonyl group to the rest of the molecule. Non-limiting examples include acetyl, n-propionyl, n-butyryl, isobutyryl, pivaloyl.

"Alkoxycarbonyl" as used herein illustratively and preferably represents methoxycarbonyl, ethoxycarbonyl, n-propoxycarbonyl, iso-propoxycarbonyl, n-butoxycarbonyl, iso-butoxycarbonyl and tert-butoxycarbonyl etc.

"Alkylsulfonyl" as used herein in general represents a straight-chain or branched alkyl radical having 1 to 6 carbon atoms which is bonded via a sulfonyl (—SO₂—) group to the rest of the molecule. Non-limiting examples include methylsulfonyl, ethylsulfonyl, n-propylsulfonyl, iso-propylsulfonyl, n-butylsulfonyl, iso-butylsulfonyl and tert-butylsulfonyl etc.

"Monoalkylamino" as used herein in general represents an amino radical having one alkyl residue attached to the nitrogen atom. Non-limiting examples include methylamino, ethylamino, n-propylamino, isopropylamino, n-butylamino, iso-butylamino, and tert-butylamino. The same applies to radicals such as monoalkyl aminocarbonyl etc.

"Dialkylamino" as used herein in general represents an amino radical having two independently selected alkyl residues attached to the nitrogen atom. Non-limiting examples include N,N-dimethylamino, N,N-diethylamino, N,N-diisopropylamino, N-ethyl-N-methylamino, N-methyl-N-n-propylamino, N-iso-propyl-N-n-propylamino, N-secondary-butyl-N-n-methylamino, and N-tert-butyl-N-methylamino. The same applies to radicals such as dialkylaminocarbonyl etc.

"Monoalkylaminocarbonyl" as used herein illustratively and preferably represents methylaminocarbonyl, ethylaminocarbonyl, n-propylaminocarbonyl, isopropylaminocarbonyl, n-butylaminocarbonyl, sec-butylaminocarbonyl and tert-butylaminocarbonyl etc.

"Dialkylaminocarbonyl" as used herein illustratively and preferably represents N,N-dimethylaminocarbonyl, N,N-diethylaminocarbonyl, N,N-diisopropylaminocarbonyl, N-ethyl-N-methylaminocarbonyl, N-methyl-N-n-propylaminocarbonyl, N-isopropyl-N-n-propylaminocarbonyl, N-butyl-N-n-propylaminocarbonyl, N-iso-butyl-N-n-propylaminocarbonyl, N-methyl-N-n-butylaminocarbonyl, N-methyl-N-iso-butylaminocarbonyl, N-methyl-N-tert-butylaminocarbonyl and N-tert-butyl-N-methyl-aminocarbonyl etc.

"Alkylcarbonylamino" as used herein in general represents a straight-chain or branched alkyl radical having 1 to 6 carbon atoms which is bonded via a carbonylamino (—CO—NH—) group to the rest of the molecule and which is attached to the carbon atom of that group. Non-limiting examples include acetylamino, n-propionylamino, n-butyrylamino, iso-butyrylamino, tert-butyrylamino and pivaloylamino etc.

"Alkoxycarbonylamino" as used herein illustratively and preferably represents methoxycarbonylamino, ethoxycarbonylamino, n-propoxycarbonylamino, isopropoxycarbonylamino, n-butoxycarbonylamino, iso-butoxycarbonylamino and tert-butoxycarbonylamino etc.

"Cycloalkyl" as used herein in general represents a mono-, bi- or tricyclic saturated hydrocarbon radical having 3 to 7 carbon atoms. Preference is given to monocyclic cycloalkyl radicals having 3 to 7 carbon atoms. Non-limiting examples include cyclopropyl, cyclobutyl, cyclopentyl, cyclohexyl, cycloheptyl, bicyclo[2.2.1]heptyl, adamantly etc.

"Heterocycloalkyl" as used herein in general represents a mono- or bicyclic, saturated heterocyclic radical having a total number of 3 to 10 carbon atoms and up to 2 heteroatoms and/or hetero-groups independently selected from the group consisting of N, O, S, SO and SO₂, which ring system can be bonded via a ring carbon atom or, if possible, via a ring nitrogen atom. Non-limiting examples include aziridinyl, azetidinyl, oxetanyl, thietanyl, pyrrolidinyl, pyrazolidinyl, tetrahydrofuranyl, thiolanyl, sulfolanyl, 1,3-dioxolanyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,1-dioxidothiomorholinyl, perhydroazepinyl, perhydro-1,4-diazepinyl, perhydro-1,4-oxazepinyl, perhydroazocinyl, octahydropyrrolo[3,4-b]pyrrolyl, octahydroisoindolyl, octahydropyrrolo[3,4-b]pyridyl, octahydropyrrolo[1,2-a]pyrazinyl, decahydroisoquinolinyl, 7-azabicyclo[2.2.1]heptyl, 3-azabicyclo[3.2.0]heptyl, 7-azabicyclo-[4.1.0]heptyl, 2,5-diazabicyclo[2.2.1]heptyl, 2-oxa-5-azabicyclo[2.2.1]heptyl, 2-azabicyclo-[2.2.2]octyl, 3-azabicyclo[3.2.1]octyl, 8-azabicyclo[3.2.1]octyl, 8-oxa-3-azabicyclo[3.2.1]octyl, 3-oxa-9-azabicyclo[3.3.1]nonyl. Particular preference is given to 5- to 7-membered monocyclic heterocycloalkyl radicals having up to 2 heteroatoms selected from the group consisting of N, O and S, such as illustratively and preferably tetrahydrofuranyl, 1,3-dioxolanyl, pyrrolidinyl, tetrahydropyranyl, 1,4-dioxanyl, piperidinyl, piperazinyl, morpholinyl, thiomorpholinyl, perhydroazepinyl, perhydro-1,4-diazepinyl and perhydro-1,4-oxazepinyl.

"Heteroaryl" as used herein in general represents a monocyclic, aromatic heterocyclic radical having 5 or 6 ring atoms, including up to 3 heteroatoms independently selected from the group consisting of N, O, S and Se, which ring system can be bonded via a ring carbon atom or, if possible, via a ring nitrogen atom. Preference is given to 6-membered heteroaryl radicals having up to 2 nitrogen atoms, such as pyridyl, pyrimidyl, pyridazinyl and pyrazinyl, and to 5-membered heteroaryl radicals having up to 3 heteroatoms selected from the group consisting of N, O, S and Se, such as illustratively and preferably thienyl, furyl, pyrrolyl, selenophenyl, thiazolyl, oxazolyl, isothiazolyl, isoxazolyl, pyrazolyl, imidazolyl, oxadiazolyl, thiadiazolyl, triazolyl.

"Halogen" as used herein represents fluorine, chlorine, bromine and iodine.

The compounds according to this disclosure can also be present in the form of their salts, hydrates and/or solvates.

Salts for the purposes of the present disclosure are preferably pharmaceutically acceptable salts of the compounds disclosed herein.

Pharmaceutically acceptable salts include acid addition salts of mineral acids, carboxylic acids and sulfonic acids, for example salts of hydrochloric acid, hydrobromic acid, nitric acid, sulfuric acid, phosphoric acid, methanesulfonic acid, ethanesulfonic acid, toluenesulfonic acid, benzenesulfonic acid, formamidinesulfonic acid, naphthalenesulfonic acid, formic acid, acetic acid, propionic acid, lactic acid, tartaric acid, malic acid, citric acid, fumaric acid, maleic acid, benzoic acid, malonic acid, oxalic acid and succinic acid.

Pharmaceutically acceptable salts also include salts of customary bases, such as for example and preferably alkali metal salts (for example sodium and potassium salts), alkaline earth metal salts (for example calcium and magnesium salts), and ammonium salts derived from ammonia or organic amines, such as illustratively alkylamines in general and preferably ethylamine, diethylamine, triethylamine, ethyldiisopropylamine, monoethanolamine, diethanolamine, triethanolamine, dicyclohexylamine, dimethylaminoethanol, dibenzylamine, N-methylmorpholine, N-methylpiperidine, dihydroabietylamine, arginine, lysine, ethylenediamine and polyamines such as putrescine and cadaverine.

Hydrates of the compounds disclosed herein or their salts are stoichiometric compositions of the compounds with water, such as, for example, hemi-, mono-, or dihydrates. Solvates of the compounds disclosed herein or their salts are stoichiometric compositions of the compounds with organic solvents.

The compounds of this disclosure may, either by nature of asymmetric centers or by restricted rotation, be present in the form of isomers (enantiomers, diastereomers). Any isomer may be present in which the asymmetric center is in the (R)-, (S)-, or (R,S) configuration.

It will also be appreciated that when two or more asymmetric centers are present in the compounds of the disclosure, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the disclosure.

Geometric isomers by nature of substituents about a double bond or a ring may be present in cis (=Z-) or trans (=E-) form, and both isomeric forms are encompassed within the scope of this disclosure.

All isomers, whether separated, pure, partially pure, or in racemic mixture, of the compounds of this disclosure are encompassed within the scope of this disclosure. The purification of said isomers and the separation of said isomeric mixtures may be accomplished by standard techniques known in the art. For example, diastereomeric mixtures can be separated into the individual isomers by chromatographic processes or selective crystallization, and racemates can be separated into the respective enantiomers either by chromatographic processes on chiral phases or by resolution.

In addition, all possible tautomeric forms of the compounds described above are included according to the present disclosure.

Some examples of compounds of formula (I) for treating or inhibiting or controlling a cell proliferative disorder such as cancer are:

(3-Chloro-4-fluorophenyl)-5,6,7,8-tetrahydrobenzo[1,2-b]pyrimidino[5,6-d]selenophen-4-ylamine (compd. No. 1);
(5-Bromo(3-pyridyl))-5,6,7,8-tetrahydrobenzo[1,2-b]pyrimidino[5,6-d]selenophen-4-ylamine (compd. No. 2);
(2,6-Dichloropyridin-4-yl)-5,6,7,8-tetrahydrobenzo[1,2-b]pyrimidino[5,6-d]selenophen-4-ylamine (compd. No. 3);
(2,6-Dichloropyrimidin-4-yl)-5,6,7,8-tetrahydrobenzo[1,2-b]pyrimidino[5,6-d]selenophen-4-ylamine (compd. No. 4);
Pyrazin-2-yl-5,6,7,8-tetrahydrobenzo[1,2-b]pyrimidino[5,6-d]selenophen-4-ylamine (compd. No. 5);
(2,5-Dibromo(3-thienyl)-5,6,7,8-tetrahydrobenzo[1,2-b]pyrimidino[5,6-d]selenophen-4-ylamine (compd. No. 6);
(5-tert-Butyl)-3-(5,6,7,8-tetrahydrobenzo[1,2-b]pyrimidino[5,6-d]selenophen-4-ylamino)thiophene-2-carboxamide (compd. No. 7);
5-(tert-Butyl)-2-(5,6,7,8-tetrahydrobenzo[1,2-b]pyrimidino[5,6-d]selenophen-4-ylamino)furan-3-carbonitrile (compd. No. 8);
5-Phenyl-2-(5,6,7,8-tetrahydrobenzo[1,2-b]pyrimidino[5,6-d]selenophen-4-ylamino)furan-3-carbonitrile (compd. No. 9);
2-Methylthio-4-(5,6,7,8-tetrahydrobenzo[1,2-b]pyrimidino[5,6-d]selenophen-4-ylamino)-1,3-thiazole-5-carbonitrile (compd. No. 10);
(2-Methylthio-5-nitro(1,3-thiazol-4-yl))-5,6,7,8-tetrahydrobenzo[1,2-b]pyrimidino[5,6-d]selenophen-4-ylamine (compd. No. 11);
4-(5,6,7,8-Tetrahydrobenzo[1,2-b]pyrimidino[5,6-d]selenophen-4-ylamino)benzene-sulfonamide (compd. No. 12);
[5-(tert-Butyl)selenopheno[3,2-e]pyrimidin-4-yl](3-chloro-4-fluorophenyl)amine (compd. No. 13);
(3-Chloro-4-fluorophenyl)(5-phenylselenopheno[3,2-e]pyrimidin-4-yl]amine (compd. No. 14);
4-[(3-Chloro-4-fluorophenyl)amino]-5-methylselenopheno[2,3-d]pyrimidine-6-carboxylic acid (compd. No. 15);
[(3-Chloro-4-fluorophenyl)(6-methyl-5-phenylselenopheno[3,2-e]pyrimidin-4-yl]amine (compd. No. 16);
4-[(3-Chloro-4-fluorophenyl)amino]-5-methylselenopheno[2,3-d]pyrimidine-6-carboxamide (compd. No. 17);
(3-Chloro-4-fluorophenyl)-5,6,7,8-tetrahydropyrimidino[5',6'-5,4]selenopheno[2,3-c]pyridine-4-ylamine (compd. No. 18);
4-[(3-Chloro-4-fluorophenyl)amino]-7-(methylsulfonyl)-5,6,7,8-tetrahydro-pyrimidino[5',4'-5,4]selenopheno[2,3-c]pyridine (compd. No. 19);
(3-Bromophenyl)-5,6,7,8-tetrahydropyrimidino[5',6'-5,4]selenopheno[2,3-c]pyridine-4-ylamine (compd. No. 20);
(3-Ethynylphenyl)-5,6,7,8-tetrahydropyrimidino[5',6'-5,4]selenopheno[2,3-c]pyridine-4-ylamine (compd. No. 21);
(3,4-Dichlorophenyl)-5,6,7,8-tetrahydropyrimidino[5',6'-5,4]selenopheno[2,3-c]pyridine-4-ylamine (compd. No. 22);
Methyl 5-methyl-4-(5,6,7,8-tetrahydropyrimidino[5',6'-5,4]selenopheno[2,3-c]pyridine-4-ylamino)thiophene-2-carboxylate (compd. No. 23);
{4-[3-Chloro-4-fluorophenyl)amino]-5-methylselenopheno[2,3-d]pyrimidin-6-yl}-N-(2-hydroxyethyl)carboxamide (compd. No. 24);
N-(2-Chloroethyl) {4-[3-chloro-4-fluorophenyl)amino]-5-methylselenopheno[2,3-d]pyrimidin-6-yl}carboxamide (compd. No. 25);
4-[(3-Chloro-4-fluorophenyl)amino]-5,6,8-trihydrobenzo[2,1-b]pyrimidino[5,4-d]selenophen-7-one (compd. No. 26);
(3-Chloro-4-fluorophenyl)-6,7,8,9-tetrahydrobenzo[1,2-d]pyrimidino[5,6-b]selenophen-4-ylamine (compd. No. 27);
[6-(tert-butyl)selenopheno[2,3-e]pyrimidin-4-yl](3-chloro-4-fluorophenyl)amine (compd. No. 28);
(3-Chloro-4-fluorophenyl)(6-phenylselenopheno[2,3-e]pyrimidin-4-yl)amine (compd. No. 29);
Benzo[d]pyrimidino[5,6-b]selenophen-4-yl(3-chloro-4-fluorophenyl)amine (compd. No. 30);
(3-Chloro-4-fluorophenyl)pyrimidino[4',5'-5,4]selenopheno[2,3-b]pyridin-4-ylamine (compd. No. 31);
Ethyl 4-[(3-chloro-4-fluorophenyl)amino]-5-methylthioselenopheno[3,4-d]pyrimidine-7-carboxylate (compd. No. 32);
(4-Chlorophenyl)methyl-5,6,7,8-tetrahydropyrimidino[5',6'-5,4]selenopheno[2,3-c]pyridine-4-ylamine (compd. No. 33);

(3-Chloro-4-fluorophenyl)(2-methyl(5,6,7,8-tetrahydrobenzo[1,2-b]pyrimidino[5,6-d]selenophen-4-yl)amine (compd. No. 34);

Synthesis of 4-(arylamino)selenophenopyrimidine

The present disclosure also relates to a process for preparing the compounds of formula (I), wherein all the groups are as defined earlier.

The compounds of formula (I) in which one of X or Y or Z is selenium and others are carbons such that the resulting is fused selenophene ring and A is N; B is NR⁵, can be made as shown in scheme A:

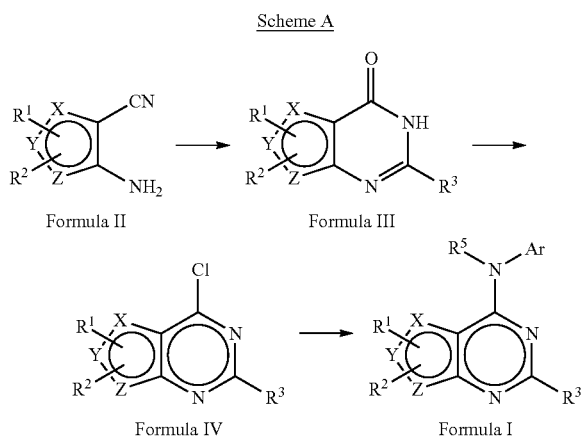

As shown in scheme A, aminoselenophenecarbonitrile of formula II or its equivalent (Aumann, K. M.; Scammells, P. J.; White, J. M.; Schiesser, C. H. Org. Biomol. Chem., 2007, 5, 1276-1281; Abdel-Hafez, Sh. H. Russian J. Org. Chem., 2005, 41, 396-401; Thomae, D.; Kirsch, G.; Seck, P. Synthesis, 2008, 1600-1606) is reacted with a mixture of formic acid and sulfuric acid to get pyrimidinoselenophenone of formula III. The compound of formula III is further reacted with chlorinating agents such as thionyl chloride or phosphorous oxychloride in presence of DMF or a base gives chloropyrimidinoselenophene of formula IV. The compound of formula IV is reacted with unsubstituted or substituted aromatic amino compounds in a protic solvent such as isopropyl alcohol, ethanol, DMF and optionally in presence of a base, to yield a compound of formula I. The base may be organic or inorganic, such as pyridine, triethylamine, sodium hydroxide etc.

Alternatively, the compounds of formula (I) in which one of X or Y or Z is selenium and others are carbons such that the resulting is fused selenophene ring, and A is N; B is NR⁵, can be made by as shown in scheme B:

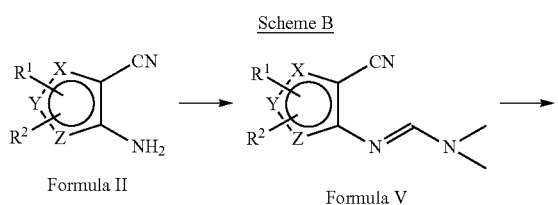

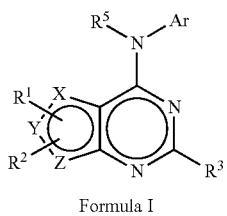

As an alternative to the procedure depicted in Scheme A, aminoselenophenecarbonitrile of formula II is reacted with dimethylformamide-dimethylacetal (Chandregowda, V.; Rao, G. V.; Reddy, G. C. Org. Proc. Res. Dev., 2007, 11, 813-816) to obtain [(dimethylamino)methylidene]amino-substituted compound of formula V, which is subsequently cyclized with optionally substituted aromatic amino compounds in a solvent, such as toluene, acetonitrile, acetic acid or a mixture thereof to obtain a compound of formula I as shown in scheme B.

Alternatively, the compounds of formula (I) in which one of X or Y or Z is selenium and others are carbons such that the resulting is fused selenophene ring, and A is N; B is NR⁵, can be synthesized by as shown in scheme C:

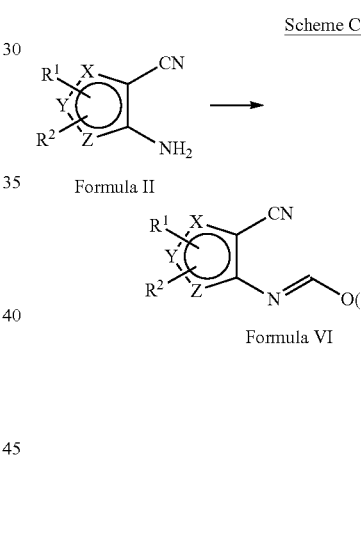

As an alternative to the procedures depicted in Schemes A and B, aminoselenophenecarbonitrile of formula II is reacted with triethyl orthoformate (or trimethyl orthoformate) to obtain compound of formula VI, which is subsequently cyclized with optionally substituted aromatic amino compounds in a solvent, such as toluene, acetonitrile, acetic acid or a mixture thereof to obtain a compound of formula I as shown in scheme C.

The synthetic process of some of the compounds of formula (I) is demonstrated as shown below.

The synthesis of 4-(arylamino)selenophenopyrimidine compounds of formula (I), more specifically the synthesis of (3-chloro-4-fluorophenyl)-6,7,8,9-tetrahydrobenzo[1,2-d]pyrimidino[5,6-b]selenophenylamine is achieved by the steps shown in scheme D.

Scheme D

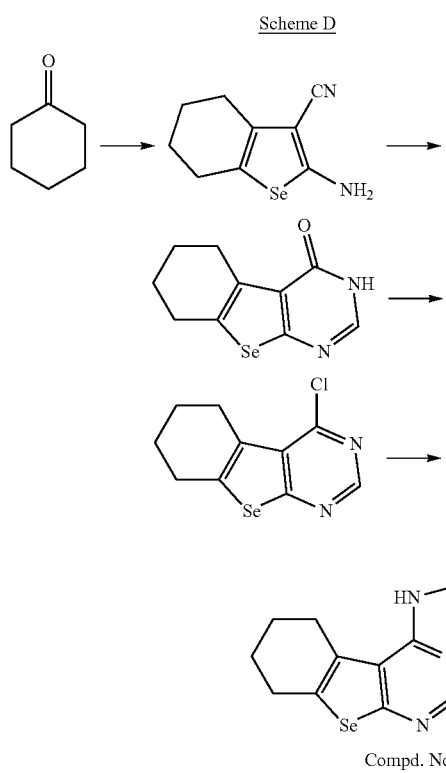

Compd. No. 1

As shown in scheme D, cyclohexanone is reacted with malononitrile and selenium powder in the presence of diethylamine to give 2-amino-4,5,6,7-tetrahydrobenzo[1,2-b]selenophene-3-carbonitrile (Abdel-Hafez, Sh. H. Russian J. Org. Chem., 2005, 41, 396-401), which on cyclization using formic acid/sulfuric acid gave 3,5,6,7,8-pentahydrobenzo[1,2-b]pyrimidino[5,4-d]selenophen-4-one. Treatment of this compound with thionyl chloride in presence of catalytic amount of DMF gave 4-chloroderivative. The 4-chlorocompound is finally reacted with 3-chloro-4-fluoroaniline to give compound No. 1.

The synthesis of 4-(arylamino)selenophenopyrimidine compounds of formula (I), more specifically the synthesis of compounds No. 2-11 is achieved by the steps shown in scheme E.

Scheme E

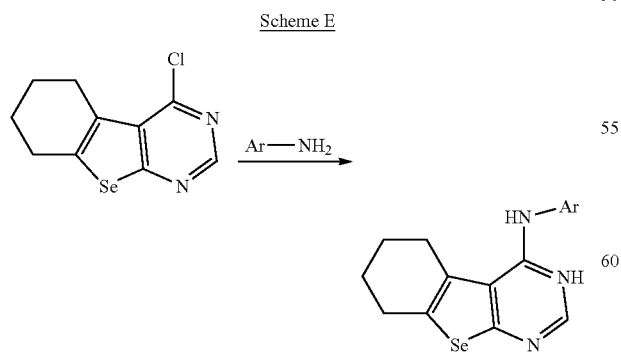

Accordingly, 4-chlorocompound (cf. scheme D) is reacted with heteroaryl amines (Matsuda, T.; Yamagata, K.; Tomioka, Y.; Yamazaki, M. Chem. Pharm. Bull., 1985, 33, 937-943; Thomae, D.; Perspicace, E.; Hesse, S.; Kirsch, G.; Seek, P. Tetrahedron, 2008, 64, 9309-9314; DellErba, C.; Spinelli, D. Tetrahedron, 1965, 21, 1061-1066) in presence of a solvent to give compounds No. 2-11. Using this process, the following compounds were synthesized.

| Compd. | Chemical structure |
|---|---|
| 2 | ![structure with Br-pyridine] |
| 3 | ![structure with 2,6-dichloropyridine] |
| 4 | ![structure with 2,6-dichloropyrimidine] |
| 5 | ![structure with pyrazine] |
| 6 | ![structure with 2,5-dibromothiophene] |

-continued

| Compd. | Chemical structure |
|---|---|
| 7 | 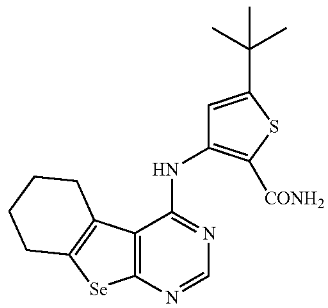 [SMILES: CC(C)(C)c1cc(Nc2ncnc3[se]c4c(c23)CCCC4)c(C(N)=O)s1] |
| 8 | 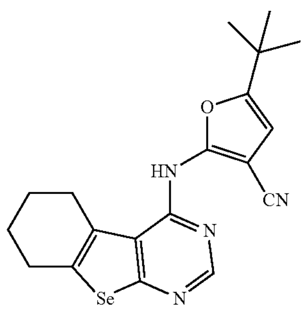 [SMILES: CC(C)(C)c1cc(C#N)c(Nc2ncnc3[se]c4c(c23)CCCC4)o1] |
| 9 | 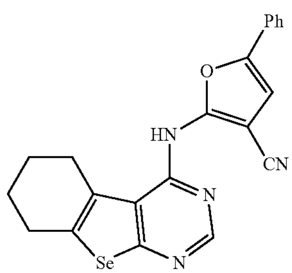 [SMILES: N#Cc1cc(-c2ccccc2)oc1Nc1ncnc2[se]c3c(c12)CCCC3] |
| 10 | 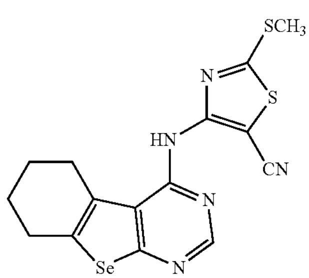 [SMILES: CSc1nc(Nc2ncnc3[se]c4c(c23)CCCC4)c(C#N)s1] |
| 11 | 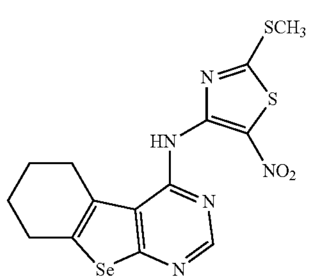 [SMILES: CSc1nc(Nc2ncnc3[se]c4c(c23)CCCC4)c([N+](=O)[O-])s1] |

The synthesis of 4-(arylamino)selenophenopyrimidine compounds of formula (I), more specifically the synthesis of compound No. 12 is achieved by the steps shown in scheme F.

Scheme F

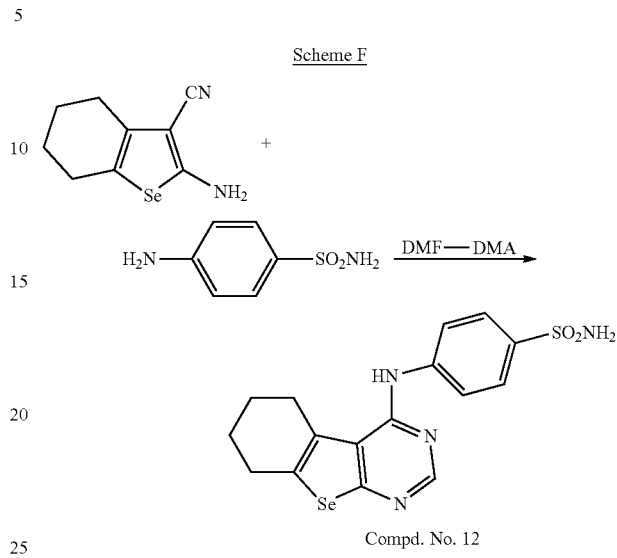

Compd. No. 12

As shown in scheme F, 2-amino-4,5,6,7-tetrahydrobenzo[b]selenophene-3-carbonitrile (cf. scheme D) is reacted with dimethylformamide-dimethylacetal (DMF-DMA) in presence of acetic acid and further reacted with sulfonamide to give the compound No. 12.

The synthesis of 4-(arylamino)selenophenopyrimidine compounds of formula (I), more specifically the synthesis of compounds No. 13-17 is achieved by the steps shown in scheme G.

Scheme G

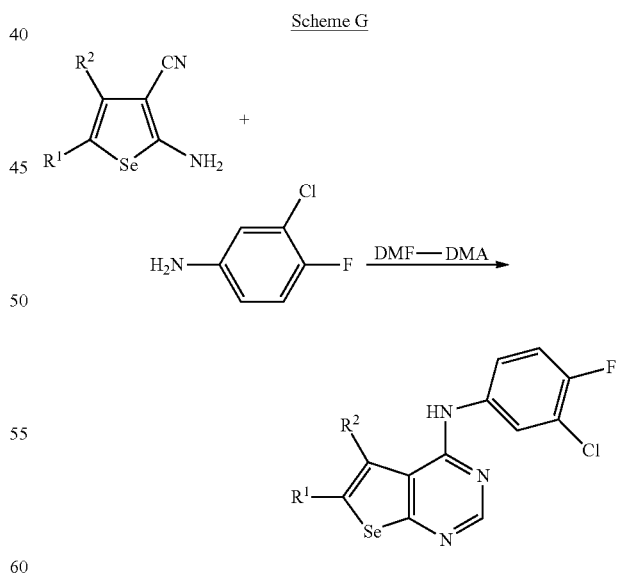

As shown in scheme G, 2-aminoselenophene-3-carbonitrile is reacted with dimethylformamide-dimethylacetal (DMF-DMA) in presence of acetic acid and further reacted with 3-chloro-4-fluoroaniline to give compounds No. 13-17. Using this process, the following compounds were synthesized.

| Compd. | Chemical structure |
|---|---|
| 13 | 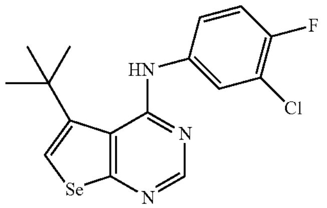 [SMILES: CC(C)(C)c1c[se]c2ncnc(Nc3ccc(F)c(Cl)c3)c12] |
| 14 | 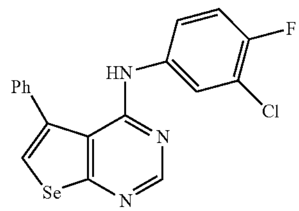 [SMILES: Fc1ccc(Nc2ncnc3[se]cc(-c4ccccc4)c23)cc1Cl] |
| 15 | 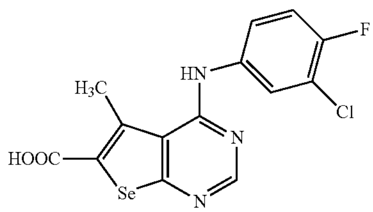 [SMILES: Cc1c(C(=O)O)[se]c2ncnc(Nc3ccc(F)c(Cl)c3)c12] |
| 16 | 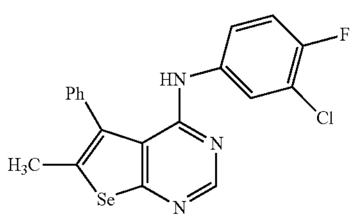 [SMILES: Cc1[se]c2ncnc(Nc3ccc(F)c(Cl)c3)c2c1-c1ccccc1] |
| 17 | 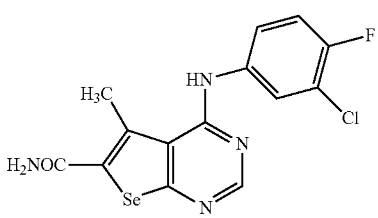 [SMILES: Cc1c(C(N)=O)[se]c2ncnc(Nc3ccc(F)c(Cl)c3)c12] |

The synthesis of 4-(arylamino)selenophenopyrimidine compounds of formula (I), more specifically the synthesis of compound No. 18 and compound No. 19 is achieved by the steps shown in scheme H.

Scheme H

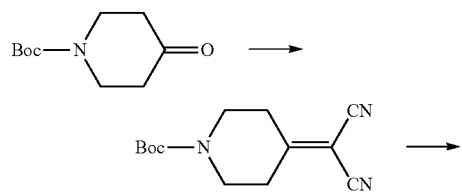

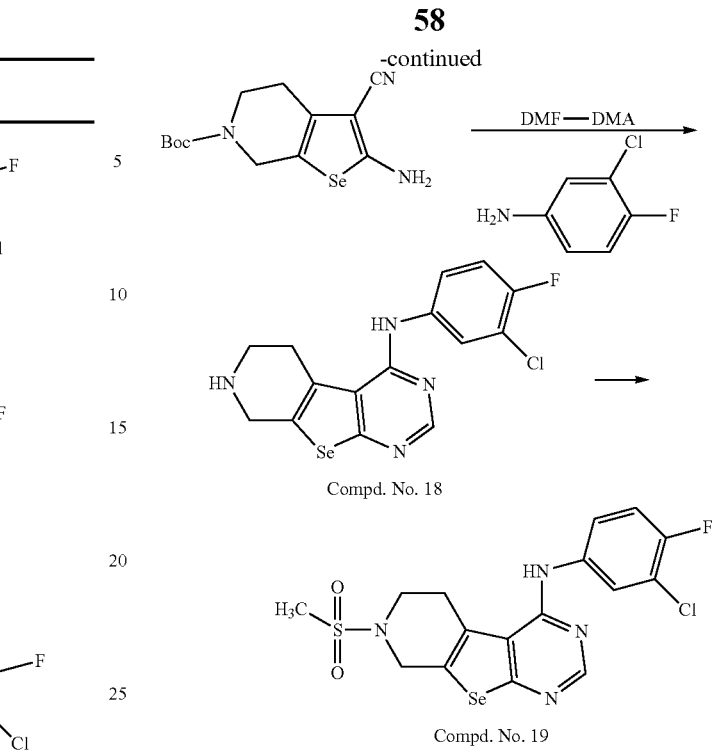

As shown in scheme H, treatment of 4-piperidinone hydrochloride monohydrate with BOC anhydride gave BOC protected compound (Wang, X.-S.; Wu, J.-R.; Zhou, J.; Tu, S.-J. J. Comb. Chem., 2009, 11, 1011-1022), which on reaction with malononitrile and selenium powder in presence of diethylamine provided BOC protected 2-amino-4,5,6,7-tetrahydroselenopheno[2,3-c]pyridine-3-carbonitrile in good yield. This selenophene compound is reacted with dimethylformamide-dimethylacetal in presence of acetic acid and further reaction with 3-chloro-4-fluoroaniline gave compound No. 18. Treatment of compound No. 18 with methanesulfonyl chloride in presence of a base provided compound No. 19.

The synthesis of 4-(arylamino)selenophenopyrimidine compounds of formula (I), more specifically the synthesis of compounds No. 20-23 is achieved by the steps shown in scheme I.

Scheme I

As shown in scheme I, treatment of BOC protected 2-amino-4,5,6,7-tetrahydroselenopheno[2,3-c]pyridine-3-carbonitrile (cf. Scheme H) with dimethylformamide-dimethylacetal in presence of acetic acid and further reaction with arylamines (Tsubou, S.; Mimura, S.; Ono, S.-I.; Watanabe, K.; Takeda, A. Bull. Chem. Soc. Jpn., 1987, 60, 1807-1812) gave compounds No. 20-23. Using this process, the following compounds were synthesized.

| Compd. | Chemical structure |
|---|---|
| 20 | 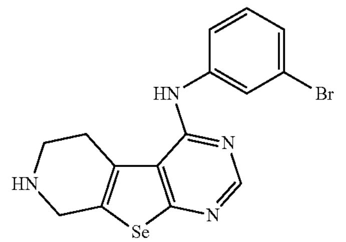 [SMILES: Brc1cccc(Nc2ncnc3[se]c4c(c23)CCNC4)c1] |
| 21 | 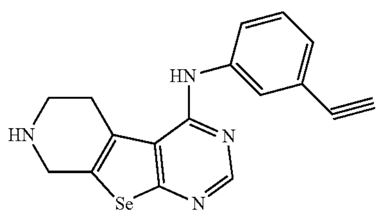 [SMILES: C#Cc1cccc(Nc2ncnc3[se]c4c(c23)CCNC4)c1] |
| 22 | 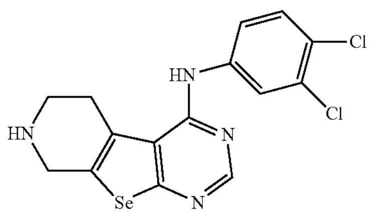 [SMILES: Clc1ccc(Nc2ncnc3[se]c4c(c23)CCNC4)cc1Cl] |
| 23 | 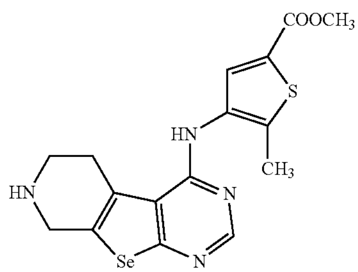 [SMILES: COC(=O)c1cc(Nc2ncnc3[se]c4c(c23)CCNC4)c(C)s1] |

The synthesis of 4-(arylamino)selenophenopyrimidine compounds of formula (I), more specifically the synthesis of compounds No. 24-25 is achieved by the steps shown in scheme J.

Scheme J

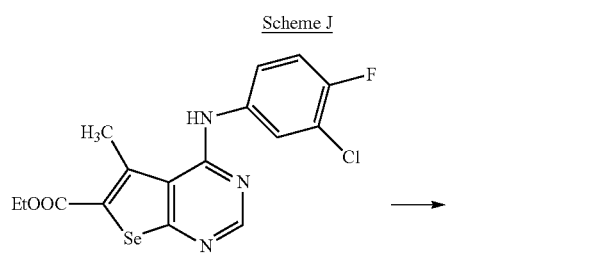
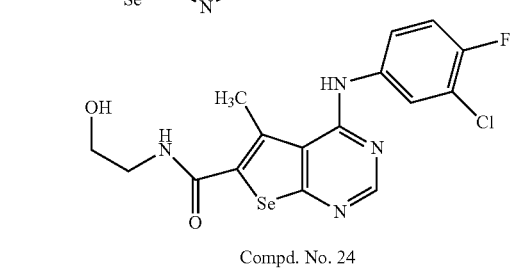

Compd. No. 24

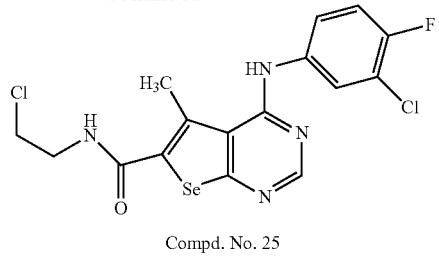

Compd. No. 25

As shown in scheme J, treatment of ethyl 4-[3-chloro-4-fluorophenyl)amino]-5-methylselenopheno[2,3-d]pyrimidine-6-carboxylate (ethyl ester of compound 15) with ethanolamine gave compd. No. 24 in good yield. Compd. No. 24 is reacted with thionyl chloride to provide compound No. 25.

The synthesis of 4-(arylamino)selenophenopyrimidine compounds of formula (I), more specifically the synthesis of compound No. 26 is achieved by the steps shown in scheme K.

Scheme K

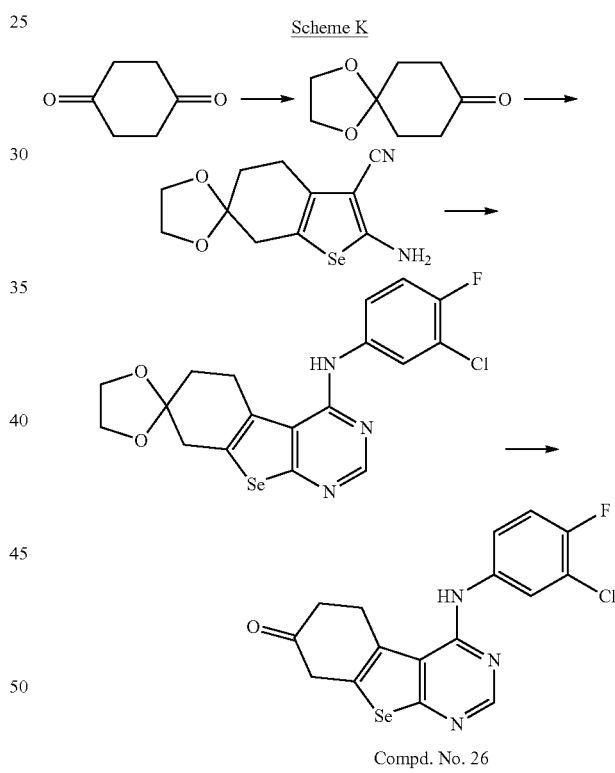

Compd. No. 26

As shown in scheme K, cyclohexane-1,4-dione is mono-protected with ethanediol in presence of p-toluenesulfonic acid (available in Sigma-Aldrich), which is reacted with malononitrile and selenium powder in presence of diethylamine provided 7-aminospiro[1,3-dioxolane-2,6'-4,5,6,7-tetrahydrobenzo[2,1-b]selenophene]-8-carbonitrile. This selenophene compound is reacted with DMF-DMA in presence of acetic acid and further reaction with 3-chloro-4-fluoroaniline followed by acid hydrolysis gave compound No. 26.

The synthesis of 4-(arylamino)selenophenopyrimidine compounds of formula (I), more specifically the synthesis of compound No. 27 is achieved by the steps shown in scheme L.

Scheme L

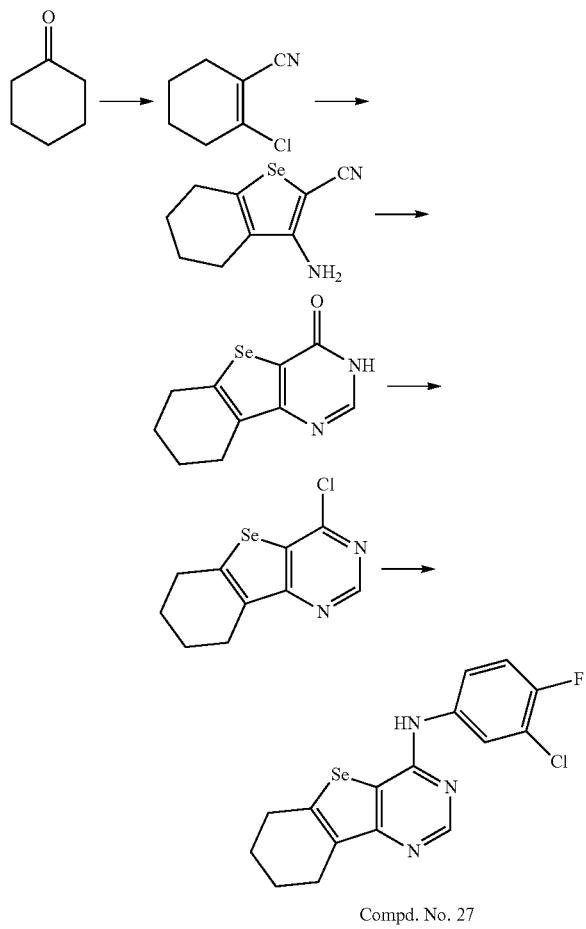

Compd. No. 27

As shown in scheme L, reaction of cyclohenxanone with dimethylformamide-phosphorous oxychloride and further reaction with hydroxylamine hydrochloride gave 2-chlorocyclohex-1-enecarbonitrile (Gunes, Y.; Polat, M. F.; Sahin, E.; Fleming, F. F.; Altundas, R. J. Org. Chem., 2010, 75, 7092-7098), which is further reacted with sodium selenide/chloroacetonitrile and sodium methoxide to give 3-amino-4,5,6,7-tetrahydrobenzo[1,2-b]selenophene-2-carbonitrile. Cyclisation of this selenophene compound with formic acid/sulfuric acid and further reaction with thionyl chloride gave 4-chloro-6,7,8,9-tetrahydrobenzo[1,2-d]pyrimidino[5,4-b] selenophene. Reaction of 4-chloroselenophene compound with 3-chloro-4-fluoroaniline in presence of isopropanol gave compound No. 27.

The synthesis of 4-(arylamino)selenophenopyrimidine compounds of formula (I), more specifically the synthesis of compounds No. 28-29 is achieved by the steps shown in scheme M.

Scheme M

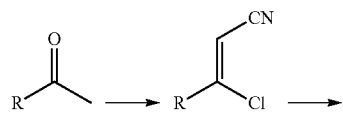

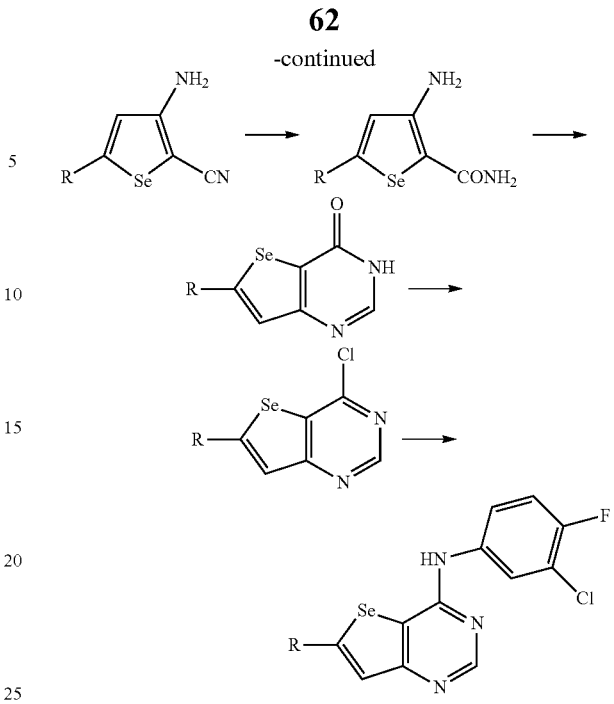

As shown in scheme M, reaction of carbonyl compound with dimethylformamide-phosphorous oxychloride and further reaction with hydroxylamine hydrochloride gave 3-chloro3-substitutedcarbonitrile derivative (Ohta, H.; Ishizaka, T.; Tatsuzuki, M.; Yoshinaga, M.; Iida, I.; Yamaguchi, T.; Tomishima, Y.; Futaki, N.; Toda, Y.; Saito, S. Bioorg. Med. Chem., 2008, 16, 1111-1124), which on further reaction with sodium selenide/chloroacetonitrile and sodium methoxide gave 3-aminoselenophene-2-carbonitrile derivative (Thomae, D.; Kirsch, G.; Seck, P. Synthesis, 2008, 1600-1606). Cyclisation of this selenophene compound with formic acid/sulfuric acid and further reaction with thionyl chloride gave 4-chloropyrimidinoselenophene derivative (Hesse, S.; Chenet, C.; Thomae, D.; Kirsch, G. Synthesis, 2009, 1204-1208). Reaction of 4-chloroselenophene compound with 3-chloro-4-fluoroaniline in presence of isopropanol gave compounds No. 28-29. Using this process, the following compounds were synthesized.

| Compd. | Chemical structure |
| --- | --- |
| 28 | ![structure with tert-butyl group] |
| 29 | ![structure with Ph group] |

The synthesis of 4-(arylamino)selenophenopyrimidine compounds of formula (I), more specifically the synthesis of compounds No. 30-31 is achieved by the steps shown in scheme N.

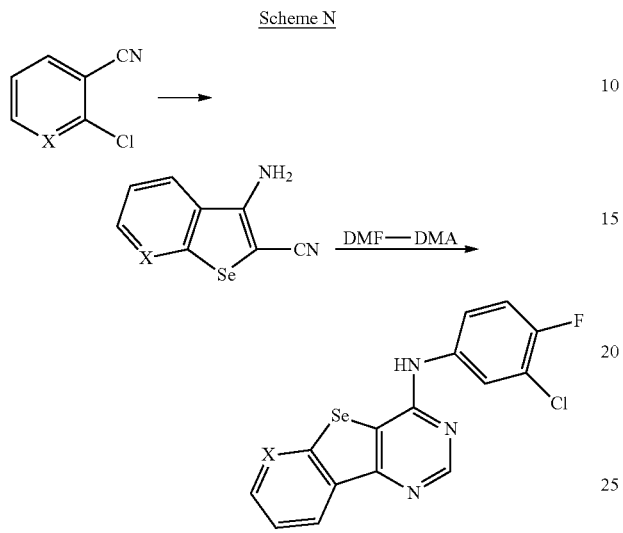

Scheme N

As shown in scheme N, reaction of 2-chlorobenzonitrile (X=CH) or 2-chloropyridine-3-carbonitrile (X=N) with sodium selenide/chloroacetonitrile and sodium methoxide gave 3-aminoselenophene-2-carbonitrile derivatives. These selenophene derivatives are reacted with dimethylformamide-dimethylacetal in presence of acetic acid and further reacted with 3-chloro-4-fluoroaniline to give compounds No. 30-31. Using this process, the following compounds were synthesized.

| Compd. | Chemical structure |
|---|---|
| 30 | 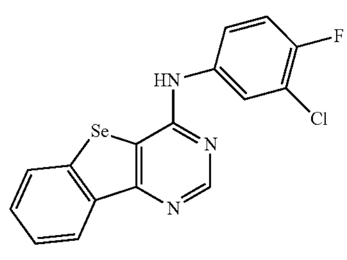 [SMILES: Fc1ccc(Nc2ncnc3c2[se]c2ccccc23)cc1Cl] |
| 31 | 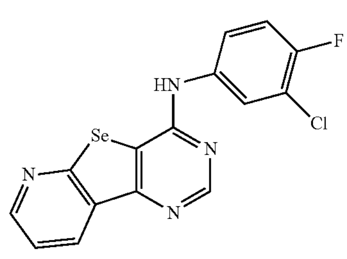 [SMILES: Fc1ccc(Nc2ncnc3c2[se]c2ncccc23)cc1Cl] |

The synthesis of 4-(arylamino)selenophenopyrimidine compounds of formula (I), more specifically the synthesis of compound No. 32 is achieved by the steps shown in scheme O.

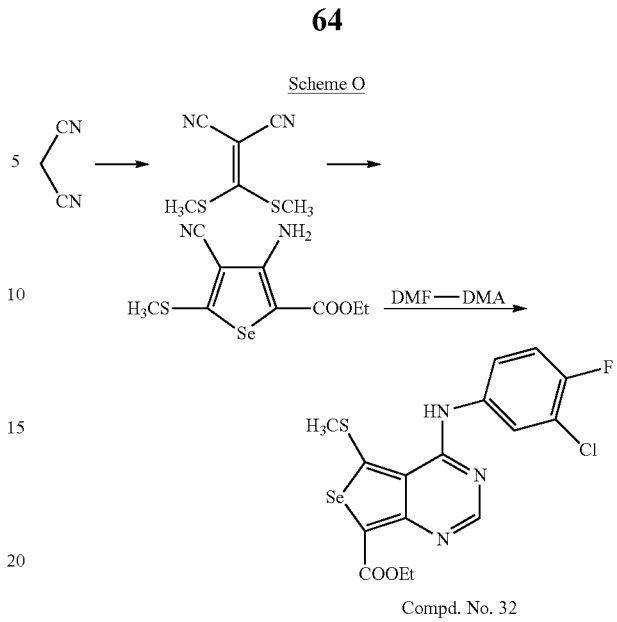

Scheme O

Compd. No. 32

As shown in scheme O, reaction of malononitrile with carbon disulfide in the presence of sodium hydroxide and followed by reaction with dimethyl sulfate gave (bismethylthiomethylene)malononitrile (Baraldi, P. G.; Fruttarolo, F.; Tabrizi, M. A.; Preti, D.; Romagnoli, R.; El-Kashef, H.; Moorman, A.; Varani, K.; Gessi, S.; Merighi, S.; Borea, P. A. J. Med. Chem., 2003, 46, 1229-1241; Thomae, D.; Perspicace, E.; Henryon, D.; Xu, Z.; Schneider, S.; Hesse, S.; Kirsch, G.; Seck, P. Tetrahedron, 2009, 65, 10453-10458). The dicarbonitrile is reacted with sodium selenide/ethyl chloroacetate to give ethyl 3-amino-4-cyano-5-methylthioselenophene-2-carboxylate. This selenophene derivative on reaction with dimethylformamide-dimethylacetal in presence of acetic acid and further reaction with 3-chloro-4-fluoroaniline gave compound No. 32.

The synthesis of 4-(arylamino)selenophenopyrimidine compounds of formula (I), more specifically the synthesis of compound No. 33 is achieved by the steps shown in scheme P.

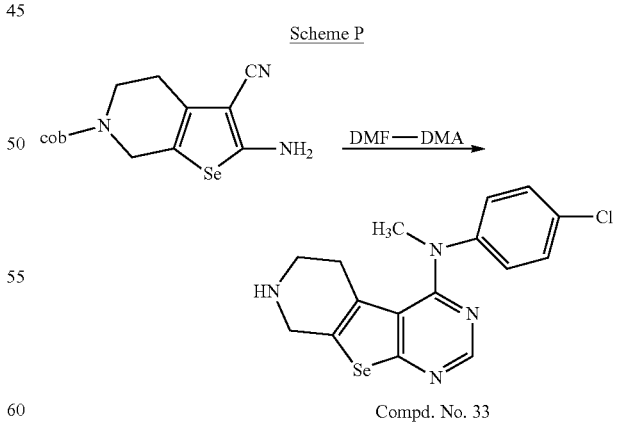

Scheme P

Compd. No. 33

As shown in scheme P, N-Boc-2-amino-4,5,6,7-tetrahydroselenopheno[2,3-c]pyridine-3-carbonitrile (cf scheme H) is reacted with dimethylformamide-dimethylacetal in presence of acetic acid and further reacted with 4-chloro-N-methylaniline to give compound No. 33.

Synthesis of 2-Substituted Compounds:

The synthesis of 4-(arylamino)selenophenopyrimidine compounds of formula (I), more specifically the synthesis of compound No. 34 is achieved by the steps shown in scheme Q.

Scheme Q

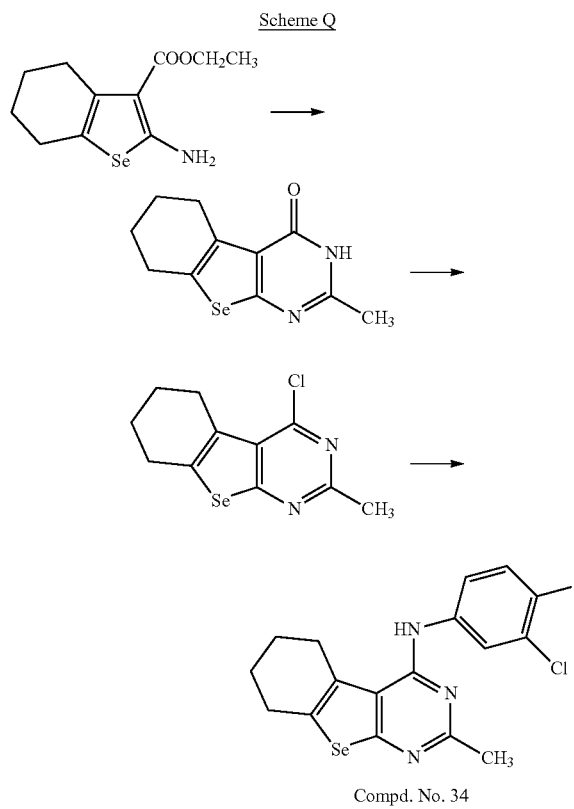

Compd. No. 34

As shown in scheme Q, reaction of ethyl 2-amino-4,5,6,7-tetrahydrobenzo[1,2-b]selenophene-3-carboxylate (Aumann, K. M.; Scammells, P. J.; White, J. M.; Schiesser, C. H. Org. Biomol. Chem., 2007, 5, 1276-1281) with acetonitirle in presence of HCl gave cyclised product, which on further reaction with phosphorous oxychloride gave 4-chlorocompound. 4-Chlorocompound is refluxed with 3-chloro-4-fluoroaniline in isopropyl alcohol to give (3-chloro-4-fluorophenyl)(2-methyl(5,6,7,8-tetrahydrobenzo[1,2-b]pyrimidino[5,6-d]selenophen-4-yl)amine.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of formula (I)" is meant to include the simultaneous treatment of more than one disease as well as the administration of more than one compound of formula (I).

Compositions

In another aspect, the disclosure provides pharmaceutical compositions comprising a compound of formula (I) or a pharmaceutically acceptable salt or solvates or hydrates or stereoisomers thereof in combination with a pharmaceutically acceptable excipient(s) or carrier(s) or diluent(s);

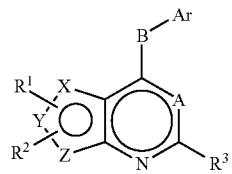

Formula (I)

wherein all the groups are as defined earlier.

The pharmaceutical compositions comprising a compound of general formula (I) or a pharmaceutically acceptable salt or solvates or hydrate or stereoisomers thereof in combination with a pharmaceutically acceptable excipient(s) or carrier(s) or diluent(s); and the concentration of said compound of general formula (I) is in the range of 0.01% to 99%.

The pharmaceutical compositions comprising a compound of general formula (I) or a pharmaceutically acceptable salt or solvates or hydrates or stereoisomers thereof in combination with a pharmaceutically acceptable excipient(s) or carrier(s) or diluent(s); the said carriers or diluents or excipients are wherein preferred examples of solid carriers or diluents or excipients include but not limited to glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors and preservatives and preferred examples of liquid carriers or diluents or excipients include but not limited to distilled water, saline, aqueous glucose solution, alcohol (e.g. ethanol), propylene glycol and polyethylene glycol; and oily carriers such as various animal and vegetable oils, white soft paraffin, paraffin and wax.

When the compounds of the present disclosure are administered as pharmaceuticals, to humans and animals, they can be given per se or as a pharmaceutical composition containing, for example, 0.01 to 99% of a compound of formula (I) in combination with a pharmaceutically acceptable carrier or diluent.

In still another aspect, the disclosure provides a process for preparing a pharmaceutical composition. The process includes the step of comprising combining at least one compound of formula (I) as defined above with at least one pharmaceutically acceptable carrier or diluent, and bringing the resulting combination into a suitable administration form.

In another aspect, the pharmaceutical compositions of the present disclosure may be in any form which allows for the composition to be administered to a subject. For example, the composition may be in the form of a solid, liquid or gas (aerosol). Typical routes of administration include, without limitation, topical, parenteral, sublingual, intraperitoneal (IP), intravenous (IV), oral (PO), intramuscular (IM), intracutaneous (IC), intradermal (ID), intrauterine and intrarectal. The term parenteral as used herein includes subcutaneous injections, intravenous, intramuscular, intrasternal injection or infusion techniques. Pharmaceutical compositions compounds disclosed herein are formulated so as to allow the active ingredients contained therein to be bioavailable upon administration of the composition to a subject. Compositions that will be administered take the form of one or more dosage units, for example, a tablet may be a single dosage unit, and a container of formula (I) compound in topical form may hold a plurality of dosage units and also in the form of nanoparticles of different sizes in an emulsion to a warm blooded animal, in need thereof.

It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In another aspect, the disclosure provides the pharmaceutical compositions comprising at least one compound of formula (I) or a pharmaceutically acceptable salt or solvates or hydrates or stereoisomers thereof and at least one selected from pharmaceutically acceptable excipient, pharmaceutically acceptable diluent, and pharmaceutically acceptable carrier, and optionally further comprising at least one anti-tumor agent.

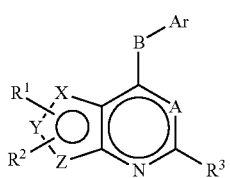

Formula (I)

wherein all the groups are as defined earlier.

The anti-tumor agent is selected from the group consisting of Alkylating agents, Anti-metabolites, Hormonal therapy agents, Cytotoxic topoisomerase inhibiting agents, Anti-angiogenic compounds, Antibodies, VEGF inhibitors, EGFR (HER1) inhibitors, HER2 inhibitors, CDK inhibitors, Proteasome inhibitors, Serine/threonine kinase (Raf inhibitors), Tyrosine kinase inhibitors, Androgen receptor antagonists and Aromatase inhibitors. In this regard, the following is a non-limiting list of examples of secondary agents that may be used in combination with the compounds of the present disclosure:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, mitolactol, cisplatin, carboplatin, eptaplatin, lobaplatin, nedaplatin, oxaliplatin, and satraplatin.

Anti-metabolites include, but are not limited to, methotrexate, 6-mercaptopurineriboside, mercaptopurine, 5-fluorouracil, tegafur, doxifluridine, carmofur, cytarabine, cytarabine ocfosfate, enocitabine, gemcitabine, fludarabine, 5-azacitidine, capecitabine, cladribine, clofarabine, decitabine, eflornithine, ethynylcytidine, cytosine arabinoside, hydroxyurea, melphalan, nelarabine, nolatrexed, ocfosfate, disodium pemetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, abiraterone acetate, finasteride, episteride, tamoxifen citrate, fulvestrant, Trelstar, toremifene, raloxifene, lasofoxifene, letrozole, sagopilone, ixabepilone, epothilone B, vinblastine, vinflunine, docetaxel, and paclitaxel; Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide;

Anti-angiogenic compounds include, but are not limited to, acitretin, aflibercept, angiostatin, aplidine, asentar, axitinib, recentin, bevacizumab, brivanib alaninate, cilengitide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin.

Antibodies include, but are not limited to, trastuzumab, cetuximab, bevacizumab, rituximab, ticilimumab, ipilimumab, lumiliximab, catumaxomab, atacicept, oregovomab, and alemtuzumab.

VEGF inhibitor is selected from sorafenib, DAST, bevacizumab, sunitinib, recentin, axitinib, aflibercept, telatinib, brivanib alaninate, vatalanib, pazopanib, and ranibizumab.

EGFR (HER1) inhibitor is selected from cetuximab, panitumumab, vectibix, gefitinib, erlotinib, and Zactima;

HER2 inhibitor is selected from lapatinib, trastuzumab, and pertuzumab;

CDK inhibitor is selected from roscovitine and flavopiridol;

Proteasome inhibitor is selected from bortezomib and carfilzomib;

Serine/threonine kinase inhibitors including MEK inhibitors and Raf inhibitors such as sorafenib;

Tyrosine kinase inhibitor is selected from dasatinib, nilotinib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab and pertuzumab.

Androgen receptor antagonist is selected from nandrolone decanoate, fluoxymesterone, Android, Prostaid, andromustine, bicalutamide, flutamide, apo-cyproterone, apoflutamide, chlormadinone acetate, Androcur, Tabi, cyproterone acetate, and nilutamide.

Aromatase inhibitor is selected from anastrozole, letrozole, testolactone, exemestane, aminoglutethimide, and formestane.

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazarotene, velcade, gallium nitrate, canfosfamide, darinaparsin, and tretinoin. In a preferred embodiment, the compounds of the present disclosure may be used in combination with chemotherapy (i.e. cytotoxic agents), anti-hormones and/or targeted therapies such as other kinase inhibitors, mTOR inhibitors and angiogenesis inhibitors.

The compounds of the present invention may also be employed in cancer treatment in conjunction with radiation therapy and/or surgical intervention. Furthermore, the compounds of formula (I) may be utilized, as such or in compositions, in research and diagnostics, or as analytical reference standards, and the like, which are well known in the art.

In still another aspect, the disclosure provides use of a compound of formula (I) as defined above for manufacturing a pharmaceutical composition for the treatment or inhibition or control of a cell proliferative disorder. In certain embodiments, the cell proliferative disorder is cancer.

Regardless of the route of administration selected, the compounds of the disclosure, which may be used in a suitable hydrated form, and/or the pharmaceutical compositions of the present disclosure, are formulated into pharmaceutically acceptable dosage forms by conventional methods known to those of skill in the art.

Actual dosage levels and time course of administration of the active ingredients in the pharmaceutical compositions of the disclosure may be varied so as to obtain an amount of the active ingredient which is effective to achieve the desired therapeutic response for a particular patient, composition, and mode of administration, without being toxic to the patient. An exemplary dose range is from 0.01 to 100 mg/kg per day or 0.1 to 150 mg/kg per day.

In certain embodiments, the compound of the disclosure can be used in combination therapy with conventional cancer chemotherapeutics. Conventional treatment regimens for leukemia and for other tumors include radiation, drugs, or a combination of both.

Methods of Use

The compounds of the present disclosure may be used to inhibit the activity of tyrosine kinases, particularly including HER1 (EGFR), HER2 and VEGF or to kill cancer cells. Therefore, the compounds of formula (I) are expected to be valuable as therapeutic agents. Accordingly, the present disclosure provides a method of treating or inhibiting or controlling a cell proliferative disorder in a patient in need of such treatment, comprising administering to the patient an effective amount of a compound of formula (I), or its pharmaceutical salt; or isomers or hydrates or solvates thereof;

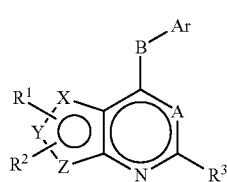

Formula (I)

wherein
X is selenium, Y and Z are carbons; or
Y is selenium, X and Z are carbons; or
Z is selenium, X and Y are carbons;
A is N or C—$R^4$, wherein $R^4$ is selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy-$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino-$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl;
B is selected from S, S(O), S($O_2$) or $NR^5$; wherein $R^5$ is selected from hydrogen, alkyl, alkoxy or haloalkyl;
Ar is aryl or heteroaryl ring; the aryl is benzene ring or napthhalene ring and heteroaryl is 6-membered aromatic ring containing one, two or three nitrogen atoms; or the heteroaryl is 5-membered aromatic ring containing one or more heteroatoms selected from sulfur, oxygen, and nitrogen, with proviso that no more than one oxygen or sulfur atom is present; such rings include pyridine, pyridazine, pyrazine, pyrimidine, thiophene, furan, pyrrole, pyrazole, imidazole, oxazole, isoxazole, thiazole and isothiazole;
Ar ring is optionally substituted by one, two or more groups independently selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino-$C_{1-6}$alkoxy, $C_{1-6}$alkylamino $C_{1-6}$alkyl, di($C_{1-6}$alkyl)amino$C_{1-6}$alkyl, $C_{1-6}$alkylsulfinyl, $C_{1-6}$alkylsulfonyl, and a aryl, heteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxy-carbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino-$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl;
$R^1$, $R^2$, and $R^3$
are independently selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkyl-carbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino $C_{1-6}$alkyl, di($C_{1-6}$alkyl)amino$C_{1-6}$alkyl, $C_{1-6}$alkylsulfinyl, $C_{1-6}$alkylsulfonyl, and a aryl, heteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkyl-aminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkyl-amino$C_{1-6}$alkyl, di($C_{1-6}$alkyl)amino $C_{1-6}$alkyl, $C_{1-6}$alkylsulfinyl, $C_{1-6}$alkylsulfonyl; or
$R^1$, and $R^2$
is independently selected from the following formula;

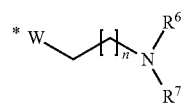

wherein n is an integer selected from 0, 1 to 5; preferably 2; * indicates the point of attachment to the selenophene ring in formula I; W is selected from $CH_2$, O, S, or NH; $R^6$ and $R^7$ is independently selected from hydrogen, amino, trihalomethyl, $C_{1-6}$alkyl, $C_{1-6}$secondaryalkyl, $C_{1-6}$tertiaryalkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{1-6}$alkylamino, di(C$_{1-6}$alkyl)amino, aminoC$_{1-6}$alkyl, aminoC$_{1-6}$alkoxy, C$_{1-6}$alkylamino C$_{1-6}$alkyl, di(C$_{1-6}$alkyl)aminoC$_{1-6}$alkyl; or R$^1$ and R$^2$ are joined, and taken together with the atoms to which they are attached, form a 5- to 7-membered optionally substituted carbocyclic or perhydroheterocyclic ring and are selected from the formula;

wherein n is an integer selected from 0 to 4; m is an integer selected from 0 to 4; * indicates the point of attachment to the R$^1$ and R$^2$ in formula I; L is selected from CH$_2$, O, S and NR$^8$; where in R$^8$ is selected from hydrogen, amino, trihalomethyl, C$_{1-6}$alkyl, C$_{1-6}$secondaryalkyl, C$_{1-6}$tertiaryalkyl, C$_{2-6}$alkenyl, C$_{2-6}$alkynyl, C$_{1-4}$alkylcarbonyl, C$_{1-4}$alkoxycarbonyl, aminocarbonyl, C$_{1-6}$alkylaminocarbonyl, di(C$_{1-6}$alkyl)aminocarbonyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{1-6}$alkylamino, di(C$_{1-6}$alkyl)amino, aminoC$_{1-6}$alkyl, aminoC$_{1-6}$alkoxy, C$_{1-6}$alkylamino C$_{1-6}$alkyl, di(C$_{1-6}$alkyl)aminoC$_{1-6}$alkyl;

or R$^8$ is selected from the following formula;

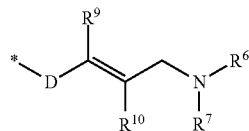

* indicates the point of attachment to N in NR$^8$; wherein D is selected from C$_{1-6}$alkyl, —C(═O), —S(═O), —S(═O)$_2$; R$^9$ and R$^{10}$ is selected from hydrogen, halogen, hydroxy, formyl, carboxylic acid, amino, nitro, cyano, sulfonic acid, thiole, trihalomethyl, sulfonamide, C$_{1-6}$alkyl, C$_{1-6}$secondaryalkyl, C$_{1-6}$tertiaryalkyl, C$_{2-6}$alkenyl, C$_{2-6}$alkynyl, C$_{1-4}$alkylcarbonyl, C$_{1-4}$alkoxycarbonyl, aminocarbonyl, C$_{1-6}$alkyl-aminocarbonyl, di(C$_{1-6}$alkyl)aminocarbonyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{1-6}$alkylamino, di(C$_{1-6}$alkyl)amino, aminoC$_{1-6}$alkyl, aminoC$_{1-6}$alkoxy, C$_{1-6}$alkyl-amino C$_{1-6}$alkyl, di(C$_{1-6}$alkyl)aminoC$_{1-6}$alkyl, C$_{1-6}$alkylsulfinyl, C$_{1-6}$alkylsulfonyl; or R$^6$ and R$^7$ are joined, and taken together with the atoms to which they are attached, form a 5- to 7-membered optionally substituted cycloalkyl or cycloheteroalkyl ring; or R$^1$ and R$^2$ are joined, and taken together with the atoms to which they are attached, form optionally substituted aryl or optionally substituted heteroaryl ring fused with selenophene; aryl is benzene ring and heteroaryl is 6-membered aromatic ring containing one, two or three nitrogen atoms; or the heteroaryl is 5-membered aromatic ring containing one or more heteroatoms selected from sulfur, oxygen, and nitrogen, with proviso that no more than one oxygen or sulfur atom is present; such rings include pyridine, pyridazine, pyrazine, pyrimidine, thiophene, furan, pyrrole, pyrazole, imidazole, oxazole, isoxazole, thiazole and isothiazole.

Another aspect of the disclosure provides a method of treating or inhibiting or controlling a cell proliferative disorder in a patient in need of such treatment, comprising administering to the patient an effective amount of a composition comprising at least one selenophene compound of formula (I), or its pharmaceutical salt; or isomers or hydrates or solvates thereof; and at least one selected from pharmaceutically acceptable excipient, pharmaceutically acceptable diluent, and pharmaceutically acceptable carrier.

Another aspect of the disclosure provides a method of treating or inhibiting or controlling a cell proliferative disorder in a patient in need of such treatment, comprising administering to the patient an effective amount of a composition comprising at least one selenophene compound of formula (I), or its pharmaceutical salt; or isomers or hydrates or solvates thereof; and at least one selected from pharmaceutically acceptable excipient, pharmaceutically acceptable diluent, and pharmaceutically acceptable carrier and optionally further comprising at least one anti-tumor agent selected from the group consisting of Alkylating agents, Anti-metabolites, Hormonal therapy agents, Cytotoxic topoisomerase inhibiting agents, Anti-angiogenic compounds, Antibodies, VEGF inhibitors, EGFR (HER1) inhibitors, HER2 inhibitors, CDK inhibitors, Proteasome inhibitors, Serine/threonine kinase (Raf inhibitors), Tyrosine kinase inhibitors, Androgen receptor antagonists and Aromatase inhibitors.

A method of treating or inhibiting, or controlling cell proliferative disorder, wherein the said administration comprises the routes selected from the group consisting of intraperitoneal (IP), intravenous (IV), oral (PO), intramuscular (IM), intracutaneous (IC), intradermal (ID), intrauterine, intratumoral and intrarectal.

In certain embodiments, the cell proliferative disorder is cancer. The term "treating" or "treatment" as stated throughout this document is used conventionally, e.g., the management or care of a subject for the purpose of combating, alleviating, reducing, relieving, improving the condition of a disease or disorder, such as a carcinoma or any malignancy.

The term "subject" or "patient" includes organisms which are capable of suffering from a cell proliferative disorder or who could otherwise benefit from the administration of a compound of the disclosure, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "cell proliferative disorder" includes disorders involving the undesired or uncontrolled proliferation of a cell. The compounds of the present disclosure can be utilized to prevent, inhibit, block, reduce, decrease, control, etc., cell proliferation and/or cell division, and/or produce apoptosis. This method comprises administering to a subject in need thereof, including a mammal, including a human, an amount of a compound disclosed herein, or a pharmaceutically acceptable salt, isomer, polymorph, metabolite, hydrate or solvate thereof which is effective to treat or prevent the disorder. Cell proliferative or hyper-proliferative disorders in the context of this disclosure include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor. Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers. Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer, and squamous cell cancer.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present disclosure include atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present disclosure include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present disclosure may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering a compound of formula (I) or their pharmaceutical compositions of the present disclosure.

The present disclosure includes the exemplary embodiments described below, which are provided by the way of illustration only, and should not be considered to limit the scope of the invention. Variations and changes, which are obvious to one skilled in the art, are intended to be within the scope and nature of the invention, which are defined in the appended claims.

EXAMPLES

Example 1

Synthesis of (3-chloro-4-fluorophenyl)-5,6,7,8-tetrahydrobenzo[1,2-b]pyrimidino[5,6-d]selenophen-4-ylamine (compd. No. 1)

Step a 3,5,6,7,8-Pentahydrobenzo[1,2-b]pyrimidino[5,4-d]selenophen-4-one

To a solution of 2-amino-4,5,6,7-tetrahydrobenzo[1,2-b]selenophene-3-carbonitrile (5.4 g, Abdel-Hafez, Sh. H. Russian J. Org. Chem., 2005, 41, 396-401) in formic acid (50 mL) was added concentrated sulfuric acid (20 mL) dropwise for 15 min. The reaction mixture was stirred at 80-90° C. for 2 h and allowed to rt. The reaction mixture was poured into ice cooled water and stirred for 15 min. The precipitated solid was filtered, washed with water and dried to give the product as a pale brown color solid (4.5 g, 75%), mp 250-260° C. $^1$H NMR (400 MHz, DMSO-$d_6$): δ 12.32 (1H, s), 7.97 (1H, s), 2.89 (2H, m), 2.82 (2H, m), 1.77 (4H, m); LC-MS (negative ion mode): m/z 251, 253 (M−H)$^-$.

Step b

4-Chloro-5,6,7,8-tetrahydrobenzo[1,2-b]pyrimidino[5,4-d]selenophene

A mixture of step a compound (500 mg), thionyl chloride (5 mL) and catalytic amount of DMF (0.5 mL) was refluxed for 3 h. Solvents were removed under vacuum and the mixture was diluted with ice cold water. The solution was extracted with chloroform (3×100 mL) and the combined chloroform layer was washed with water, sodium bicarbonate, brine and dried over sodium sulfate. The solution was filtered and evaporated the solvent. The residue was chromatographed over silica gel column using hexane-ethyl acetate (98:2) as eluents to give the product as an off-white color solid (450 mg, 84%), mp 100-102° C. $^1$H NMR (400 MHz, CDCl$_3$): δ 8.65 (1H, s), 3.09-3.12 (2H, m), 2.94-2.98 (2H, m), 1.88-1.94 (4H, m).

Step c

(3-Chloro-4-fluorophenyl)-5,6,7,8-tetrahydrobenzo[1,2-b]pyrimidino[5,6-d]selenophen-4-ylamine To a solution of step b compound (300 mg, 1.10 mmol) in isopropyl alcohol (10 mL) was added 3-chloro-4-fluoroaniline (640 mg, 4.4 mmol) at rt and the mixture was refluxed for 7 h. The mixture was allowed to rt and the contents were poured into ice cold water. The solution was extracted with chloroform (3×100 mL) and the combined chloroform layer was washed with water, brine and dried over sodium sulfate. The solution was filtered and evaporated the solvent. The residue was chromatographed over silica gel column using hexane-ethyl acetate (95:5) as eluents to give the product (370 mg, 88%). The crude product was further recrystallized from chloroform-hexane to give the pure product as a pale pink color solid, mp 146-148° C. IR (neat) $v_{max}$ 3458, 2931, 1605, 1564, 1254, 1195, 1121, 1041, 965 cm$^{-1}$; $^1$H NMR (400 MHz, DMSO-d$_6$): δ 8.36 (1H, s), 8.20 (1H, s), 7.89 (1H, dd, J=6.8, 2.8 Hz), 7.58-7.62 (1H, m), 7.39 (1H, t, J=9.0 Hz), 3.10 (2H, br s), 2.91 (2H, br s), 1.84 (4H, br s); LC-MS (negative ion mode): m/z 380, 382 (M−H)$^−$.

Step d

HCl Salt

To a solution of step c compound (100 mg) in dioxane (5 mL) was added HCl in dioxane (0.1 mL) until the pH paper showed red color at rt. The solution was stirred for 15 min and the separated salt was filtered, washed with dioxane and dried to give the product as an off-white color solid (100 mg). LC-MS (negative ion mode): m/z 378, 380, 381 (M−HCl+H)$^−$.

Example 2

Synthesis of (5-bromo(3-pyridyl))-5,6,7,8-tetrahydrobenzo[1,2-b]pyrimidino[5,6-d]selenophen-4-ylamine (compd. No. 2)

Step a

(5-Bromo(3-pyridyl))-5,6,7,8-tetrahydrobenzo[1,2-b]pyrimidino[5,6-d]selenophen-4-ylamine To a solution of 4-chloro-5,6,7,8-tetrahydrobenzo[1,2-b]pyrimidino[5,4-d]selenophene (500 mg, 1.84 mmol, from step b of example 1) in DMF (10 mL) was added sequentially 3-amino-5-bromopyridine (380 mg, 2.19 mmol) and powdered NaOH (220 mg, 5.5 mmol) at rt and the mixture was stirred at rt for 36 h. The mixture was poured into ice cooled water and stirred for 10 min. The precipitated solid was filtered, washed with water and dried. The crude solid was chromatographed over silica gel column using hexane-EtOAc (70:30) as eluents to give the product as an off-white color solid (500 mg, 67%), which was recrystallized from acetonitrile, mp 170-172° C. $^1$H NMR (400 MHz, CDCl$_3$): δ 8.66 (1H, t, J=2.0 Hz), 8.56 (1H, d, J=2.4 Hz), 8.49 (1H, s), 8.39 (1H, d, J=1.6 Hz), 7.24 (1H, s, exchangeable with D$_2$O), 3.08 (2H, t, J=6.2 Hz), 2.96 (2H, t, J=6.0 Hz), 2.00-2.06 (2H, m), 1.92-1.98 (2H, m); $^{13}$C NMR (100 MHz, CDCl$_3$): δ 171.7, 154.7, 151.6, 145.3, 140.8, 140.0, 136.4, 130.3, 126.4, 120.5, 120.0, 28.4, 28.1, 22.7, 22.3; LC-MS (positive ion mode): m/z 407, 409, 411 (M+H)$^+$.

Step b

HCl Salt:

To a solution of step a compound (100 mg) in dioxane (10 mL) was added HCl in dioxane as described in example 1, gave the product as an off-white color solid, mp 254-256° C. LC-MS (negative ion mode): m/z 405, 407, 409 (M−HCl−H)$^−$.

Example 3

Synthesis of (2,6-dichloropyridin-4-yl)-5,6,7,8-tetrahydrobenzo[1,2-b]pyrimidino[5,6-d]selenophen-4-ylamine (compd. No. 3)

Step a

(2,6-Dichloropyridin-4-yl)-5,6,7,8-tetrahydrobenzo[1,2-b]pyrimidino[5,6-d]selenophen-4-ylamine To a solution of 4-chloro-5,6,7,8-tetrahydrobenzo[1,2-b]pyrimidino[5,4-d]selenophene (470 mg, 1.72 mmol, from step b of example 1) in DMF (10 mL) was added sequentially 4-amino-2,6-dichloropyridine (420 mg, 2.58 mmol) and powdered NaOH (210 mg, 5.16 mmol) at rt and the mixture was stirred at rt for 16 h. Work-up of the mixture as described in example 2, gave the product as a pale yellow color solid (500 mg, 73%), mp 238-242° C. $^1$H NMR (400 MHz, DMSO-d$_6$): δ 9.00 (1H, s, exchangeable with D$_2$O), 8.62 (1H, s), 7.76 (2H, s), 3.07 (2H, br s), 2.94 (2H, br s), 1.84 (4H, br s); $^{13}$C NMR (100 MHz, DMSO-d$_6$): δ 172.3, 153.1, 151.3, 151.0, 149.2, 140.5, 128.3, 122.3, 112.1, 27.7, 26.7, 22.6, 21.9; LC-MS (negative ion mode): m/z 395, 397, 399 (M−H)$^−$.

Step b

HCl Salt:

To a solution of step a compound (90 mg) in dioxane (10 mL) was added HCl in dioxane and work-up as described in example 1, gave the product as a pale yellow color solid, mp 286-290° C. LC-MS (negative ion mode): m/z 395, 397, 399, 401 (M−HCl−H)$^−$.

Example 4

Synthesis of (2,6-dichloropyrimidin-4-yl)-5,6,7,8-tetrahydrobenzo[1,2-b]pyrimidino[5,6-d]selenophen-4-ylamine (compd. No. 4)

Step a

(2,6-Dichloropyrimidin-4-yl)-5,6,7,8-tetrahydrobenzo[1,2-b]pyrimidino[5,6-d]selenophen-4-ylamine To a solution of 4-chloro-5,6,7,8-tetrahydrobenzo[1,2-b]pyrimidino[5,4-d]selenophene (500 mg, 1.83 mmol, from step b of example 1) in DMF (10 mL) was added sequentially 4-amino-2,6-dichloropyrimidine (450 mg, 2.75 mmol) and powdered NaOH (220 mg, 5.50 mmol) at rt. Work-up of the mixture as described in example 2, gave the product as an off-white color solid (500 mg, 68%), mp 268-270° C. $^1$H NMR (400 MHz, CDCl$_3$): δ 8.67 (1H, s), 8.64 (1H, s), 8.23 (1H, s, exchangeable with D$_2$O), 3.11 (2H, t, J=6.1 Hz), 2.97 (2H, t, J=6.1 Hz), 2.01-2.06 (2H, m), 1.92-1.98 (2H, m); $^{13}$C NMR (100 MHz, CDCl$_3$): δ 172.9, 162.7, 160.0, 159.2, 152.4, 151.0, 142.7, 126.3, 121.3, 107.8, 28.3, 28.2, 22.7, 22.4; LC-MS (negative ion mode): m/z 396, 398, 400, 402 (M−H)⁻.

Step b

HCl Salt:

To a solution of step a compound (90 mg) in dioxane (20 mL) was added HCl in dioxane and work-up as described in example 1, gave the product as a white color solid, mp 282-284° C. LC-MS (negative ion mode): m/z 396, 398, 400, 402 (M−HCl−H)⁻.

Example 5

Synthesis of pyrazin-2-yl-5,6,7,8-tetrahydrobenzo[1,2-b]pyrimidino[5,6-d]selenophen-4-ylamine (compd. No. 5)

Step a

Pyrazin-2-yl-5,6,7,8-tetrahydrobenzo[1,2-b]pyrimidino[5,6-d]selenophen-4-ylamine To a solution of 4-chloro-5,6,7,8-tetrahydrobenzo[1,2-b]pyrimidino[5,4-d]selenophene (600 mg, 2.20 mmol, from step b of example 1) in DMF (10 mL) was added sequentially 4-aminopyrazine (310 mg, 3.30 mmol) and powdered NaOH (260 mg, 6.60 mmol) at rt. Work-up as described in example 2, gave the product as a pale yellow color solid (470 mg, 65%), mp 192-194° C. $^1$H NMR (400 MHz, CDCl$_3$): δ 9.94 (1H, s), 8.56 (1H, s), 8.29 (1H, s), 8.23 (1H, s), 7.93 (1H, s, exchangeable with D$_2$O), 3.14 (2H, s), 2.96 (2H, s), 2.01 (2H, s), 1.95 (2H, s); $^{13}$C NMR (100 MHz, CDCl$_3$): δ 171.9, 153.4, 151.5, 149.1, 141.9, 138.8, 137.7, 126.7, 120.1, 28.2, 28.1, 22.7, 22.5; LC-MS (negative ion mode): m/z 328, 330 (M−H)⁻.

Step b

HCl Salt:

To a solution of step a compound (70 mg) in chloroform (5 mL) was added HCl in dioxane and work-up as described in example 1, gave the product as an off-white color solid (70 mg, 91%), mp 222-224° C. LC-MS (positive ion mode): m/z 330, 332 (M−HCl+H)⁺.

Example 6

Synthesis of (2,5-dibromo(3-thienyl)-5,6,7,8-tetrahydrobenzo[1,2-b]pyrimidino[5,6-d]selenophen-4-ylamine (compd. No. 6)

Step a

N-(2,5-Dibromothiophen-3-yl)acetamide

To an ice cold solution of 2,5-dibromo-3-nitrothiophene (5.0 g, 17.4 mmol, DellErba, C.; Spinelli, D. Tetrahedron, 1965, 21, 1061-1066) in acetic acid-acetic anhydride (1:1, 50 mL) was added iron powder (5.8 g, 104.5 mmol) slowly for 15 min. and stirred at rt for 4 h. After completion of the reaction, the reaction mixture was poured into ice cold water (500 mL) and stirred for 15 min. The precipitated solid was filtered, washed with water and dried. The crude product was chromatographed over silica gel column using hexane-EtOAc (95:5) as eluent to give the product as a white color solid (3.0 g, 58%), mp 114-116° C. $^1$H NMR (400 MHz, CDCl$_3$): δ 7.78 (1H, s), 7.21 (1H, s), 2.20 (3H, s).

Step b 2,5-Dibromothiophen-3-amine hydrochloride

A mixture of step a compound (3.0 g) and HCl in methanol (2N, 30 mL) was stirred at rt for 3 h. The separated solid was filtered, washed with methanol and dried to give the product as a white color solid (2.0 g, 67%), mp 150-160° C. $^1$H NMR (400 MHz, DMSO-d$_6$): δ 8.32 (1H, s), 6.76-7.17 (3H, m); LC-MS (positive ion mode): m/z 256, 258, 260 (M−HCl+H)⁺.

Step c (2,5-Dibromo(3-thienyl)-5,6,7,8-tetrahydrobenzo[1,2-b]pyrimidino[5,6-d]selenophen-4-ylamine To a solution of 4-chloro-5,6,7,8-tetrahydrobenzo[1,2-b]pyrimidino[5,4-d]selenophene (500 mg, 1.82 mmol, from step b of example 1) in DMF (10 mL) was added sequentially 2,5-dibromothiophen-3-amine (700 mg, 2.75 mmol, after basifying the above salt obtained from step b) and powdered NaOH (220 mg, 5.5 mmol) at rt. Work-up of the mixture as described in example 2, gave the product as a brown color solid, mp 184-186° C. $^1$H NMR (400 MHz, CDCl$_3$): δ 8.45 (1H, s), 8.09 (1H, s), 7.49 (1H, s, exchangeable with D$_2$O), 3.14 (2H, t, J=6.0 Hz), 2.94 (2H, t, J=6.0 Hz), 1.98-2.04 (2H, m), 1.90-1.96 (2H, m); $^{13}$C NMR (100 MHz, CDCl$_3$): δ 171.5, 154.0, 151.8, 140.0, 136.4, 126.8, 126.7, 119.6, 110.4, 94.8, 28.5, 28.1, 22.7, 22.7; LC-MS (positive ion mode): m/z 490, 492, 494, 496 (M+H)⁺.

Step d

HCl Salt:

To a solution of step c compound (80 mg) in dioxane (10 mL) was added HCl in dioxane and work-up as described in example 1, gave the product as a brown color solid (80 mg), mp 240° C. LC-MS (positive ion mode): m/z 490, 492, 494, 496 (M−HCl+H)⁺.

Example 7

Synthesis of (5-tert-butyl)-3-(5,6,7,8-tetrahydrobenzo[1,2-b]pyrimidino[5,6-d]selenophen-4-ylamino)thiophene-2-carboxamide (compd. No. 7)

Step a 5-tert-Butyl-3-aminothiophene-2-carbonitrile

To a suspension of sodium sulfide (3.26 g, 41.8 mmol) in DMF (42 mL) was added a solution of 3-chloro-4,4-dimethylpent-2-enenitrile (6.0 g, 41.8 mmol, Ohta, H.; Ishizaka, T.; Tatsuzuki, M.; Yoshinaga, M.; Iida, I.; Yamaguchi, T.; Tomishima, Y.; Futaki, N.; Toda, Y.; Saito, S. Bioorg. Med. Chem., 2008, 16, 1111-1124) in DMF (21 mL) at rt for 5 min and stirred the mixture at 70-80° C. for 2 h. Then chloroacetonitrile (5.3 mL, 83.6 mmol) was added dropwise to the reaction mixture and again stirred at 70-80° C. for 2 h. Then, a solution of sodium methoxide (2.26 g, 41.8 mmol) in dry methanol (42 mL) was added dropwise and stirring was continued for 2 h at the same temperature. The mixture was allowed to rt and poured into cold water and stirred for 30 min. The solution was extracted with chloroform (3×100 mL) and the combined chloroform layer was washed with water, brine and dried over sodium sulfate. The solution was filtered and evaporated the solvent. The residue was chromatographed over silica gel column using hexane-EtOAc (90:10) as eluent to give the product as a pale brown color solid (4.9 g, 65%), mp 118-122° C. $^1$H NMR (400 MHz, CDCl$_3$): δ 6.32 (1H, s), 4.37 (2H, br s), 1.33 (9H, s); LC-MS (negative ion mode): m/z 179 (M−H)$^−$.

Step b 5-tert-Butyl-3-aminothiophene-2-carboxamide

To a solution of step a compound (3.8 g) in ethanol (100 mL) was added aqueous sodium hydroxide solution (38 mL, 10%) and the mixture was refluxed for 1 h. Ethanol was distilled off under vacuum and the mixture was poured into ice cold water and stirred for 15 min. The separated crystals were filtered off, washed with cold water and dried to give the product as a pale yellow color solid (3.2 g, 77%), mp 152-156° C. $^1$H NMR (400 MHz, DMSO-d$_6$): δ 6.67 (2H, s), 6.38 (1H, s), 6.32 (2H, s), 1.28 (9H, s); LC-MS (positive ion mode): m/z 199 (M+H)$^+$.

Step c (5-tert-Butyl)-3-(5,6,7,8-tetrahydrobenzo[1,2-b]pyrimidino[5,6-d]selenophen-4-ylamino)thiophene-2-carboxamide To a solution of 4-chloro-5,6,7,8-tetrahydrobenzo[1,2-b]pyrimidino[5,4-d]selenophene (700 mg, 2.57 mmol, from step b of example 1) in DMF (10 mL) was added sequentially 5-tert-butyl-3-aminothiophene-2-carboxamide (700 mg, 3.6 mmol) and powdered NaOH (310 mg, 7.7 mmol) at rt. Work-up of the mixture as described in example 2, gave the product as a yellow color solid, mp 240-244° C. $^1$H NMR (400 MHz, DMSO-d$_6$): δ 11.38 (1H, s, exchangeable with D$_2$O), 8.45 (1H, s), 8.27 (1H, s), 7.53 (2H, s, exchangeable with D$_2$O), 3.15 (2H, br s), 2.90 (2H, br s), 1.84-1.85 (4H, m), 1.39 (9H, s); $^{13}$C NMR (100 MHz, DMSO-d$_6$): δ 170.9, 166.1, 158.0, 153.1, 151.4, 143.4, 138.2, 128.2, 119.5, 119.2, 109.2, 34.5, 31.7, 27.7, 27.4, 22.4, 22.1; LC-MS (positive ion mode): m/z 433, 435 (M+H)$^+$.

Example 8

Synthesis of 5-(tert-butyl)-2-(5,6,7,8-tetrahydrobenzo[1,2-b]pyrimidino[5,6-d]selenophen-4-ylamino)furan-3-carbonitrile (compd. No. 8)

To a solution of 4-chloro-5,6,7,8-tetrahydrobenzo[1,2-b]pyrimidino[5,4-d]selenophene (500 mg, 1.83 mmol, from step b of example 1) in DMF (15 mL) was added sequentially 2-amino-5-tert-butylfuran-3-carbonitrile (300 mg, 1.83 mmol) and powdered NaOH (210 mg, 5.49 mmol) at rt. Work-up as described in example 2, gave the product as a yellow color solid (400 mg, 55%), mp 230-232° C. $^1$H NMR (400 MHz, CDCl$_3$): δ 9.78 (1H, s, H-2), 6.94 (1H, br s, exchangeable with D$_2$O, —NH), 6.35 (1H, s, H-4'), 3.30-3.31 (2H, m, H-8), 2.95 (2H, br s, H-5), 1.90-1.92 (4H, m, H-6,7), 1.38 (9H, s, tert-butyl); $^{13}$C NMR (100 MHz, CDCl$_3$): δ 163.2, 161.7, 158.0, 154.0, 144.7, 142.9, 137.1, 133.8, 125.9, 101.4, 97.8, 33.0, 29.0, 28.8, 28.4, 23.1, 22.5; LC-MS (positive ion mode): m/z 399, 401 (M+H)$^+$.

Example 9

Synthesis of 5-phenyl-2-(5,6,7,8-tetrahydrobenzo[1,2-b]pyrimidino[5,6-d]selenophen-4-ylamino)furan-3-carbonitrile (compd. No. 9)

To a solution of 4-chloro-5,6,7,8-tetrahydrobenzo[1,2-b]pyrimidino[5,4-d]selenophene (250 mg, 0.917 mmol, from step b of example 1) in DMF (10 mL) was added sequentially 2-amino-5-phenylfuran-3-carbonitrile (160 mg, 0.917 mmol; Matsuda, T.; Yamagata, K.; Tomioka, Y.; Yamazaki, M. Chem. Pharm. Bull., 1985, 33, 937-943) and powdered NaOH (110 mg, 2.751 mmol) at rt. Work-up as described in example 2, gave the product as a yellow color solid (300 mg, 78%), mp 252-256° C. (decomp). $^1$H NMR (400 MHz, CDCl$_3$): δ 9.82 (1H, s, H-2), 7.78-7.81 (2H, m, Ph), 7.41-7.45 (2H, m, Ph), 7.31-7.35 (1H, m, Ph), 7.16 (1H, br s, exchangeable with D$_2$O, —NH), 7.01 (1H, s, H-4'), 3.35 (2H, br s, H-8), 2.98 (2H, br s, H-5), 1.93-1.95 (4H, m, H-6,7); $^{13}$C NMR (100 MHz, CDCl$_3$): δ 162.3, 158.6, 153.7, 151.9, 145.3, 143.3, 137.0, 133.9, 129.5, 128.9, 128.4, 126.1, 124.3, 102.7, 100.1, 29.1, 28.4, 23.1, 22.5; LC-MS (positive ion mode): m/z 419, 421 (M+H)$^+$.

Example 10

Synthesis of 2-methylthio-4-(5,6,7,8-tetrahydrobenzo[1,2-b]pyrimidino[5,6-d]selenophen-4-ylamino)-1,3-thiazole-5-carbonitrile (compd. No. 10)

Step a

2-Methylthio-4-(5,6,7,8-tetrahydrobenzo[1,2-b]pyrimidino[5,6-d]selenophen-4-ylamino)-1,3-thiazole-5-carbonitrile To a solution of 4-chloro-5,6,7,8-tetrahydrobenzo[1,2-b]pyrimidino[5,4-d]selenophene (250 mg, 0.917 mmol) in DMF (8 mL) was added sequentially 4-amino-2-methylthio-thiazole-5-carbonitrile (235 mg, 1.376 mmol; Thomae, D.; Perspicace, E.; Hesse, S.; Kirsch, G.; Seek, P. Tetrahedron, 2008, 64, 9309-9314) and powdered NaOH (110 mg, 2.751 mmol) at rt. Work-up as described in example 2, gave the product as a yellow color solid (300 mg, 81%), mp 264-266° C. (decomp). $^1$H NMR (400 MHz, CDCl$_3$): δ 9.72 (1H, s, H-2), 6.75 (1H, s, exchangeable with D$_2$O, —NH), 3.38 (2H, br s, H-8), 2.98 (2H, br s, H-5), 2.82 (3H, s, —SCH$_3$), 1.91 (4H, br s, H-6,7); LC-MS (positive ion mode): m/z 406, 408 (M+H)$^+$.

Step b

HCl Salt:
To a solution of step a compound (80 mg) in dioxane (20 mL) was added HCl in dioxane and work-up as described in example 1, gave the product as a pale yellow color solid (60 mg), mp>340° C. LC-MS (positive ion mode): m/z 406, 408 (M−HCl+H)$^+$.

Example 11

Synthesis of (2-methylthio-5-nitro(1,3-thiazol-4-yl))-5,6,7,8-tetrahydrobenzo[1,2-b]pyrimidino[5,6-d]selenophen-4-ylamine (compd. No. 11)

To a solution of 4-chloro-5,6,7,8-tetrahydrobenzo[1,2-b]pyrimidino[5,4-d]selenophene (420 mg, 1.57 mmol) in DMF (8 mL) was added sequentially 2-(methylthio)-5-nitrothiazol-4-amine (300 mg, 1.57 mmol) and powdered NaOH (180 mg, 4.71 mmol) at rt. Work-up as described in example 2, gave the product as a yellow color solid, mp 204-206° C. $^1$H NMR (400 MHz, CDCl$_3$): δ 10.52 (1H, s, exchangeable with D$_2$O, —NH), 8.73 (1H, s, H-2), 3.11 (2H, t, J=5.2 Hz, H-8), 2.98 (2H, t, J=5.0 Hz, H-5), 2.75 (3H, s, —SCH$_3$), 1.92-1.98 (4H, m, H-6,7); $^{13}$C NMR (100 MHz, CDCl$_3$): δ 176.9, 173.7, 152.2, 151.6, 151.1, 150.9, 142.7, 127.4, 124.1, 28.4, 28.0, 22.8, 22.5, 16.1; LC-MS (positive ion mode): m/z 426, 428 (M+H)$^+$.

Example 12

Synthesis of 4-(5,6,7,8-tetrahydrobenzo[1,2-b]pyrimidino[5,6-d]selenophen-4-ylamino)benzenesulfonamide (compd. No. 12)

To a solution of 2-amino-4,5,6,7-tetrahydrobenzo[b]selenophene-3-carbonitrile (1.5 g, 6.637 mmol, Abdel-Hafez, Sh. H. Russian J. Org. Chem., 2005, 41, 396-401) in toluene (20 mL) was added sequentially acetic acid (0.1 mL) and dimethylformamide-dimethylacetal (DMF-DMA) (1.65 g, 13.93 mmol). The reaction mixture was stirred at 105° C. for 3 h. While stirring, methanol was collected using the Dean-Stark apparatus. Toluene was evaporated under vacuum to give as a brown liquid. The residue was dissolved in acetic acid (15 mL) and sulfonamide (1.14 g, 6.637 mmol) was added. The reaction mixture was refluxed for 6 h. The reaction mixture was attained to rt. The separated solid was filtered, washed with water and dried to give the product as an off-white color solid (1.8 g, 66%), mp 298-302° C. $^1$H NMR (400 MHz, DMSO-d$_6$): δ 8.46 (1H, s, exchangeable with D$_2$O), 8.42 (1H, s), 7.78 (4H, s), 7.23 (2H, s, exchangeable with D$_2$O), 3.12 (2H, s), 2.92 (2H, s), 1.85 (4H, m); $^{13}$C NMR (100 MHz, CDCl$_3$): δ 171.2, 154.8, 151.3, 142.7, 138.7, 137.7, 128.6, 126.3, 120.8, 120.5, 27.8, 27.0, 22.6, 22.0; LC-MS (negative ion mode): m/z 405, 407 (M–H)$^-$.

Example 13

Synthesis of [5-(tert-butyl)selenopheno[3,2-e]pyrimidin-4-yl](3-chloro-4-fluorophenyl)amine (compd. No. 13)

Step a

2-Amino-4-(tert-butyl)selenophene-3-carbonitrile

To a solution of 2-cyano-3,4,4-trimethyl-2-pentenenitrile (2 g, 13.5 mmol; Prout, F. S. J. Org. Chem., 1953, 18, 928-933) in THF (20 mL) was added sequentially selenium powder (1.06 g, 13.5 mmol) and diethylamine (14 mL, 135 mmol) at rt. The reaction mixture was refluxed for 6 h and allowed to rt. The reaction mixture was poured into ice cold water and stirred for 15 min. The solution was extracted with chloroform (3×100 mL) and the combined organic layer was washed with water, brine and dried over sodium sulfate. The solution was filtered and evaporated the solvent. The residue was chromatographed over silica gel column using hexane:ethyl acetate (90:10) as eluents to give the product an off-white color solid (1.5 g, 50%), mp 90-94° C. $^1$H NMR (400 MHz, CDCl$_3$): δ 6.50 (1H, s), 5.11 (2H, br s), 1.35 (9H, s).

Step b

[5-(tert-Butyl)selenopheno[3,2-e]pyrimidin-4-yl](3-chloro-4-fluorophenyl)amine

To a solution of step a compound (1.0 g, 4.4 mmol) in toluene (20 mL) was added sequentially acetic acid (0.1 mL) and DMF-DMA (1.16 mL, 8.8 mol). The reaction mixture was stirred at 105° C. for 3 h and treated with 3-chloro-4-fluoroaniline. Work-up of the reaction mixture as described in example 12, gave the product as an off-white color solid, mp 170-172° C. IR (KBr) ν$_{max}$ 3477, 2965, 1558, 1490, 1250, 1189, 1128, 1041, 965, 888, 784 cm$^{-1}$; $^1$H NMR (400 MHz, CDCl$_3$): δ 8.51 (1H, s), 7.86 (1H, dd, J=6.6, 2.6 Hz), 7.75 (1H, s), 7.44-7.48 (2H, m), 7.16 (1H, t, J=8.8 Hz), 1.65 (9H, s); $^{13}$C NMR (100 MHz, CDCl$_3$): δ 175.4, 155.0, 154.8 (d, J=245 Hz), 151.8, 145.1, 135.1 (d, J=3.0 Hz), 123.8, 118.5, 116.7 (d, J=22 Hz), 121.2 (d, J=18 Hz), 121.2 (d, J=7 Hz), 121.2, 35.2, 32.1; LC-MS (positive ion mode): m/z 382, 384, 386 (M+H)$^+$.

Step c

HCl Salt:
To a solution of step b compound (100 mg) in dioxane (5 mL) was added HCl in dioxane and work-up as described in example 1, gave the product as an off-white color solid (80 mg), mp 256-260° C.; LC-MS (negative ion mode): m/z 380, 382, 383 (M–H–HCl)$^-$.

Example 14

Synthesis of (3-chloro-4-fluorophenyl)(5-phenylselenopheno[3,2-e]pyrimidin-4-yl]amine (compd. No. 14)

Step a

2-Amino-4-phenylselenophene-3-carbonitrile

To a solution of 2-[1-(phenyl)ethylidene]-malononirile (1 g, 5.95 mmol; Barnes, D. M.; Haight, A. R.; Hameury, T.; McLaughlin, M. A.; Mei, J.; Tedrow, J. S.; Toma, J. D. R. Tetrahedron, 2006, 62, 11311-11319) in THF (20 mL) was added sequentially selenium powder (0.47 g, 5.95 mmol) and diethylamine (6.2 mL, 59.5 mmol) at rt. The reaction mixture was refluxed for 3 h and allowed to rt. Work-up of the reaction mixture as described in example 13, gave the product as a red color solid (700 mg, 47%). $^1$H NMR (400 MHz, CDCl$_3$): δ 7.53-7.55 (2H, m), 7.33-7.42 (3H, m), 6.86 (1H, s), 5.26 (2H, br s); $^{13}$C NMR (100 MHz, CDCl$_3$): δ 168.0, 141.7, 135.8, 128.6, 128.1, 127.5, 116.6, 109.6.

Step b (3-Chloro-4-fluorophenyl)(5-phenylselenopheno[3,2-e]pyrimidin-4-yl]amine

To a solution of step a compound (0.5 g, 2.02 mmol) in toluene (20 mL) was added sequentially acetic acid (0.1 mL) and DMF-DMA (0.6 mL, 4.23 mol). The reaction mixture was stirred at 105° C. for 2 h and treated with 3-chloro-4-fluoroaniline (351 mg, 2.45 mmol) as described in example 12, gave the product as an off-white color solid, mp 198-200° C. IR (KBr) ν$_{max}$ 3480, 3381, 3058, 1609, 1495, 1427, 1254, 1193, 1129, 966 cm$^{-1}$; $^1$H NMR (400 MHz, CDCl$_3$): δ 8.57 (1H, s), 7.76 (1H, s), 7.64 (1H, dd, J=6.6, 2.6 Hz), 7.57-7.60

(3H, m), 7.51-7.53 (2H, m), 6.98 (1H, t, J=8.8 Hz), 6.87-6.91 (1H, m), 6.71 (1H, br s); $^{13}$C NMR (100 MHz, CDCl$_3$): δ 172.6, 155.5, 154.2 (d, J=244 Hz), 152.8, 137.5, 136.5, 135.1 (d, J=3.0 Hz), 129.5, 129.3, 129.2, 125.6, 122.2, 120.9 (d, J=18 Hz), 119.6 (d, J=7 Hz), 117.2, 116.4 (d, J=22 Hz); LC-MS (positive ion mode): m/z 402, 404, 406 (M+H)$^+$.

Example 15

Synthesis of 4-[(3-chloro-4-fluorophenyl)amino]-5-methylselenopheno[2,3-d]pyrimidine-6-carboxylic acid (compd. No. 15)

Step a

Ethyl 5-amino-4-cyano-3-methylselenophene-2-carboxylate

To a solution of ethyl acetoacetate (5 g, 38.46 mmol) in ethanol (100 mL) was added sequentially malononitrile (2.53 g, 38.46 mmol), selenium powder (3.07 g, 38.46 mmol) and diethylamine (28 mL, 384 mmol) at rt. The reaction mixture was refluxed for 4 h and work-up as described in example 1, gave the product as a pale yellow color solid, mp 208-210° C. IR (KBr) ν$_{max}$ 3381, 3203, 2203, 1666, 1643, 1489, 1382, 1263, 1182, 1100 cm$^{-1}$; $^1$H NMR (400 MHz, CDCl$_3$): δ 5.47 (2H, br s), 4.26 (2H, q, J=7.1 Hz), 2.49 (3H, s), 1.33 (3H, t, J=7.1 Hz); LC-MS (negative ion mode): m/z 255, 257 (M−H)$^-$.

Step b

Ethyl 4-[3-chloro-4-fluorophenyl)amino]-5-methylselenopheno[2,3-d]pyrimidine-6-carboxylate To a solution of step a compound (2.0 g, 7.75 mmol) in toluene (200 mL) was added sequentially acetic acid (0.3 mL) and DMF-DMA (1.93 g, 16.27 mmol). The reaction mixture was stirred at 105° C. for 2 h and treated with 3-chloro-4-fluoroaniline (2.3 g, 15.5 mmol) as described in example 12, gave the product as an off-white color solid (2.1 g, 65%), mp 152-154° C. $^1$H NMR (400 MHz, CDCl$_3$): δ 8.53 (1H, s), 7.82 (1H, dd, J=6.4, 2.8 Hz), 7.41-7.45 (2H, m), 7.17 (1H, t, J=8.6 Hz), 4.37 (2H, q, J=7.2 Hz), 3.09 (3H, s), 1.41 (3H, t, J=7.2 Hz); LC-MS (negative ion mode): m/z 410, 412, 414 (M−H)$^-$.

Step c

4-[(3-Chloro-4-fluorophenyl)amino]-5-methylselenopheno[2,3-d]pyrimidine-6-carboxylic acid To a solution of step b compound (1.0 g, 2.42 mmol) in methanol (100 mL) was added a solution of sodium hydroxide (200 mg, 4.84 mmol) in water (10 mL) and stirred at rt for 16 h. The mixture was poured into ice cold water and extracted with chloroform (3×50 mL) to remove impurities. The aqueous solution was acidified with dil. HCl and stirred for 15 min. The precipitated solid was filtered, washed with water and dried to give the product as an off-white color solid (670 mg, 73%), mp 300-302° C. IR (KBr) ν$_{max}$ 3433, 2360, 1680, 1603, 1555, 1494, 1446, 1260, 1173, 1056, 996, 818, 745 cm$^{-1}$; $^1$H NMR (400 MHz, DMSO-d$_6$): δ 13.55 (1H, br s), 8.67 (1H, s), 8.49 (1H, s), 7.90-7.92 (1H, m), 7.62-7.64 (1H, m), 7.45 (1H, t, J=9.0 Hz), 3.02 (3H, s); $^{13}$C NMR (100 MHz, DMSO-d$_6$): δ 171.9, 164.9, 157.5, 153.9, 153.8 (d, J=242.0 Hz), 140.9, 135.9 (d, J=3.0 Hz), 127.6, 124.7, 123.6 (d, J=7.0 Hz), 121.0, 118.9 (d, J=18.0 Hz), 116.5 (d, J=22.0 Hz), 16.8; LC-MS (negative ion mode): m/z 382, 384, 386 (M−H)$^-$.

Step d

Sodium Salt:

To a solution of step c compound (50 mg, 0.125 mmol) in THF-methanol (4 mL, 1:1) was added a methanolic solution of sodium hydroxide (6 mg, 0.155 mmol in methanol, 0.6 mL) at rt and stirred for 30 min. The solution was evaporated under reduced pressure and dried in high vacuum to give the product as a pale yellow color solid (46 mg), mp 350-352° C. LC-MS (negative ion mode): m/z 382, 384, 386 (M−Na)$^-$.

Example 16

Synthesis of [(3-chloro-4-fluorophenyl)(6-methyl-5-phenylselenopheno[3,2-e]pyrimidin-4-yl]amine (compd. No. 16)

Step a

2-Amino-5-methyl-4-phenylselenophene-3-carbonitrile

To a solution of 2-(1-phenylpropylidene)malononitrile (5.0 g, 27.47 mmol; Karlsen, H.; Songe, P. H.; Sunsby, L. K.; Hagen, L. C.; Kolsaker, P.; Romming, C. J. Chem. Soc., Perkin Trans. 1, 2001, 497-507) in THF (160 mL) was added sequentially selenium powder (2.19 g, 27.47 mmol) and diethylamine (28.64 mL, 274.72 mmol) at rt. The reaction mixture was refluxed for 8 h and allowed to rt. Work-up of the reaction mixture as described in example 13, gave the product (3.0 g, 41%). IR (KBr) ν$_{max}$ 3403, 3323, 2972, 2194, 1611, 1511, 1439, 1365, 1302, 1122, 906, 770 cm$^{-1}$; $^1$H NMR (400 MHz, CDCl$_3$): δ 7.40-7.44 (2H, m), 7.31-7.37 (3H, m), 4.99 (2H, br s), 2.30 (3H, s); LC-MS (negative ion mode): m/z 261 (M−H)$^-$.

Step b (3-Chloro-4-fluorophenyl)(6-methyl-5-phenylselenopheno[3,2-e]pyrimidin-4-yl]amine To a solution of 2-amino-5-methyl-4-phenylselenophene-3-carbonitrile (1.0 g, 3.81 mmol) in toluene (30 mL) was added sequentially acetic acid (0.2 mL) and DMF-DMA (1.14 mL, 8.01 mol). The reaction mixture was stirred at 105° C. for 2 h and treated with 3-chloro-4-fluoroaniline (670 mg, 4.57 mmol) as described in example 12, gave the product as an off-white color solid, mp 166-168° C. IR (KBr) ν$_{max}$ 3397, 3020, 1614, 1563, 1498, 1433, 1263, 1196, 1145, 967, 904, 868, 774 cm$^{-1}$; $^1$H NMR (400 MHz, CDCl$_3$): δ 8.51 (1H, s), 7.59-7.62 (3H, m), 7.55 (1H, dd, J=6.4, 2.8 Hz), 7.42-7.45 (2H, m), 6.94 (1H, t, J=8.8 Hz), 6.76-6.96 (1H, m), 6.45 (1H, br s), 2.40 (3H, s); $^{13}$C NMR (100 MHz, CDCl$_3$): δ 170.2, 154.4, 154.0 (d, J=244.0 Hz), 152.0, 139.4, 136.4 (d, J=3.0 Hz), 131.9, 130.0, 130.0, 129.6, 129.2, 121.8, 120.8 (d, J=18.0 Hz), 119.3 (d, J=7.0 Hz), 118.9, 116.3 (d, J=22.0 Hz), 16.3; LC-MS (positive ion mode): m/z 416, 418, 420 (M+H)$^+$.

Step c

HCl Salt:

To a solution of step b compound (100 mg) in dioxane (10 mL) was added HCl in dioxane and work-up as described in example 1, gave the product as an off-white color solid (80 mg), mp 248-250° C. LC-MS (positive ion mode): m/z 416, 418, 420 (M–HCl+H)+.

Example 17

Synthesis of 4-[(3-chloro-4-fluorophenyl)amino]-5-methylselenopheno[2,3-d]pyrimidine-6-carboxamide (compd. No. 17)

To an ice cold (0-5° C.) solution of ammonium hydroxide (20 mL) was added a solution of ethyl 4-[3-chloro-4-fluorophenyl)amino]-5-methylselenopheno[2,3-d]pyrimidine-6-carboxylate (1.0 g, from step b of example 15) in THF (10 mL) for 5 min and catalytic amount of PEG-400 was added at rt, stirred for 48 h. The solution was poured into ice cooled water and extracted with ethyl acetate (3×100 mL). The combined organic layer was washed with water, brine and dried over sodium sulfate. The solution was filtered and evaporated the solvent. The residue was chromatographed over silica gel column using chloroform-methanol (95:5) as eluents to give the unreacted starting material (600 mg). Further elution of the column with the same solvent system gave the product as an off-white color solid (600 mg, 65%), mp 276-278° C. IR (KBr) $v_{max}$ 3440, 3378, 3161, 1655, 1556, 1499, 1384, 1339, 1260, 1214 cm$^{-1}$; $^1$H NMR (400 MHz, DMSO-d$_6$): δ 8.57 (1H, s, exchangeable with D$_2$O), 8.45 (1H, s), 7.89 (1H, dd, J=6.4, 2.0 Hz), 7.71 (2H, br s, exchangeable with D$_2$O), 7.59-7.62 (1H, m), 7.42 (1H, t, J=9.2 Hz), 2.84 (3H, s); $^{13}$C NMR (100 MHz, DMSO-d$_6$): δ 171.2, 165.4, 157.1, 153.7 (d, J=241.0 Hz), 153.1, 136.1 (d, J=3.0 Hz), 133.4, 133.3, 124.7, 123.6 (d, J=7.0 Hz), 120.5, 118.8 (d, J=18.0 Hz), 116.4 (d, J=22.0 Hz), 17.3; LC-MS (negative ion mode): m/z 381, 383, 385 (M–H)$^-$.

Example 18

Synthesis of (3-chloro-4-fluorophenyl)-5,6,7,8-tetrahydropyrimidino[5',6'-5,4]selenopheno[2,3-c]pyridine-4-ylamine (compd. No. 18)

Step a tert-Butyl 2-amino-3-cyano-4,5,6,7-tetrahydroselenopheno[2,3-c]pyridine-6-carboxylate To a solution of tert-butyl 4-(dicyanomethylene)piperidinecarboxylate (10 g, 40.48 mmol; Wang, X.-S.; Wu, J.-R.; Zhou, J.; Tu, S.-J. J. Comb. Chem., 2009, 11, 1011-1022) in THF (500 mL) was added sequentially selenium powder (3.23 g, 40.48 mmol) and diethylamine (42.2 mL, 404.8 mmol) at rt. The reaction mixture was refluxed for 7 h and allowed to rt. Work-up of the reaction mixture as described in example 13, gave the product as a yellow color solid (5.93 g, 45%), mp 190-192° C. $^1$H NMR (400 MHz, CDCl$_3$): δ 5.05 (2H, s), 4.41 (2H, br s), 3.66 (2H, t, J=5.6 Hz), 2.58 (2H, br s), 1.48 (9H, s); LC-MS (negative ion mode): m/z 326 (M–H)$^-$.

Step b tert-Butyl 4-[(3-chloro-4-fluorophenyl)amino]-5,6,7,8-tetrahydropyrimidino[5',4'-5,4]selenopheno[2,3-c]pyridine-7-carboxylate To a solution of step a compound (1.0 g, 3.05 mmol) in toluene (30 mL) was added sequentially acetic acid (0.3 mL) and DMF-DMA (0.92 mL, 6.422 mmol) at rt. The reaction mixture was stirred at 100° C. for 2 h and treated with 3-chloro-4-fluoroaniline (0.98 g, 6.116 mmol) as described in example 12, gave the product as a white color solid, mp 202-204° C. $^1$H NMR (400 MHz, CDCl$_3$): δ 8.46 (1H, s), 7.80 (1H, br s), 7.41 (1H, br s), 7.15 (1H, t, J=8.6 Hz), 6.94 (1H, br s, exchangeable with D$_2$O), 4.75 (2H, br s), 3.84 (2H, t, J=5.6 Hz), 3.13 (2H, m), 1.51 (9H, s); LC-MS (negative ion mode): m/z 479, 481, 483 (M–H)$^-$.

Step c (3-Chloro-4-fluorophenyl)-5,6,7,8-tetrahydropyrimidino[5',6'-5,4]selenopheno[2,3-c]pyridine-4-ylamine To a solution of step b compound (500 mg) in methanol (10 mL) was added conc. HCl (8 mL) at rt and the mixture was stirred for 30 min. The mixture was poured into ice cold water and basified with ammonium hydroxide solution. The precipitated solid was filtered, washed with ice cold water and dried to give the crude product (250 mg, 65%). The crude product was recrystallized from hexane-chloroform to give the product as a white color solid, mp 188-190° C. IR (KBr) $v_{max}$ 3449, 1605, 1562, 1494, 1425, 1264, 1206, 1106, 988, 961, 796 cm$^{-1}$; $^1$H NMR (400 MHz, CDCl$_3$): δ 8.45 (1H, s), 7.80 (1H, dd, J=6.6, 2.6 Hz), 7.40-7.44 (1H, m), 7.14 (1H, t, J=8.8 Hz), 7.02 (1H, br s), 4.17-4.18 (2H, m), 3.31 (2H, t, J=5.6 Hz), 3.06-3.09 (2H, m); $^{13}$C NMR (100 MHz, CDCl$_3$): δ 171.5, 155.5, 154.5 (d, J=188 Hz), 152.0, 139.1, 135.1, 125.5, 123.8, 121.3 (d, J=6.0 Hz), 121.2 (d, J=19.0 Hz), 119.4, 116.6 (d, J=22.0 Hz), 47.3, 43.0, 29.5;

LC-MS (negative ion mode): m/z 379, 381, 383 (M–H)$^-$.

Step d

HCl Salt:

To a solution of step c compound (100 mg) in dioxane was added HCl in dioxane and work-up as described in example 1, gave the product as an off-white color solid, mp 340° C. LC-MS (negative ion mode): m/z 379, 381, 383 (M–H—HCl)$^-$.

Example 19

Synthesis of 4[(3-chloro-4-fluorophenyl)amino]-7-(methylsulfonyl)-5,6,7,8-tetrahydro-pyrimidino[5',4'-5,4]selenopheno[2,3-c]pyridine (compd. No. 19)

Step a

4[(3-Chloro-4-fluorophenyl)amino]-7-(methylsulfonyl)-5,6,7,8-tetrahydro-pyrimidino[5',4'-5,4]selenopheno[2,3-c]pyridine To an ice cold suspension of (3-chloro-4-fluorophenyl)-5,6,7,8-tetrahydropyrimidino[5',6'-5,4]selenopheno[2,3-c]pyridine-4-ylamine (100 mg, 0.26 mmol, from example 18) in dichloroethane (10 mL) was added potassium carbonate (70 mg, 0.52 mmol) followed by methane sulfonyl chloride (0.04 g, 0.314 mmol) for 10 min and stirred at rt for 4 h. The reaction mixture was poured into ice cooled water and stirred for 15 min. EDC layer was separated and the aqueous layer was extracted with chloroform (2×100 mL) and the combined organic layer was washed with water, brine and dried over sodium sulfate. The solution was filtered and evaporated the solvent. The residue was recrystallized from methanol-chloroform-hexane to give the product as an off-white color solid (50 mg, 41%), mp 220-222° C. IR (KBr) $v_{max}$ 3435, 1607, 1563, 1494, 1429, 1331, 1260, 1156, 964, 928, 778 cm$^{-1}$; $^1$H NMR (400 MHz, DMSO-d$_6$): δ 8.42 (1H, s), 8.28 (1H, br s, exchangeable with D$_2$O), 7.89 (1H, dd, J=6.6, 2.6 Hz), 7.61-7.64 (1H, m), 7.41 (1H, t, J=9.0 Hz), 4.61 (3H, s), 3.55-3.57 (2H, m), 3.35 (2H, br s), 3.02 (2H, br s); $^{13}$C NMR (100 MHz, CDCl$_3$): δ 171.5, 155.4, 153.3 (d, J=241 Hz), 151.9, 136.5 (d, J=3.0 Hz), 132.6, 127.2, 123.6, 122.5 (d, J=7.0 Hz), 119.2, 118.7 (d, J=18.0 Hz), 116.4 (d, J=21.0 Hz), 46.7, 42.4, 36.0, 27.2; LC-MS (negative ion mode): m/z 457, 459, 461 (M−H)$^-$.

Step b

HCl Salt:

To a solution of step a compound (50 mg) in dioxane (3 mL) was added HCl in dioxane and work-up as described in example 1, gave the product as an off-white color solid (40 mg), mp 260-262° C. LC-MS (negative ion mode): m/z 457, 459, 461 (M−HCl−H)$^-$.

Example 20

Synthesis of (3-bromophenyl)-5,6,7,8-tetrahydropyrimidino[5',6'-5,4]selenopheno[2,3-c]pyridin-4-ylamine (compd. No. 20)

Step a (3-Bromophenyl)-5,6,7,8-tetrahydropyrimidino[5',6'-5,4]selenopheno[2,3-c]pyridin-4-ylamine To a solution of N-Boc-2-amino-4,5,6,7-tetrahydroselenopheno[2,3-c]pyridine-3-carbonitrile (1.5 g, 4.587 mmol, step a of example 18) in toluene (30 mL) was added sequentially acetic acid (0.1 mL) and DMF-DMA (1.3 mL, 9.63 mmol). The reaction mixture was stirred at 105° C. for 3 h and treated with 3-bromoaniline (780 mg, 4.587 mmol) as described in example 12, gave the product as a brown color solid, mp 148-150° C. $^1$H NMR (400 MHz, CDCl$_3$): δ 8.47 (1H, s), 7.91 (1H, s), 7.54 (1H, d, J=6.8 Hz), 7.20-7.26 (2H, m), 7.09 (1H, s, exchangeable with D$_2$O), 4.16 (2H, s), 3.31 (2H, t, J=5.7 Hz), 3.07 (2H, t, J=5.7 Hz); $^{13}$C NMR (100 MHz, CDCl$_3$): δ 171.4, 155.3, 152.0, 139.9, 139.0, 130.3, 126.8, 125.5, 123.9, 122.7, 119.6, 119.5, 47.3, 42.9, 29.4; LC-MS (positive ion mode): m/z 407, 409, 411 (M+H)$^+$.

Step b

HCl Salt:

To a solution of step a compound (150 mg) in dioxane (10 mL) was added HCl in dioxane and work-up as described in example 1, gave the product as an off-white color solid (140 mg, 86%), mp 308-310° C. LC-MS (negative ion mode): m/z 405, 407, 409 (M−H)$^-$.

Example 21

Synthesis of (3-ethynylphenyl)-5,6,7,8-tetrahydropyrimidino[5',6'-5,4]selenopheno[2,3-c]pyridine-4-ylamine (compd. No. 21)

Step a (3-Ethynylphenyl)-5,6,7,8-tetrahydropyrimidino[5',6'-5,4]selenopheno[2,3-c]pyridine-4-ylamine To a solution of N-Boc-2-amino-4,5,6,7-tetrahydroselenopheno[2,3-c]pyridine-3-carbonitrile (2.0 g, 6.13 mmol, step a of example 18) in toluene (40 mL) was added sequentially acetic acid (0.2 mL) and DMF-DMA (1.0 mL, 7.35 mmol). The reaction mixture was stirred at 105° C. for 3 h and treated with 3-ethynylaniline (0.8 mL, 7.3 mmol) as described in example 12, gave the product as a brown color solid, mp 164-166° C. $^1$H NMR (400 MHz, CDCl$_3$): δ 8.46 (1H, s), 7.74 (1H, s), 7.68 (1H, dd, J=8.0, 1.2 Hz), 7.32 (1H, t, J=7.8 Hz), 7.24 (1H, br s), 7.09 (1H, s, exchangeable with D$_2$O), 4.16 (2H, s), 3.30 (2H, t, J=5.7 Hz), 3.10 (1H, s), 3.06 (2H, t, J=5.7 Hz); $^{13}$C NMR (100 MHz, CDCl$_3$): δ 170.9, 155.2, 151.4, 139.6, 138.2, 128.9, 127.6, 126.3, 124.6, 122.5, 121.8, 120.0, 83.4, 80.4, 46.8, 42.4, 28.4; LC-MS (positive ion mode): m/z 353, 355 (M+H)$^+$.

Step b

HCl Salt:

To a solution of step a compound (50 mg) in dioxane (5 mL) was added HCl in dioxane and work-up as described in example 1, gave the product as a pale brown color solid (50 mg), mp 306-310° C. LC-MS (positive ion mode): m/z 353, 355 (M−HCl+H)$^+$.

Example 22

Synthesis of (3,4-dichlorophenyl)-5,6,7,8-tetrahydropyrimidino[5',6'-5,4]selenopheno[2,3-c]pyridin-4-ylamine (compd. No. 22)

Step a (3,4-Dichlorophenyl)-5,6,7,8-tetrahydropyrimidino[5',6'-5,4]selenopheno[2,3-c]pyridin-4-ylamine To a solution of N-Boc-2-amino-4,5,6,7-tetrahydroselenopheno[2,3-c]pyridine-3-carbonitrile (1.5 g, 4.60 mmol, step a of example 18) in toluene (40 mL) was added sequentially acetic acid (0.2 mL) and DMF-DMA (1.43 mL, 9.66 mmol). The reaction mixture was stirred at 105° C. for 3 h and treated with 3,4-dichloroaniline (0.89 mL, 5.52 mmol) as described in example 12, gave the product as a yellow color solid, mp 192-194° C. $^1$H NMR (400 MHz, CDCl$_3$): δ 8.47 (1H, s), 7.91 (1H, s), 7.39-7.46 (2H, m), 7.08 (1H, s), 4.17 (2H, s), 3.31 (2H, s), 3.06 (2H, s); $^{13}$C NMR (100 MHz, CDCl$_3$): δ 171.6, 155.1, 151.9, 139.3, 138.1, 132.8, 130.5, 127.1, 125.4, 122.7, 120.4, 119.6, 47.3, 42.9, 29.4; LC-MS (negative ion mode): m/z 395, 397, 399, 401 (M−H)$^-$.

Step b

HCl Salt:

To a solution of step a compound (100 mg) in chloroform (10 mL) was added HCl in dioxane and work-up as described in example 1, gave the product as an off-white color solid (100 mg, 92%), mp 308-310° C. LC-MS (negative ion mode): m/z 395, 397, 399, 401 (M−HCl−H)⁻.

Example 23

Synthesis of methyl 5-methyl-4-(5,6,7,8-tetrahydro-pyrimidino[5',6'-5,4]selenopheno[2,3-c]pyridin-4-ylamino)thiophene-2-carboxylate (compd. No. 23)

Step a

Methyl 5-methyl-4-(5,6,7,8-tetrahydropyrimidino[5', 6'-5,4]selenopheno[2,3-c]pyridin-4-ylamino) thiophene-2-carboxylate To a solution of N-Boc-2-amino-4,5,6,7-tetrahydroseleno-pheno[2,3-c]pyridine-3-carbonitrile (2.0 g, 6.13 mmol, step a of example 18) in toluene (30 mL) was added sequentially acetic acid (0.1 mL) and DMF-DMA (1.7 mL, 12.84 mmol). The reaction mixture was stirred at 105° C. for 3 h and treated with methyl 4-amino-5-methylthiophene-2-carboxylate (1.04 g, 6.116 mmol; Tsubou, S.; Mimura, S.; Ono, S.-I.; Watanabe, K.; Takeda, A. Bull. Chem. Soc. Jpn., 1987, 60, 1807-1812) as described in example 12, gave the product as a yellow color solid, mp 224-226° C. $^1$H NMR (400 MHz, CDCl$_3$): δ 8.41 (1H, s), 8.08 (1H, s), 6.73 (1H, s, exchangeable with D$_2$O), 4.17 (2H, s), 3.88 (3H, s), 3.31 (2H, t, J=5.6 Hz), 3.08 (2H, t, J=5.4 Hz), 2.40 (3H, s); $^{13}$C NMR (100 MHz, CDCl$_3$): δ 171.2, 162.4, 155.8, 152.5, 138.5, 135.1, 133.0, 131.5, 128.1, 125.6, 119.0, 52.1, 47.3, 43.0, 29.4, 13.0; LC-MS (negative ion mode): m/z 405, 407 (M−H)⁻.

Step b

HCl Salt:

To a solution of step a compound (70 mg) in dioxane (5 mL) was added HCl in dioxane and work-up as described in example 1, gave the product as an yellow color solid (65 mg, 85%), mp 262-264° C. LC-MS (negative ion mode): m/z 405, 407 (M−HCl−H)⁻.

Example 24

Synthesis of {4-[3-chloro-4-fluorophenyl)amino]-5-methylselenopheno[2,3-d]pyrimidin-6-yl}-N-(2-hydroxyethyl)carboxamide (compd. No. 24)

To a solution of ethyl 4-[3-chloro-4-fluorophenyl)amino]-5-methylselenopheno[2,3-d]pyrimidine-6-carboxylate (2.0 g, from step b of example 15) in ethanol (50 mL) was added ethanol amine (20 mL) for 5 min and stirred at rt for 16 h. Ethanol was evaporated under reduced pressure and the residue was diluted with ice cooled water. The solution was extracted with ethyl acetate (3×100 mL). The combined organic layer was washed with water, brine and dried over sodium sulfate. The solution was filtered and evaporated the solvent. The residue was chromatographed over silica gel column using chloroform-methanol (90:10) as eluents to give the product as an off-white color solid (1.2 g, 60%), mp 198-200° C. $^1$H NMR (400 MHz, DMSO-d$_6$): δ 8.55 (1H, br s), 8.45 (1H, s), 8.32 (1H, br s), 7.88-7.90 (1H, m), 7.60-7.63 (1H, m), 7.44 (1H, t, J=9.0 Hz), 4.77 (1H, m), 3.52-3.55 (2H, m), 3.34-3.36 (2H, m), 2.81 (3H, s); LC-MS (negative ion mode): m/z 425, 427, 429 (M−H)⁻.

Example 25

Synthesis of N-(2-chloroethyl){4-[3-chloro-4-fluorophenyl)amino]-5-methylselenopheno[2,3-d]pyrimidin-6-yl}carboxamide (compd. No. 25)

Step a

N-(2-Chloroethyl) {4-[3-chloro-4-fluorophenyl)amino]-5-methylselenopheno[2,3-d]pyrimidin-6-yl}carboxamide A mixture of {4-[3-chloro-4-fluorophenyl)amino]-5-methylselenopheno[2,3-d]pyrimidin-6-yl}-N-(2-hydroxyethyl)carboxamide (1.0 g, from example 24) and thionyl chloride (30 mL) was refluxed for 2 h. The reaction mixture was cooled to rt and poured into ice cooled water and stirred for 10 min. The precipitated solid was filtered, washed with water and dried. The crude solid was chromatographed over silica gel column using chloroform-methanol (90:10) as eluents to give the product as a yellow color solid (600 mg, 57%), mp 178-180° C. IR (KBr) ν$_{max}$ 3456, 3239, 2919, 1540, 1612, 1548, 1492, 1458, 1426, 1386, 1266, 1188, 1124, 1052, 976, 879, 807 cm⁻¹; $^1$H NMR (400 MHz, DMSO-d$_6$): δ 8.59-8.62 (1H, m, exchangeable with D$_2$O), 8.57 (1H, s, exchangeable with D$_2$O), 8.45 (1H, s), 7.90 (1H, dd, J=6.8, 2.4 Hz), 7.59-7.64 (1H, m), 7.42 (1H, t, J=9.2 Hz), 3.78 (2H, t, J=6.0 Hz), 3.60 (2H, q, J=5.9 Hz), 2.83 (3H, s); $^{13}$C NMR (100 MHz, DMSO-d$_6$): δ 171.1, 163.9, 157.1, 153.7 (d, J=242.0 Hz), 153.1, 136.1 (d, J=3.0 Hz), 133.4, 132.4, 124.8, 123.7 (d, J=7.0 Hz), 120.7, 118.8 (d, J=19.0 Hz), 116.4 (d, J=22.0 Hz), 43.0, 41.6, 17.4; LC-MS (negative ion mode): m/z 443, 445, 447 (M−H)⁻.

Step b

HCl Salt:

To a solution of step a compound (70 mg) in acetonitrile (5 mL) was added HCl in dioxane and work-up as described in example 1, gave the product as a pale yellow color solid (60 mg), mp 226-228° C. LC-MS (negative ion mode): m/z 443, 445, 447 (M−HCl−H)⁻.

Example 26

Synthesis of 4-[(3-chloro-4-fluorophenyl)amino]-5, 6,8-trihydrobenzo[2,1-b]pyrimidino[5,4-d]sele-nophen-7-one (compd. No. 26)

Step a

7-Aminospiro[1,3-dioxolane-2,6'-4,5,6,7-tetrahy-drobenzo[2,1-b]selenophene]-8-carbonitrile To a solution of 1,4-cyclohexanedione monoethylene acetal (3 g, 19.23 mmol; Sigma-Aldrich) in ethanol (30 mL) was added sequentially malononitrile (1.2 mL, 19.23 mmol), selenium powder (1.5 g, 19.23 mmol) and diethylamine (10 mL, 96.15 mmol) at rt. The reaction mixture was refluxed for 5 h and work-up as described in example 1, gave the product as an off-white color solid, mp 192-194° C. $^1$H NMR (400 MHz, CDCl$_3$): δ 4.98 (2H, br s), 4.02 (4H, s), 2.82 (2H, s), 2.66-2.70 (2H, m), 1.92 (2H, t, J=6.6 Hz); LC-MS (positive ion mode): m/z 283, 285 (M+H)$^+$.

Step b (3-Chloro-4-fluorophenyl)spiro[1,3-dioxolane-2,7'-5,6,7,8-tetrahydrobenzo[2,1-b]pyrimidino[5,6-d]selenophene]-9-ylamine To a solution of step a compound (1.2 g, 4.22 mmol) in toluene (20 mL) was added sequentially acetic acid (0.2 mL) and DMF-DMA (0.7 mL, 5.08 mmol). The reaction mixture was stirred at 105° C. for 2 h and treated with 3-chloro-4-fluoroaniline (740 mg, 5.08 mmol) as described in example 12, gave the product as a pale yellow color oil (1.0 g, 53%). $^1$H NMR (400 MHz, CDCl$_3$): δ 8.44 (1H, s), 7.77 (1H, dd, J=6.4, 2.4 Hz), 7.39-7.43 (1H, m), 7.14 (1H, t, J=8.8 Hz), 7.07 (1H, s), 4.07 (4H, s), 3.26 (2H, t, J=6.3 Hz), 3.15 (2H, s), 2.12 (2H, t, J=6.3 Hz); LC-MS (positive ion mode): m/z 438, 440, 442 (M+H)$^+$.

Step c

4-[(3-Chloro-4-fluorophenyl)amino]-5,6,8-trihydrobenzo[2,1-b]pyrimidino[5,4-d]selenophen-7-one To a solution of step b compound (0.8 g) in THF (10 mL) was added 30% aqueous HCl (10 mL) and stirred at the same temperature for 16 h (solid separated). The reaction mixture was poured into ice cooled water and stirred for 30 min. The solution was basified with aqueous ammonia solution and extracted with ethyl acetate (3×200 mL). The combined organic layer was washed with water, brine and dried over sodium sulfate. The solution was filtered and evaporated the solvent. The residue was chromatographed over silica gel column using hexane:ethyl acetate (70:30) as eluents to give the product as a pale yellow color solid (500 mg, 70%), mp 228-230° C. IR (KBr) $v_{max}$ 3460, 1713, 1605, 1563, 1497, 1430, 1379, 1305, 1262, 1198, 1127, 1053, 964, 892, 801 cm$^{-1}$; $^1$H NMR (400 MHz, DMSO-d$_6$): δ 8.46 (1H, br s, exchangeable with D$_2$O), 8.41 (1H, s), 7.86 (1H, dd, J=6.4, 2.4 Hz), 7.56-7.61 (1H, m), 7.41 (1H, t, J=9.0 Hz), 3.83 (2H, s), 3.48 (2H, t, J=6.8 Hz), 2.70 (2H, t, J=6.8 Hz); $^{13}$C NMR (100 MHz, DMSO-d$_6$): δ 206.6, 171.8, 155.4, 153.3 (d, J=241 Hz), 151.7, 136.6 (d, J=3.0 Hz), 134.1, 128.5, 123.7, 122.6 (d, J=6.0 Hz), 119.1, 118.8 (d, J=18 Hz), 116.4 (d, J=22 Hz), 42.0, 37.7, 26.0; LC-MS (Negative ion mode): m/z 392, 394, 396 (M−H)$^-$.

Step d

HCl Salt:
The free base obtained above was dissolved in dioxane and treated a solution of HCl in dioxane as described in example 1, gave the salt, mp 236-240° C. LC-MS (negative ion mode): m/z 392, 394, 396 (M−HCl−H)$^-$.

Example 27

Synthesis of (3-chloro-4-fluorophenyl)-6,7,8,9-tetrahydrobenzo[1,2-d]pyrimidino[5,6-b]selenophen-4-ylamine (compd. No. 27)

Step a

Preparation of Sodium Selenide:
Selenium (1.5 g, 18.75 mmol) was added to a solution of sodium hydroxide (4.2 g, 105 mmol) and sodium formaldehyde sulfoxylate (6.93 g, 45 mmol) in water (18 mL). After stirring for 1 h at 50° C., the white precipitate was filtered under nitrogen atmosphere and rapidly used for the next step.

3-Amino-4,5,6,7-tetrahydrobenzo[1,2-b]selenophene-2-carbonitrile

To a suspension of sodium selenide (2.35 g, 18.65 mmol) in DMF (18 mL) was added a solution of 2-chlorocyclohex-1-enecarbonitrile (2.63 g, 18.65 mmol; Gunes, Y.; Polat, M. F.; Sahin, E.; Fleming, F. F.; Altundas, R. J. Org. Chem., 2010, 75, 7092-7098) in DMF (9 mL) at rt for 5 min and stirred the mixture at 60° C. for 45 min. Then chloroacetonitrile (1.18 mL, 18.65 mmol) was added dropwise to the reaction mixture and again stirred at 60° C. for 3 h. Then, a solution of sodium methoxide (1.0 g, 18.65 mmol) in dry methanol (18 mL) was added dropwise and stirring was continued for 2 h at the same temperature. The mixture was allowed to rt and poured into cold water and stirred for 30 min. The precipitated solid was filtered and washed with water to give the product as a dark brown color solid (2.4 g, 57%), mp 86-88° C.

Step b 3,6,7,8,9-Pentahydrobenzo[1,2-b]pyrimidino[4,5-d]selenophen-4-one

To a solution of step a compound (3.2 g) in formic acid (32 mL) was added concentrated sulfuric acid (12 mL) dropwise for 15 min. The reaction mixture was stirred at 90-100° C. for 1 h and allowed to rt. The reaction mixture was poured into ice cooled water and stirred for 15 min. The precipitated solid was filtered, washed with water and dried to give the product as a pale brown color solid (1.8 g, 50%), mp 316-318° C. $^1$H NMR (400 MHz, DMSO-d$_6$): δ 12.36 (1H, s), 8.14 (1H, s), 2.90 (2H, t, J=6.0 Hz), 2.64 (2H, t, J=6.0 Hz), 1.78-1.86 (4H, m); LC-MS (negative ion mode): m/z 251, 253 (M−H)$^-$.

Step c

4-Chloro-6,7,8,9-tetrahydrobenzo[1,2-d]pyrimidino[5,4-b]selenophene

A mixture of step b compound (1.1 g), thionyl chloride (11 mL) and catalytic amount of DMF (1 mL) was refluxed for 1 h. Work-up of the mixture as described in example 1, gave the product as a pale yellow color solid (700 mg, 59%), mp 114-116° C. $^1$H NMR (400 MHz, DMSO-d$_6$): δ 8.98 (1H, s), 3.02-3.05 (2H, m), 2.75-2.78 (2H, m), 1.82-1.94 (4H, m).

Step d (3-Chloro-4-fluorophenyl)-6,7,8,9-tetrahydrobenzo[1,2-d]pyrimidino[5,6-b]selenophenylamine To a solution of step c compound (700 mg, 2.57 mmol) in isopropanol (15 mL) was added 3-chloro-4-fluoroaniline (1.6 g, 11.56 mmol) at rt and the mixture was refluxed for 1.5 h. Work-up of the mixture as described in example 1, gave the product as an off-white color solid, mp 238-240° C. IR (KBr) $v_{max}$ cm$^{-1}$; $^1$H NMR (400 MHz, CDCl$_3$): δ 8.71 (1H, s), 7.70 (1H, dd, J=6.4, 2.8 Hz), 7.37-7.41 (1H, m), 7.16 (1H, t, J=8.8 Hz), 6.53 (1H, br s, exchangeable with D$_2$O), 2.92 (2H, t, J=6.0 Hz), 2.82 (2H, t, J=6.0 Hz), 1.86-1.99 (4H, m); $^{13}$C NMR (100 MHz, DMSO-d$_6$): δ 162.5, 156.2, 153.8, 153.0 (d, J=241 Hz), 148.6, 136.9 (d, J=3.0 Hz), 133.1, 122.7, 121.6 (d, J=7.0 Hz), 118.8 (d, J=19 Hz), 116.5 (d, J=21.0 Hz), 115.6, 27.6, 24.4, 23.5, 21.3; LC-MS (negative ion mode): m/z 378, 380, 382 (M−H)⁻.

Step e

HCl Salt:
To a solution of step d compound (70 mg) in dioxane (5 mL) was added HCl in dioxane and work-up as described in example 1, gave the product as a pale green color solid (70 mg), mp 290-292° C. LC-MS (positive ion mode): m/z 380, 382, 384 (M−HCl+H)⁺.

Example 28

Synthesis of [6-(tert-butyl)selenopheno[2,3-e]pyrimidin-4-yl](3-chloro-4-fluorophenyl)amine (compd. No. 28)

Step a

3-Amino-5-(tert-butyl)selenophene-2-carbonitrile

To a suspension of sodium selenide (3.51 g, 27.87 mmol) in DMF (28 mL) was added a solution of 3-chloro-4,4-dimethylpent-2-enenitrile (4.0 g, 27.87 mmol; Ohta, H.; Ishizaka, T.; Tatsuzuki, M.; Yoshinaga, M.; Iida, I.; Yamaguchi, T.; Tomishima, Y.; Futaki, N.; Toda, Y.; Saito, S. Bioorg. Med. Chem., 2008, 16, 1111-1124) in DMF (10 mL) at rt for 5 min and stirred the mixture at 60-70° C. for 2 h. Then chloroacetonitrile (1.76 mL, 27.87 mmol) was added dropwise to the reaction mixture and again stirred at 60-70° C. for 2 h. Then, a solution of sodium methoxide (1.5 g, 27.87 mmol) in dry methanol (18 mL) was added dropwise and stirring was continued for 1 h at the same temperature. The mixture was allowed to rt and poured into cold water and stirred for 30 min. The precipitated solid was filtered and washed with water. The solid was recrystallized from chloroform-hexane to give the product as a brown color solid (3.8 g, 60%), mp 110-112° C. (Thomae, D.; Kirsch, G.; Seck, P. Synthesis, 2008, 1600-1606). ¹H NMR (400 MHz, CDCl₃): δ 6.59 (1H, s), 4.46 (2H, br s), 1.33 (9H, s); LC-MS (negative ion mode): m/z 225, 227 (M−H)⁻.

Step c

3-Amino-5-(tert-butyl)selenophene-2-carboxamide

To a suspension of 3-amino-5-(tert-butyl)selenophene-2-carbonitrile (2.0 g) in aqueous sodium hydroxide solution (50 mL, 10%) was added ethanol (50 mL) and the mixture refluxed for 1 h. Ethanol was distilled off under vacuum and the mixture was allowed to cool to 5-10° C. The separated crystals were filtered off, washed with cold water and dried to give the product as an off-white color solid (1.8 g, 83%), mp 160-162° C. (Hesse, S.; Chenet, C.; Thomae, D.; Kirsch, G. Synthesis, 2009, 1204-1208). ¹H NMR (400 MHz, CDCl₃): δ 6.58 (1H, s), 5.75 (2H, br s), 5.13 (2H, br s), 1.34 (9H, s).

Step d 6-(tert-Butyl)-3-hydroselenopheno[3,2-d]pyrimidin-4-one

To a solution of 3-amino-5-(tert-butyl)selenophene-2-carboxamide (1 g) in formic acid (10 mL) was added concentrated sulfuric acid (5 mL) slowly for 10 min at rt. The mixture was refluxed for 1.5 h and allowed to rt. The mixture was poured into ice cold water and basified with ammonia solution. The solution was extracted with chloroform (3×200 mL) and the combined chloroform layer was washed with water, brine and dried over sodium sulfate. The solution was filtered and evaporated the solvent to give the product as a yellow color solid (550 mg, 53%), mp 240-242° C. ¹H NMR (400 MHz, CDCl₃): δ 12.61 (1H, br s), 8.16 (1H, s), 7.34 (1H, s), 1.46 (9H, s); LC-MS (negative ion mode): m/z 253, 255 (M−H).

Step e 6-(tert-Butyl)-4-chloroselenopheno[3,2-d]pyrimidine

A mixture of 6-(tert-butyl)-3-hydroselenopheno[3,2-d]pyrimidin-4-one (550 mg), thionyl chloride (6 mL) and catalytic amount of DMF (0.5 mL) was refluxed for 2 h. Work-up of the mixture as described in example 1, gave the product as a pale yellow color solid (400 mg, 68%), mp 78-80° C. ¹H NMR (400 MHz, CDCl₃): δ 8.91 (1H, s), 7.51 (1H, s), 1.49 (9H, s).

Step f

[6-(tert-Butyl)selenopheno[2,3-e]pyrimidin-4-yl](3-chloro-4-fluorophenyl)amine

To a solution of 6-(tert-butyl)-4-chloroselenopheno[3,2-d]pyrimidine (0.4 g, 1.45 mmol) in isopropanol (20 mL) was added 3-chloro-4-fluoroaniline (0.83 g, 5.8 mmol) at rt and the mixture was refluxed for 2 h. Work-up of the mixture as described in example 1, gave the product as a white color solid (0.52 g, 94%), mp 204-206° C. IR (KBr) ν$_{max}$ 3440, 3270, 3095, 2958, 1621, 1596, 1260, 1207, 1044, 808 cm⁻¹; ¹H NMR (400 MHz, CDCl₃): δ 8.66 (1H, s), 7.68 (1H, dd, J=6.4, 2.8 Hz), 7.35-7.39 (1H, m), 7.34 (1H, s), 7.24 (1H, br s, exchangeable with D₂O), 7.16 (1H, t, J=8.8 Hz), 1.42 (9H, s); ¹³C NMR (100 MHz, CDCl₃): δ 172.1, 164.9, 157.1, 155.7 (d, J=246 Hz), 154.8, 134.4 (d, J=3.0 Hz), 126.2, 123.7 (d, J=6.0 Hz), 122.6, 121.3 (d, J=22 Hz), 115.5, 37.2, 32.4; LC-MS (negative ion mode): m/z 380, 382, 384 (M−H)⁻.

Step g

HCl Salt:
To a solution of step f compound (120 mg) in dioxane (10 mL) was added HCl in dioxane and work-up as described in example 1, gave the product as a white color solid (100 mg). LC-MS (negative ion mode): m/z 380, 382 (M−H—HCl)⁻.

Example 29

Synthesis of (3-chloro-4-fluorophenyl)(6-phenylselenopheno[2,3-e]pyrimidin-4-yl)amine (compd. No. 29)

Step a

6-Phenyl-3-hydroselenopheno[3,2-d]pyrimidin-4-one

To a solution of 3-amino-5-phenylselenophene-2-carboxamide (1.5 g; Hesse, S.; Chenet, C.; Thomae, D.; Kirsch, G. Synthesis, 2009, 1204-1208) in formic acid (30 mL) was added concentrated sulfuric acid (10 mL) slowly for 10 min at rt. The mixture was refluxed for 3 h and allowed to rt. The mixture was poured into ice cold water and basified with ammonia solution. The solution was stirred for 10 min and the precipitated solid was filtered, washed with ice cold water and dried. The crude product was further recrystallized from methanol-chloroform-hexane to give the product as a white color crystalline solid (1.0 g, 53%), mp 266-268° C. $^1$H NMR (400 MHz, DMSO-$d_6$): δ 12.50 (1H, br s), 8.19 (1H, s), 8.01 (1H, s), 7.80-7.82 (2H, m), 7.47-7.49 (3H, m); LC-MS (positive ion mode): m/z 297, 299 (M+Na)$^+$.

Step b (3-Chloro-4-fluorophenyl)(6-phenylselenopheno[2,3-e]pyrimidin-4-yl)amine

A mixture of 6-phenyl-3-hydroselenopheno[3,2-d]pyrimidin-4-one (1.0 g), thionyl chloride (20 mL) and small amount of DMF (1.0 mL) was refluxed for 2 h. Solvents were removed under vacuum and the mixture was diluted with chloroform. Again the solvents were removed under vacuum and this procedure repeated twice (green color solid). This solid (1.0 g, 3.395 mmol) was dissolved in isopropanol (50 mL) and added 3-chloro-4-fluoroaniline (1.97 g, 13.58 mmol) at rt. The mixture was refluxed for 4 h and allowed to rt. Work-up of the mixture as described in example 1, gave the product as a white color solid (500 mg, 36%), mp 244-246° C. IR (KBr) $v_{max}$ 3430, 2928, 1623, 1563, 1482, 1451, 1411, 1384, 1257, 1208, 1033, 870 cm$^{-1}$; $^1$H NMR (400 MHz, CDCl$_3$+DMSO-$d_6$): δ 9.10 (1H, s, exchangeable with D$_2$O), 8.65 (1H, s), 7.94 (1H, dd, J=6.8, 2.8 Hz), 7.78 (1H, s), 7.65-7.69 (3H, m), 7.40-7.48 (3H, m), 7.14 (1H, t, J=8.8 Hz); $^{13}$C NMR (100 MHz, CDCl$_3$+DMSO-$d_6$): δ 164.2, 156.8, 154.9, 154.7, 154.3 (d, J=244 Hz), 135.9 (d, J=3.0 Hz), 134.9, 129.4, 129.1, 126.7, 124.2, 123.6, 122.1 (d, J=6.0 Hz), 120.2 (d, J=18 Hz), 117.5, 116.1 (d, J=22 Hz); LC-MS (positive ion mode): m/z 402, 404, 406 (M+H)$^+$.

Step c

HCl Salt:

To a solution of step b compound (150 mg) in dioxane (10 mL) was added HCl in dioxane and work-up as described in example 1, gave the product as a yellow color solid (130 mg), mp 296-306° C. LC-MS (positive ion mode): m/z 402, 404, 406 (M–HCl+H)$^+$.

Example 30

Synthesis of benzo[d]pyrimidino[5,6-b]selenophen-4-yl(3-chloro-4-fluorophenyl)amine (compd. No. 30)

Step a

3-Aminobenzo[b]selenophene-2-carbonitrile

To a suspension of sodium selenide (9.14 g, 72.6 mmol) in DMF (72 mL) was added a solution of 2-chlorobenzonitrile (10 g, 72.6 mmol) in DMF (25 mL) at rt for 5 min and stirred the mixture at 100-110° C. for 24 h. Then chloroacetonitrile (5.48 mL, 72.6 mmol) was added dropwise to the reaction mixture and again stirred at 60-70° C. for 2 h. Then, a solution of sodium methoxide (3.9 g, 72.6 mmol) in dry methanol (24 mL) was added dropwise and stirring was continued for 2 h at the same temperature. The mixture was allowed to rt and poured into cold water and stirred for 30 min. The precipitated solid was filtered, washed with water and dried to give the product as an off-white color solid (9.5 g, 59%), mp 157-159° C.

Step b

Benzo[d]pyrimidino[5,6-b]selenophen-4-yl(3-chloro-4-fluorophenyl)amine

To a solution of step-a compound (2.0 g, 9.0 mmol) in toluene (50 mL) was added sequentially acetic acid (0.4 mL) and DMF-DMA (2.72 mL, 18.9 mmol). The reaction mixture was stirred at 105° C. for 3 h. and treated with 3-chloro-4-fluoroaniline (740 mg, 5.08 mmol) as described in example 12, gave the product as an off-white color solid (1.4 g, 41%), mp 210-212° C. IR (KBr) $v_{max}$ 3430, 3272, 3123, 1613, 1568, 1494, 1444, 1397, 1264, 1203, 1034, 961, 810, 747 cm$^{-1}$; $^1$H NMR (400 MHz, DMSO-$d_6$): δ 9.74 (1H, s, exchangeable with D$_2$O), 8.78 (1H, s), 8.39 (1H, d, J=7.6 Hz), 8.28 (1H, d, J=7.6 Hz), 8.14-8.16 (1H, m), 7.77-7.79 (1H, m), 7.59-7.67 (2H, m), 7.45 (1H, t, J=9.2 Hz); $^{13}$C NMR (100 MHz, DMSO-$d_6$): δ 159.4, 157.2, 154.5, 153.3 (d, J=241.0 Hz), 140.4, 136.5 (d, J=3.0 Hz), 136.3, 129.9, 126.7, 125.6, 124.7, 123.3, 122.1 (d, J=7.0 Hz), 118.9 (d, J=18.0 Hz), 116.6 (d, J=22.0 Hz), 116.1; LC-MS (negative ion mode): m/z 374, 376, 378 (M–H)$^-$.

Step c

HCl Salt:

To a solution of step b compound (300 mg) in dioxane (10 mL) was added HCl in dioxane and work-up as described in example 1, gave the product as a pale-yellow color solid (250 mg), mp 278-280° C. LC-MS (negative ion mode): m/z 374, 376, 378 (M–HCl–H)$^-$.

Example 31

Synthesis of (3-chloro-4-fluorophenyl)pyrimidino[4',5'-5,4]selenopheno[2,3-b]pyridin-4-ylamine (compd. No. 31)

Step a

3-Aminoselenopheno[2,3-b]pyridine-2-carbonitrile

To a suspension of sodium selenide (0.9 g, 7.2 mmol) in DMF (7 mL) was added a solution of 2-chloropyridine-3-carbonitrile (1 g, 7.2 mmol) in DMF (3 mL) at rt for 5 min and stirred the mixture at 60-70° C. for 2 h. Then chloroacetonitrile (0.46 mL, 7.22 mmol) was added dropwise to the reaction mixture and again stirred at 60-70° C. for 2 h. Then, a solution of sodium methoxide (0.39 g, 7.2 mmol) in methanol (7 mL) was added dropwise and stirring was continued for 1 h at the same temperature. The mixture was allowed to rt and poured into cold water and stirred for 15 min. The precipitated solid was filtered, washed with water and dried to give the product as a yellow color solid (1.2 g, 75%), mp 208-210° C.

Step b (3-Chloro-4-fluorophenyl)pyrimidino[4',5'-5,4]selenopheno[2,3-b]pyridin-4-ylamine To a solution of 3-aminoselenopheno[2,3-b]pyridine-2-carbonitrile (0.5 g, 2.24 mmol) in toluene (10 mL) was added sequentially acetic acid (0.1 mL) and DMF-DMA (0.65 mL, 4.84 mmol). The reaction mixture was stirred at 105° C. for 3 h. and treated with 3-chloro-4-fluoroaniline (740 mg, 5.08 mmol) as described in example 12, gave the product as an off-white color solid, mp 262-266° C. IR (KBr) $v_{max}$ 3436, 3257, 1618, 1571, 1493, 1448, 1389, 1265, 1034, 963, 864, 813, 772 cm$^{-1}$; $^1$H NMR (400 MHz, DMSO-d$_6$): δ 9.79 (1H, s, exchangeable with D$_2$O), 8.80 (1H, dd, J=4.6, 1.8 Hz), 8.77 (1H, s), 8.61 (1H, dd, J=7.8, 1.8 Hz), 8.14 (1H, dd, J=6.8, 2.4 Hz), 7.73-7.77 (1H, m), 7.64 (1H, dd, J=7.8, 4.6 Hz), 7.43 (1H, t, J=9.2 Hz); $^{13}$C NMR (100 MHz, DMSO-d$_6$): δ 163.6, 156.9, 156.8, 154.8, 153.4 (d, J=242 Hz), 151.7, 136.3 (d, J=3.0 Hz), 132.6, 130.7, 123.6, 122.1 (d, J=6.0 Hz), 121.2, 118.9 (d, J=19.0 Hz), 116.6 (d, J=22.0 Hz), 115.8; LC-MS (negative ion mode): m/z 375, 377, 379 (M−H)$^-$.

Step c

HCl Salt:

To a solution of step b compound (200 mg) in methanol (10 mL) was added HCl in dioxane until the pH paper showed red color (1 mL) at rt. Work-up of the reaction mixture as described in example 1, gave the product as an off-white color solid, mp 294-298° C. LC-MS (negative ion mode): m/z 375, 377, 379 (M−HCl−H)$^-$.

Example 32

Synthesis of ethyl 4-[(3-chloro-4-fluorophenyl)amino]-5-methylthioselenopheno[3,4-d]pyrimidine-7-carboxylate (compd. No. 32)

Step a

Ethyl 3-amino-4-cyano-5-methylthioselenophene-2-carboxylate

To a suspension of sodium selenide (4.6 g, 37.5 mmol) in DMF (37 mL) was added a solution of 2-[bis(methylsulfanyl)methylene]malononitrile (6.37 g, 37.5 mmol; Baraldi, P. G.; Fruttarolo, F.; Tabrizi, M. A.; Preti, D.; Romagnoli, R.; El-Kashef, H.; Moorman, A.; Varani, K.; Gessi, S.; Merighi, S.; Borea, P. A. J. Med. Chem., 2003, 46, 1229-1241; Thomae, D.; Perspicace, E.; Henryon, D.; Xu, Z.; Schneider, S.; Hesse, S.; Kirsch, G.; Seck, P. Tetrahedron, 2009, 65, 10453-10458) in DMF (18 mL) at rt for 5 min and stirred the mixture at 70-80° C. for 2 h. Then ethyl chloroacetate (6.38 mL, 75 mmol) was added dropwise to the reaction mixture and again stirred at 70-80° C. for 2 h. Then, a suspension of sodium methoxide (2.0 g, 37.5 mmol) in methanol (37 mL) was added and stirring was continued for 1.5 h at the same temperature. The mixture was allowed to rt and poured into cold water and stirred for 15 min. The solution was extracted with chloroform (3×100 mL). The combined organic layer was washed with water, brine and dried over sodium sulfate. The solution was filtered and evaporated the solvent. The residue was chromatographed over silica gel column using hexane-ethyl acetate (90:10) as eluents to give the product as a brown color solid (2.2 g, 21%), mp 128-130° C. $^1$H NMR (400 MHz, CDCl$_3$): δ 5.86 (2H, br s), 4.27 (2H, q, J=7.06 Hz), 2.67 (3H, s), 1.32 (3H, t, J=7.0 Hz); LC-MS (positive ion mode): m/z 289, 291 (M+H)$^+$.

Step b

Ethyl 4-[(3-chloro-4-fluorophenyl)amino]-5-methylthioselenopheno[3,4-d]pyrimidine-7-carboxylate To a solution of ethyl 3-amino-4-cyano-5-methylthioselenophene-2-carboxylate (1.0 g, 3.45 mmol) in toluene (30 mL) was added sequentially acetic acid (0.2 mL) and DMF-DMA (1.0 mL, 7.45 mmol). The reaction mixture was stirred at 105° C. for 3 h and treated with 3-chloro-4-fluoroaniline (740 mg, 5.08 mmol) as described in example 12, gave the product as a pale pink color solid (1.1 g, 72%), mp 176-178° C. IR (KBr) ν$_{max}$ 3344, 1643, 1609, 1568, 1487, 1425, 1401, 1292, 1259, 1237, 1201, 1099, 1048 cm$^{-1}$; $^1$H NMR (400 MHz, DMSO-d$_6$): δ 11.34 (1H, s, exchangeable with D$_2$O), 7.74 (1H, d, J=3.6 Hz), 7.26-7.31 (2H, m), 7.03-7.07 (1H, m), 4.32 (2H, q, J=7.06 Hz), 2.63 (3H, s), 1.32 (3H, t, J=7.0 Hz); LC-MS (positive ion mode): m/z 444, 446, 448 (M+H)$^+$.

Step c

HCl Salt:

To a solution of step b compound (100 mg) in dichloromethane (5 mL) was added HCl in dioxane until the pH paper showed red color (0.5 mL) at rt. Work-up of the reaction mixture as described in example 1, gave the product as a yellow color solid (70 mg), mp 200-202° C. LC-MS (negative ion mode): m/z 442, 444, 446 (M−HCl−H)$^-$.

Example 33

Synthesis of (4-chlorophenyl)methyl-5,6,7,8-tetrahydropyrimidino[5',6'-5,4]selenopheno[2,3-c]pyridin-4-ylamine (compd. No. 33)

Step a (4-Chlorophenyl)methyl-5,6,7,8-tetrahydropyrimidino[5',6'-5,4]selenopheno[2,3-c]pyridin-4-ylamine To a solution of N-Boc-2-amino-4,5,6,7-tetrahydroselenopheno[2,3-c]pyridine-3-carbonitrile (3.0 g, 9.24 mmol, from step b of example 18) in toluene (30 mL) was added sequentially acetic acid (0.3 mL) and DMF-DMA (2.80 mL, 19.325 mmol). The reaction mixture was stirred at 105° C. for 3 h and treated with 4-chloro-N-methylaniline (0.92 mL, 11.04 mmol) as described in example 12, gave the product as a pale yellow color solid, mp 186-188° C. $^1$H NMR (400 MHz, CDCl$_3$): δ 7.92 (1H, s), 7.39 (2H, d, J=8.4 Hz), 7.12 (2H, d, J=8.4 Hz), 3.91 (2H, s), 3.54 (3H, s), 3.16 (2H, t, J=5.7 Hz), 2.62 (2H, t, J=5.7 Hz); $^{13}$C NMR (100 MHz, CDCl$_3$): δ 168.6, 152.0, 142.7, 133.2, 131.4, 130.0, 129.8, 122.2, 116.0, 102.8, 46.6, 42.9, 35.5, 27.1; LC-MS (positive ion mode): m/z 377, 379, 381 (M+H)$^+$.

Step b

HCl Salt:

To a solution of step a compound (80 mg) in dioxane (8 mL) was added HCl in dioxane until the pH paper showed red color (0.5 mL) at rt. Work-up of the reaction mixture as described in example 1, gave the product as a yellow color solid (60 mg), mp 274-276° C. LC-MS (positive ion mode): m/z 377, 379, 381 (M−HCl+H)$^+$.

Example 34

Synthesis of (3-chloro-4-fluorophenyl)(2-methyl(5,6,7,8-tetrahydrobenzo[1,2-b]pyrimidino[5,6-d]selenophen-4-yl)amine (compd. No. 34)

Step a

2-Methyl-3,5,6,7,8-pentahydrobenzo[1,2-b]pyrimidino[5,4-d]selenophen-4-one

Dry HCl gas was passed (until the clear solution observed) to a solution of ethyl 2-amino-4,5,6,7-tetrahydrobenzo[1,2- b]selenophene-3-carboxylate (4.0 g, 14.65 mmol; Aumann, K. M.; Scammells, P. J.; White, J. M.; Schiesser, C. H. Org. Biomol. Chem., 2007, 5, 1276-1281) in acetonitrile (100 mL) for 30 min at rt. The reaction mixture was refluxed for 5 h and attained to rt. The solid precipitated was filtered and the solid was dissolved in water. The solution was neutralized with 10% aqueous NaHCO₃ and the precipitated solid was filtered, washed with ice cold water and dried to give the product as an off-white color solid (1.4 g, 36%), mp 284-286° C. $^1$H NMR (400 MHz, CDCl₃): δ 12.36 (1H, br s, —NH), 3.02 (2H, br s, H-8), 2.85 (2H, br s, H-5), 2.50 (3H, s, —CH3), 1.87 (4H, br s, H-6,7); LC-MS (negative ion mode): m/z 265, 267 (M–H)⁻.

Step b

4-Chloro-2-methyl-5,6,7,8-tetrahydrobenzo[1,2-b]pyrimidno[5,4-d]selenophene

A mixture of 2-methyl-3,5,6,7,8-pentahydrobenzo[1,2-b]pyrimidino[5,4-d]selenophen-4-one (1.4 g) and phosphorous oxychloride (15 mL) was refluxed for 2 h. The reaction mixture was attained to rt and poured into ice cold water and stirred for 10 min. The precipitated solid was filtered, washed with ice cold water and dried to give the product as a brown color solid (1.3 g, 87%), mp 106-108° C. $^1$H NMR (400 MHz, CDCl₃): δ 3.05-3.08 (2H, m, H-8), 2.92-2.93 (2H, m, H-5), 2.73 (3H, s, —CH₃), 1.89-1.93 (4H, m, H-6,7).

Step c (3-Chloro-4-fluorophenyl)(2-methyl(5,6,7,8-tetrahydrobenzo[1,2-b]pyrimidino[5,6-d]selenophen-4-yl)amine To a solution of 4-chloro-2-methyl-5,6,7,8-tetrahydrobenzo[1,2-b]pyrimidno[5,4-d]selenophene (500 mg, 3.496 mmol) in IPA (12 mL) was added 3-chloro-4-fluoroaniline (1.5 g, 10.489 mmol) at rt and the mixture was refluxed for 6 h. The precipitated solid was filtered, washed with water and purified as described earlier to give the product as an off-white color solid (450 mg, 65%), 136-138° C. $^1$H NMR (400 MHz, CDCl₃): δ 7.85-7.86 (1H, m, H-5'), 7.45-7.47 (1H, m, H-2'), 7.09-7.12 (1H, m, H-6'), 7.09 (1H, s, exchangeable with D₂O, —NH), 3.00 (2H, br s, H-8), 2.90 (2H, br s, H-5), 2.59 (3H, s, —CH₃), 1.97-1.98 (2H, br s, H-6), 1.91-1.92 (2H, br s, H-7); $^{13}$C NMR (100 MHz, CDCl₃): δ 171.8, 161.3, 154.9, 154.2 (d, J=244.0 Hz), 138.4, 135.6 (d, J=4.0 Hz), 126.4, 122.8, 120.8 (d, J=18.0 Hz), 120.3 (d, J=7.0 Hz), 117.0, 116.4 (d, J=22.0 Hz), 28.3, 27.9, 25.5, 22.8, 22.6; LC-MS (positive ion mode): m/z 394, 396, 398 (M+H)⁺.

Step d

HCl Salt:

To a solution of step c compound (100 mg) in dioxane (5 mL) was added HCl in dioxane until the pH paper showed red color (0.5 mL) at rt. Work-up of the reaction mixture as described in example 1, gave the product as a white color solid (80 mg), mp 266-268° C. LC-MS (negative ion mode): m/z 392, 394, 396 (M–HCl–H)⁻.

Example 35

Determination of Anti-Cancer Activity Using MTT Based Cell Proliferation Assay:

MTT [3-(4,5-dimethylthiazol-2-yl)-2,5-diphenyltetrazolium bromide incorporation based cell proliferation assay was performed using standard procedure. The cytotoxic efficacy of the test compounds (Compound nos. 1 to 34) was evaluated in either human lung carcinoma A549 cells or human colorectal carcinoma HT29 cells or human prostate DU145 cells or human breast carcinoma (estrogen receptor negative) MDA-MB-231 cells or human Hepatocellular carcinoma HepG2 cells or human cervical carcinoma HeLa cells by MTT cell proliferation assay kit (Roche Applied Sciences, Germany). The assay was carried out according to the instructions provided by the vendor. Briefly, equal numbers of cells was plated in 96-well flat-bottomed plates and were incubated with 4-selenophenylaminopyrimidine compounds of formula (I) or gefitinib (Iressa) at different concentrations for a period of three days. Vehicle control culture wells received only a maximum of 0.5% DMSO. Thereafter, 0.5 mg/ml of MTT reagent was added to each well and the microplate was incubated further for 4 h at 37° C. in presence of 5% CO₂. Finally, the cells were solubilized by adding solubilizing solution and allowed to incubate at 37° C. overnight. After complete solubilization of the formazan crystals the absorbance was read at 540 nm in a microplate reader (BioRad, USA). The results (mean OD±SD) obtained from quadruplicate wells were used in calculation to determine the inhibition of cell proliferation (50% of inhibitory concentration, IC₅₀) of the test compounds.

The evaluation of cell proliferation inhibitory activities of the compounds was done in two phases—(1) Screening, and (2) half-maximal inhibitory concentration (IC50) determination. In the screening phase, the cells were treated with different concentrations. Thereafter, the best active test compounds were selected for IC50 determination. The cell proliferation inhibitory potentials of the test Compounds (1 to 34) on different cell lines are summarized in Table 1. Results are presented in micromolar concentrations of the tested compounds. The cell proliferation inhibitory activities of Gefitinib (Iressa) are also presented for comparison.

TABLE 1

Tumor cell Proliferation inhibitory activities of Compound 1 to Compound 34

| | Cell proliferation inhibition in | | |
|---|---|---|---|
| Compounds | A549 (Lung carcinoma) | DU145 (Prostate carcinoma) | HT29 (Colon carcinoma) |
| Compound 1 | IC50 at 33.49 μM | IC50 at 8.37 μM | IC50 at 117.46 μM |
| Compound 2 | 20.66% at 22.421 μM | 13.13% at 22.421 μM | 11.09% at 22.421 μM |
| Compound 3 | 15.59% at 22.935 μM | 18.34% at 22.935 μM | 13.85% at 22.935 μM |
| Compound 4 | IC50 at 42.34 μM | IC50 at 37.08 μM | IC50 at 161.72 μM |
| Compound 5 | IC50 at 15.0 μM | IC50 at 16.43 μM | IC50 at 37.86 μM |

TABLE 1-continued

Tumor cell Proliferation inhibitory activities of Compound 1 to Compound 34

| Compounds | Cell proliferation inhibition in | | |
|---|---|---|---|
| | A549 (Lung carcinoma) | DU145 (Prostate carcinoma) | HT29 (Colon carcinoma) |
| Compound 6 | IC50 at 48.96 µM | IC50 at 42.37 µM | 15.49% at 18.868 µM |
| Compound 7 | IC50 at 44.05 µM | IC50 at 110.79 µM | IC50 at 9.298 µM |
| Compound 10 | IC50 at 82.58 µM | IC50 at 42.48 µM | IC50 at 39.14 µM |
| Compound 12 | IC50 at 21.8 µM | IC50 at 26.8 µM | 15.56% at 24.449 µM |
| Compound 13 | IC50 at 15 µM | IC50 at 41.597 µM | IC50 at 37.857 µM |
| Compound 14 | IC50 at 121.488 uM | IC50 at 105.104 uM | Not done |
| Compound 15 | 25.03% at 240.539 µM | 41.21% at 240.539 µM | 18.94% at 240.539 µM |
| Compound 16 | IC50 at 44.052 µM | IC50 at 110.793 µM | 38.58% at 66.079 µM |
| Compound 17 | 21.39% at 25 µM | 44.43% at 25 µM | Not done |
| Compound 18 | IC50 at 82.577 µM | IC50 at 42.482 µM | IC50 at 39.141 µM |
| Compound 19 | 27.38% at 25 µM | 29.25% at 25 µM | 3.07% at 25 µM |
| Compound 20 | 0.45% at 22.421 µM | 13.43% at 22.421 µM | 8.96% at 22.421 µM |
| Compound 21 | 11.6% at 25.575 µM | 12.93% at 25.575 µM | 4.66% at 25.575 µM |
| Compound 22 | 16.67% at 22.935 µM | 36.62% at 22.935 µM | 28.39% at 22.935 µM |
| Compound 23 | 8.64% at 22.472 µM | 5.08% at 22.472 µM | 15.36% at 22.472 µM |
| Compound 25 | 0.19% at 19.92 µM | IC50 at 8.512 µM | IC50 at 9.243 µM |
| Compound 26 | 17.49% at 23.148 µM | 65.09% at 23.148 µM | 30.94% at 23.148 µM |
| Compound 27 | IC50 at 33.492 µM | IC50 at 11.442 µM | IC50 at 117.464 µM |
| Compound 28 | IC50 at 108.695 µM | IC50 at 82.673 µM | IC50 at 70.952 µM |
| Compound 29 | 45.48% at 30 µM | 30.81% at 25 µM | 43.09% at 25 µM |
| Compound 30 | IC50 at 21.8 µM | IC50 at 26.8 µM | 38.1% at 25 µM |
| Compound 31 | 30.16% at 25 µM | 22.01% at 25 µM | 5.21% at 25 µM |
| Compound 32 | 26.1% at 25 µM | 9.75% at 25 µM | 12.97% at 25 µM |
| Compound 33 | IC50 at 28.378 µM | IC50 at 29.474 µM | IC50 at 13.11 µM |
| Gefitinib (Iressa) | IC50 at 57.1 µM | IC50 at 31.47 µM | IC50 at 46.9 µM |

Next, based on the consistency and the highest anti-cell proliferation activities in A549, DU145 and HT-29 cells, compound 33 was further selected for evaluating its inhibitory activities on cell proliferation in some other human cancer cells such as breast carcinoma (estrogen receptor negative) MDA-MB-231 cells or hepatocarcinoma HepG2 cells or cervical carcinoma HeLa cells. The cell proliferation inhibitory activities of Gefitinib (Iressa) are also presented for comparison (Table 2).

TABLE 2

Tumor cell proliferation inhibitory activities of Compound 33

| Compounds | Cell proliferation inhibition (IC50) in | | |
|---|---|---|---|
| | MDA-MB-231 (Breast Carcinoma) | HepG2 (Hepatocellular Carcinoma) | HeLa (Cervical Carcinoma) |
| Compound 33 | 20.45 µM | 10.41 µM | 23.09 µM |
| Gefitinib (Iressa) | 45.40 µM | 35.53 µM | 50.12 µM |

We claim:
1. A selenophene compound of formula (I)

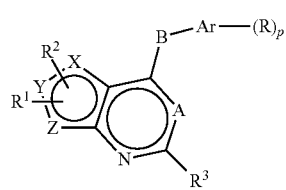

wherein X, Y, and Z are independently selected from the group consisting of selenium and carbon, with the proviso that one of X, Y, and Z is selenium;

A is N or C—$R^4$, wherein $R^4$ is selected from the group consisting of hydrogen, halogen, hydroxy, formyl, carboxylic acid, amino, nitro, cyano, sulfonic acid, thiole, trihalomethyl, sulfonamide, $C_{1-6}$ alkyl, $C_{1-6}$ secondary alkyl, $C_{1-6}$ tertiary alkyl, $C_{2-6}$ alkenyl, $C_{2-6}$ alkynyl, $C_{1-4}$ alkylcarbonyl, $C_{1-4}$ alkoxycarbonyl, aminocarbonyl, $C_{1-6}$ alkylaminocarbonyl, di($C_{1-6}$ alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$ cycloalkyl, $C_{3-7}$ cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, and $C_{1-6}$ alkylsulfonyl;

B is $NR^5$; wherein $R^5$ is selected from the group consisting of hydrogen, alkyl, alkoxy and haloalkyl;

Ar is selected from the group consisting of an optionally substituted benzene ring, an optionally substituted napththalene ring; an optionally substituted 6-membered aromatic ring containing one, two or three nitrogen atoms; and an optionally substituted 5-membered aromatic ring containing at least one heteroatom selected from the group consisting of sulfur, oxygen, and nitrogen, with the proviso that said 5-membered aromatic ring contains no more than one oxygen or sulfur atom;

p is 0, 1, 2, 3, 4, or 5;

R and $R^3$ are independently selected from the group consisting of hydrogen, halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$ alkenyl, $C_{2-6}$ alkynyl, $C_{1-4}$ alkyl carbonyl, $C_{1-4}$ alkoxycarbonyl, aminocarbonyl, $C_{1-6}$ alkylaminocarbonyl, di($C_{1-6}$alkyl)aminocarbonyl, $C_{1-6}$haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$cycloalkyl, $C_{3-7}$cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, $C_{1-6}$ alkylsulfonyl, an optionally substituted aryl ring, an optionally substituted heteroaryl ring, and an optionally substituted heterocycloalkyl ring;

$R^1$ and $R^2$ are:

a) independently selected from the group consisting of hydrogen, halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$ alkenyl, $C_{2-6}$alkynyl, $C_{1-4}$ alkyl carbonyl, $C_{1-4}$ alkoxycarbonyl, aminocarbonyl, $C_{1-6}$ alkylaminocarbonyl, di($C_{1-6}$alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$cycloalkyl, $C_{3-7}$ cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, $C_{1-6}$ alkylsulfonyl, an optionally substituted aryl ring, an optionally substituted heteroaryl ring, an optionally substituted heterocycloalkyl ring, and a group having the formula:

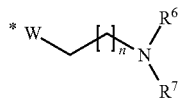

wherein n is 0, 1, 2, 3, 4, or 5; * indicates the point of attachment to the selenophene ring in formula I; W is selected from the group consisting of $CH_2$, O, S, or NH; $R^6$ and $R^7$ are independently selected from the group consisting of hydrogen, amino, trihalomethyl, $C_{1-6}$ alkyl, $C_{1-6}$ secondary alkyl, $C_{1-6}$ tertiary alkyl, $C_{2-6}$alkenyl, $C_{2-6}$alkynyl, $C_{1-4}$ alkylcarbonyl, $C_{1-4}$ alkoxycarbonyl, aminocarbonyl, $C_{1-6}$ alkylaminocarbonyl, di($C_{1-6}$alkyl)aminocarbonyl, $C_{1-6}$haloalkyl, $C_{1-6}$ hydroxyalkyl, $C_{1-6}$alkoxy, $C_{1-6}$ haloalkoxy, $C_{1-6}$ hydroxyalkoxy, $C_{3-7}$cycloalkyl, $C_{3-7}$cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ [($C_{1-6}$ alkylamino)alkyl, $C_{1-6}$ [di($C_{1-6}$alkyl)amino]alkyl; or b) $R^1$ and $R^2$ are joined to form a group having the formula;

wherein m and o are independently 0, 1, 2, 3 or 4; * indicates the point of attachment to the selenophene ring in formula I; L is selected from $CH_2$, O, S and $NR^8$; and $R^8$ is selected from the group consisting of hydrogen, amino, trihalomethyl, $C_{1-6}$ alkyl, $C_{1-6}$ secondary alkyl, $C_{1-6}$ tertiary alkyl, $C_{2-6}$alkenyl, $C_{2-6}$alkynyl, $C_{1-4}$ alkylcarbonyl, $C_{1-4}$ alkoxycarbonyl, aminocarbonyl, $C_{1-6}$ alkylaminocarbonyl, di($C_{1-6}$alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$cycloalkyl, $C_{3-7}$cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, and a group of the formula:

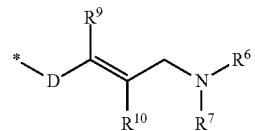

wherein * indicates the point of attachment to N in $NR^8$; D is selected from the group consisting of $C_{1-6}$alkyl, C(O), S(O), and $S(O)_2$; and $R^9$ and $R^{10}$ are selected from the group consisting of hydrogen, halogen, hydroxy, formyl, carboxylic acid, amino, nitro, cyano, sulfonic acid, thiol, trihalomethyl, sulfonamide, $C_{1-6}$alkyl, $C_{1-6}$secondary alkyl, $C_{1-6}$ tertiary alkyl, $C_{2-6}$alkenyl, $C_{2-6}$alkynyl, $C_{1-4}$ alkylcarbonyl, $C_{1-4}$ alkoxycarbonyl, aminocarbonyl, $C_{1-6}$ alkylaminocarbonyl, di($C_{1-6}$ alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$cycloalkyl, $C_{3-7}$cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$ alkyl)amino]alkyl, $C_{1-6}$ alkylsulfinyl, and $C_{1-6}$ alkylsulfonyl; and $R^6$ and $R^7$ are joined, and taken together with the atom to which they are attached, form a 5- to 7-membered optionally substituted cycloalkyl or cycloheteroalkyl ring; or c) $R^1$ and $R^2$ are joined, and taken together with the atoms to which they are attached, form an optionally substituted aryl ring, an optionally substituted 6-membered aromatic ring containing one, two or three nitrogen atoms; or an optionally substituted 5-membered aromatic ring containing one or more heteroatoms selected from the group consisting of sulfur, oxygen, and nitrogen, with the proviso that no more than one oxygen or sulfur atom is present;

wherein each optionally substituted ring is optionally substituted by halogen, hydroxy, formyl, carboxylic acid, amino, nitro, cyano, sulfonic acid, thiol, trihalomethyl, sulfonamide, $C_{1-6}$ alkyl, $C_{2-6}$alkenyl, $C_{2-6}$alkynyl, $C_{1-4}$alkylcarbonyl, $C_{1-4}$ alkoxy-carbonyl, aminocarbonyl, $C_{1-6}$ alkylaminocarbonyl, di($C_{1-6}$ alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$ cycloalkyl, $C_{3-7}$cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, or $C_{1-6}$ alkylsulfonyl.

2. The selenophene compound of formula (I) according to claim 1, wherein A is N.

3. The selenophene compound of formula (I) according to claim 1, wherein:

X is selenium and both Y and Z are carbon;

Y is selenium and both X and Z are carbon; or

Z is selenium and both X and Y are carbon.

4. The selenophene compound of formula (I) according to claim 3, wherein X is selenium and both Y and Z are carbon.

5. The selenophene compound of formula (I) according to claim 3, wherein Y is selenium and both X and Z are carbon.

6. The selenophene compound of formula (I) according to claim 3, wherein Z is selenium and both X and Y are carbon.

7. A selenophene compound of formula (I) according to claim 1, wherein Ar is an optionally substituted benzene ring or an optionally substituted 6-membered aromatic ring containing one, two or three nitrogen atoms;
   wherein said selenophene compound is a compound of formula (VII)

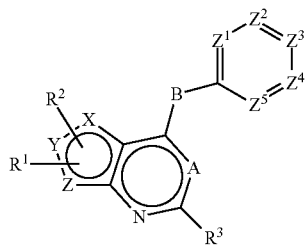

wherein $Z^1$, $Z^2$, $Z^3$, $Z^4$, and $Z^5$ are independently selected from the group consisting of N and C—$R^{11}$, wherein each $R^{11}$ is independently selected from the group consisting of hydrogen, halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$alkenyl, $C_{2-6}$alkynyl, $C_{1-4}$ alkyl carbonyl, $C_{1-4}$ alkoxycarbonyl, aminocarbonyl, $C_{1-6}$ alkylaminocarbonyl, di($C_{1-6}$alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$cycloalkyl, $C_{3-7}$cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, $C_{1-6}$ alkylsulfonyl, optionally substituted phenyl ring, optionally substituted benzyl, and an optionally substituted five membered heteroaromatic ring containing one or more heteroatoms selected from sulfur, oxygen, nitrogen and selenium, with the proviso that no more than one oxygen or sulfur or selenium atom is present in said optionally substituted five membered heteroaromatic ring;
   wherein said phenyl ring, said benzyl, and said 5-membered heteroaromatic ring are optionally substituted by halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$alkenyl, $C_{2-6}$ alkynyl, $C_{1-4}$alkyl carbonyl, $C_{1-4}$alkoxycarbonyl, aminocarbonyl, $C_{1-6}$ alkylaminocarbonyl, di($C_{1-6}$alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$cycloalkyl, $C_{3-7}$ cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino) alkyl, $C_{1-6}$ [di($C_{1-6}$alkyl)amino]alkyl, $C_{1-6}$ alkylsulfinyl, $C_{1-6}$ alkylsulfonyl.

8. A selenophene compound of formula (VII) according to claim 7, wherein each of $Z^1$, $Z^2$, $Z^3$, $Z^4$, and $Z^5$ is C—$R^{11}$.

9. A selenophene compound of formula (VII) according to claim 7, wherein $Z^1$, $Z^2$, $Z^3$, $Z^4$, and $Z^5$ are independently selected from the group consisting of N and C—$R^{11}$, with the proviso that one of $Z^1$, $Z^2$, $Z^3$, $Z^4$, and $Z^5$ is N.

10. A selenophene compound of formula (VII) according to claim 7, wherein $Z^1$, $Z^2$, $Z^3$, $Z^4$, and $Z^5$ are independently selected from the group consisting of N and C—$R^{11}$, with the proviso that $Z^1$ and $Z^2$ are each N; or $Z^2$ and $Z^3$ are each N.

11. A selenophene compound of formula (VII) according to claim 7, wherein $Z^1$, $Z^2$, $Z^3$, $Z^4$, and $Z^5$ are independently selected from the group consisting of N and C—$R^{11}$, with the proviso that $Z^1$ and $Z^3$ are each N; $Z^1$ and $Z^5$ are each N; or $Z^2$ and $Z^4$ are each N.

12. A selenophene compound of formula (VII) according to claim 7, wherein $Z^1$, $Z^2$, $Z^3$, $Z^4$, and $Z^5$ are independently selected from the group consisting of N and C—$R^{11}$, with the proviso that $Z^1$ and $Z^4$ are each N.

13. A selenophene compound of formula (I) according to claim 1, wherein Ar is said optionally substituted 5-membered aromatic ring containing at least one heteroatom selected from the group consisting of sulfur, oxygen, and nitrogen, with the proviso that said 5-membered aromatic ring contains no more than one oxygen or sulfur atom;
   wherein said selenophene compound is a compound of formula (VIII)

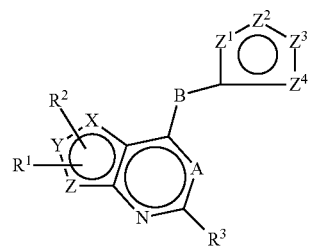

wherein $Z^1$, $Z^2$, $Z^3$, and $Z^4$ are independently selected from the group consisting of S, O, N, NH, and C—$R^{11}$, with the proviso that at least one of $Z^1$, $Z^2$, $Z^3$, and $Z^4$ is not C—$R^{11}$, and no more than one of $Z^1$, $Z^2$, $Z^3$, and $Z^4$ is O or S;
wherein each $R^{11}$ is independently selected from the group consisting of hydrogen, halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$alkenyl, $C_{2-6}$alkynyl, $C_{1-4}$ alkyl carbonyl, $C_{1-4}$ alkoxycarbonyl, aminocarbonyl, $C_{1-6}$ alkylaminocarbonyl, di($C_{1-6}$alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$cycloalkyl, $C_{3-7}$cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, $C_{1-6}$ alkylsulfonyl, optionally substituted phenyl ring, optionally substituted benzyl, and an optionally substituted five membered heteroaromatic ring containing one or more heteroatoms selected from sulfur, oxygen, nitrogen and selenium, with the proviso that no more than one oxygen or sulfur or selenium atom is present in said optionally substituted five membered heteroaromatic ring;
wherein said phenyl ring, said benzyl, and said 5-membered heteroaromatic ring are optionally substituted by halogen, hydroxy, formyl, carboxylic acid, amino, nitro, cyano, sulfonic acid, thiol, trihalomethyl, sulfonamide, $C_{1-6}$ alkyl, $C_{1-6}$ secondary alkyl, $C_{1-6}$ tertiary alkyl, $C_{2-6}$alkenyl, $C_{2-6}$ alkynyl, $C_{1-4}$ alkyl carbonyl, $C_{1-4}$ alkoxycarbonyl, aminocarbonyl, $C_{1-6}$ alkylaminocarbonyl, di($C_{1-6}$alkyl)aminocarbonyl, $C_{1-6}$ haloalkyl, $C_{1-6}$ hydroxyalkyl, $C_{1-6}$ alkoxy, $C_{1-6}$ haloalkoxy, $C_{1-6}$ hydroxyalkoxy, $C_{3-7}$cycloalkyl, $C_{3-7}$ cycloalkoxy, $C_{1-6}$ alkylamino, di($C_{1-6}$ alkyl)amino, $C_{1-6}$ aminoalkyl, $C_{1-6}$ aminoalkoxy, $C_{1-6}$ ($C_{1-6}$ alkylamino)alkyl, $C_{1-6}$ [di($C_{1-6}$alkyl)amino]alkyl, $C_{1-6}$ alkylsulfinyl, or $C_{1-6}$ alkylsulfonyl.

14. A selenophene compound of formula (VIII) according to claim 13, wherein $Z^1$, $Z^2$, $Z^3$, and $Z^4$ are independently selected from the group consisting of S and C—$R^{11}$, with the proviso that one of $Z^1$, $Z^2$, $Z^3$, and $Z^4$ is S.

15. A selenophene compound of formula (VIII) according to claim 13, wherein $Z^1$, $Z^2$, $Z^3$, and $Z^4$ are independently selected from the group consisting of O and C—$R^{11}$, with the proviso that one of $Z^1$, $Z^2$, $Z^3$, and $Z^4$ is O.

16. A selenophene compound of formula (VIII) according to claim 13, wherein $Z^1$, $Z^2$, $Z^3$, and $Z^4$ are independently selected from the group consisting of NH and C—$R^{11}$, with the proviso that one of $Z^1$, $Z^2$, $Z^3$, and $Z^4$ is NH.

17. A selenophene compound of formula (VIII) according to claim 13, wherein $Z^1$, $Z^2$, $Z^3$, and $Z^4$ are independently selected from the group consisting of N, NH and C—$R^{11}$, with the proviso that said optionally substituted 5-membered aromatic ring contains a N—NH bond.

18. A selenophene compound of formula (VIII) according to claim 13, wherein $Z^1$, $Z^2$, $Z^3$, and $Z^4$ are independently selected from the group consisting of N, NH, and C—$R^{11}$, with the proviso that $Z^1$ is N, and either $Z^3$ or $Z^4$ is NH.

19. A selenophene compound of formula (VIII) according to claim 13, wherein $Z^1$, $Z^2$, $Z^3$, and $Z^4$ are independently selected from the group consisting of N, O, and C—$R^{11}$, with the proviso that either $Z^1$ is N, and either $Z^3$ or $Z^4$ is O; or $Z^1$ is O, and either $Z^3$ or $Z^4$ is N.

20. A selenophene compound of formula (VIII) according to claim 13, wherein $Z^1$, $Z^2$, $Z^3$, and $Z^4$ are independently selected from the group consisting of N, O, and C—$R^{11}$, with the proviso that either $Z^1$ is N and $Z^2$ is O; $Z^1$ is O and $Z^2$ is N; or $Z^2$ is N and $Z^3$ is O.

21. A selenophene compound of formula (VIII) according to claim 13, wherein $Z^1$, $Z^2$, $Z^3$, and $Z^4$ are independently selected from the group consisting of N, S, and C—$R^{11}$, with the proviso that either $Z^1$ is N, and either $Z^3$ or $Z^4$ is S; or $Z^1$ is S, and either $Z^3$ or $Z^4$ is N.

22. A selenophene compound of formula (VIII) according to claim 13, wherein $Z^1$, $Z^2$, $Z^3$, and $Z^4$ are independently selected from the group consisting of N, S, and C—$R^{11}$, with the proviso that either Z is N and $Z^2$ is S; or $Z^1$ is S and $Z^2$ is N; or $Z^2$ is N and $Z^3$ is S.

23. A selenophene compound selected from the group consisting of:
 (3-chloro-4-fluorophenyl)-5,6,7,8-tetrahydrobenzo[1,2-b]pyrimidino[5,6-d]selenophen-4-ylamine;
 (5-bromo(3-pyridyl))-5,6,7,8-tetrahydrobenzo[1,2-b]pyrimidino[5,6-d]selenophen-4-ylamine;
 (2,6-dichloropyridin-4-yl)-5,6,7,8-tetrahydrobenzo[1,2-b]pyrimidino[5,6-d]selenophen-4-ylamine;
 (2,6-dichloropyrimidin-4-yl)-5,6,7,8-tetrahydrobenzo[1,2-b]pyrimidino[5,6-d]selenophen-4-ylamine;
 pyrazin-2-yl-5,6,7,8-tetrahydrobenzo[1,2-b]pyrimidino[5,6-d]selenophen-4-ylamine;
 (2,5-dibromo(3-thienyl)-5,6,7,8-tetrahydrobenzo[1,2-b]pyrimidino[5,6-d]selenophen-4-ylamine;
 (5-tert-butyl)-3-(5,6,7,8-tetrahydrobenzo[1,2-b]pyrimidino[5,6-d]selenophen-4-ylamino)thiophene-2-carboxamide;
 5-(tert-butyl)-2-(5,6,7,8-tetrahydrobenzo[1,2-b]pyrimidino[5,6-d]selenophen-4-ylamino)furan-3-carbonitrile;
 5-Phenyl-2-(5,6,7,8-tetrahydrobenzo[1,2-b]pyrimidino[5,6-d]selenophen-4-ylamino)furan-3-carbonitrile;
 2-Methylthio-4-(5,6,7,8-tetrahydrobenzo[1,2-b]pyrimidino[5,6-d]selenophen-4-ylamino)-1,3-thiazole-5-carbonitrile;
 (2-Methylthio-5-nitro(1,3-thiazol-4-yl))-5,6,7,8-tetrahydrobenzo[1,2-b]pyrimidino[5,6-d]selenophen-4-ylamine;
 4-(5,6,7,8-Tetrahydrobenzo[1,2-b]pyrimidino[5,6-d]selenophen-4-ylamino)benzene-sulfonamide;
 [5-(tert-Butyl)selenopheno[3,2-e]pyrimidin-4-yl](3-chloro-4-fluorophenyl)amine;
 (3-Chloro-4-fluorophenyl)(5-phenylselenopheno[3,2-e]pyrimidin-4-yl]amine;
 4-[(3-Chloro-4-fluorophenyl)amino]-5-methylselenophnopheno[2,3-d]pyrimidine-6-carboxylic acid;
 [(3-Chloro-4-fluorophenyl)(6-methyl-5-phenylselenopheno[3,2-e]pyrimidin-4-yl]amine;
 4-[(3-Chloro-4-fluorophenyl)amino]-5-methylselenophnopheno[2,3-d]pyrimidine-6-carboxamide;
 (3-Chloro-4-fluorophenyl)-5,6,7,8-tetrahydropyrimidino[5',6'-5,4]selenopheno[2,3-c]pyridine-4-ylamine;
 4-[(3-Chloro-4-fluorophenyl)amino]-7-(methylsulfonyl)-5,6,7,8-tetrahydro-pyrimidino[5',4'-5,4]selenopheno[2,3-c]pyridine;
 (3-Bromophenyl)-5,6,7,8-tetrahydropyrimidino[5',6'-5,4]selenopheno[2,3-c]pyridine-4-ylamine;
 (3-Ethynylphenyl)-5,6,7,8-tetrahydropyrimidino[5',6'-5,4]selenopheno[2,3-c]pyridine-4-ylamine;
 (3,4-Dichlorophenyl)-5,6,7,8-tetrahydropyrimidino[5',6'-5,4]selenopheno[2,3-c]pyridine-4-ylamine;
 Methyl 5-methyl-4-(5,6,7,8-tetrahydropyrimidino[5',6'-5,4]selenopheno[2,3-c]pyridin-4-ylamino)thiophene-2-carboxylate;
 {4-[3-Chloro-4-fluorophenyl)amino]-5-methylselenopheno[2,3-d]pyrimidin-6-yl}-N-(2-hydroxyethyl)carboxamide;
 N-(2-Chloroethyl) {4-[3-chloro-4-fluorophenyl)amino]-5-methylselenopheno[2,3-d]pyrimidin-6-yl}carboxamide;
 4-[(3-Chloro-4-fluorophenyl)amino]-5,6,8-trihydrobenzo[2,1-b]pyrimidino[5,4-d]selenophen-7-one;
 (3-Chloro-4-fluorophenyl)-6,7,8,9-tetrahydrobenzo[1,2-d]pyrimidino[5,6-b]selenophen-4-ylamine;
 [6-(tert-butyl)selenopheno[2,3-e]pyrimidin-4-yl](3-chloro-4-fluorophenyl)amine;
 (3-Chloro-4-fluorophenyl)(6-phenylselenopheno[2,3-e]pyrimidin-4-yl)amine;
 Benzo[d]pyrimidino[5,6-b]selenophen-4-yl(3-chloro-4-fluorophenyl)amine;
 (3-Chloro-4-fluorophenyl)pyrimidino[4',5'-5,4]selenopheno[2,3-b]pyridin-4-ylamine;
 Ethyl 4-[(3-chloro-4-fluorophenyl)amino]-5-methylthioselenopheno[3,4-d]pyrimidine-7-carboxylate;
 (4-Chlorophenyl)methyl-5,6,7,8-tetrahydropyrimidino[5',6'-5,4]selenopheno[2,3-c]pyridine-4-ylamine; and
 (3-Chloro-4-fluorophenyl)(2-methyl-5,6,7,8-tetrahydrobenzo[1,2-b]pyrimidino[5,6-d]selenophen-4-yl)amine.

24. A process for the preparation of selenophene compound of formula (I) according to claim 1, wherein said process comprises a reaction selected from the group consisting of:
 [A] reacting a compound of formula II with formic acid and sulfuric acid to obtain a compound of formula III; reacting the compound of formula III with a chlorinating agent in the presence of DMF or a base to obtain a compound of formula IV; and reacting the compound of formula IV with an unsubstituted or substituted aromatic amino compound in the presence of a solvent and optionally in the presence of a base to obtain a compound of formula I;

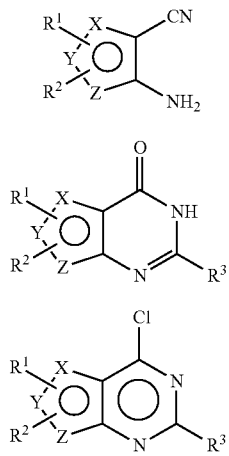

Formula II

Formula III

Formula IV

[B] reacting a compound of formula II with dimethylformamide-dimethylacetal (DMF-DMA) in the presence of a solvent to obtain a compound of formula V; and reacting the compound of formula V with an unsubstituted or substituted aromatic amino compound to obtain a compound of formula I; or

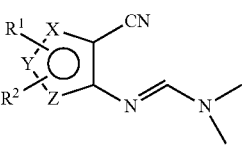

Formula V

[C] reacting a compound of formula II with a trialkyl orthoformate in the presence of a solvent to obtain a compound of formula VI, where $R^{11}$ is alkyl; and reacting the compound of formula VI with an unsubstituted or substituted aromatic amino compound to obtain a compound of formula I wherein X, Y, Z, $R^1$, $R^2$, and $R^3$ are as defined in claim 1.

Formula VI

25. A pharmaceutical composition comprising at least one selenophene compound of formula (I) according to claim 1, a pharmaceutically acceptable salt thereof, a solvate thereof, a hydrate thereof, or a stereoisomer thereof; and
at least one additive selected from the group consisting of pharmaceutically acceptable excipients, pharmaceutically acceptable diluents, and pharmaceutically acceptable carriers.

26. A pharmaceutical composition according to claim 25, wherein said composition further comprises at least one anti-tumor agent selected from the group consisting of Alkylating agents, Anti-metabolites, Hormonal therapy agents, Anti-angiogenic compounds, Antibodies, VEGF inhibitors, EGFR (HER1) inhibitors, HER2 inhibitors, CDK inhibitors, Proteasome inhibitors, Serine/threonine kinase (Raf inhibitors), Tyrosine kinase inhibitors, Androgen receptor antagonists and Aromatase inhibitors.

27. A pharmaceutical composition according to claim 25, wherein additive is selected from the group consisting of glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors, preservatives, distilled water, saline, aqueous glucose solution, alcohol, propylene glycol, polyethylene glycol, various animal and vegetable oils, white soft paraffin, paraffin and wax.

28. A pharmaceutical composition according to claim 26, wherein:
the Alkylating agent is selected from the group consisting of nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, mitolactol, cisplatin, carboplatin, eptaplatin, lobaplatin, nedaplatin, oxaliplatin, satraplatin, and mixtures thereof;
the Anti-metabolite is selected from the group consisting of methotrexate, 6-mercaptopurineriboside, mercaptopurine, 5-fluorouracil, tegafur, doxifluridine, carmofur, cytarabine, cytarabine ocfosfate, enocitabine, gemcitabine, fludarabine, 5-azacitidine, capecitabine, cladribine, clofarabine, decitabine, eflornithine, ethynylcytidine, cytosine arabinoside, hydroxyurea, melphalan, nelarabine, nolatrexed, ocfosfate, disodium pemetrexed, pentostatin, pelitrexol, raltitrexed, triapine, trimetrexate, vidarabine, vincristine, vinorelbine, and mixtures thereof;
the Hormonal therapy agent is selected from the group consisting of exemestane, Lupron, anastrozole, doxercalciferol, fadrozole, formestane, abiraterone acetate, finasteride, epristeride, tamoxifen citrate, fulvestrant, Trelstar, toremifene, raloxifene, lasofoxifene, letrozole, sagopilone, ixabepilone, epothilone B, vinblastine, vinflunine, docetaxel, paclitaxel, and mixtures thereof;
the Anti-angiogenic compound is selected from the group consisting of acitretin, aflibercept, angiostatin, aplidine, asentar, axitinib, recentin, bevacizumab, brivanib alaninate, cilengitide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, vitaxin, and mixtures thereof;
the Antibody is selected from the group consisting of trastuzumab, cetuximab, bevacizumab, rituximab, ticilimumab, ipilimumab, lumiliximab, catumaxomab, atacicept, oregovomab, alemtuzumab, and mixtures thereof;
the VEGF inhibitor is selected from the group consisting of sorafenib, DAST, bevacizumab, sunitinib, recentin, axitinib, aflibercept, telatinib, brivanib alaninate, vatalanib, pazopanib, ranibizumab, and mixtures thereof;

the EGFR (HER1) inhibitor is selected from the group consisting of cetuximab, panitumumab, vectibix, gefitinib, erlotinib, Zactima, and mixtures thereof;

the HER2 inhibitor is selected from the group consisting of lapatinib, tratuzumab, pertuzumab, and mixtures thereof;

the CDK inhibitor is selected from the group consisting of roscovitine, flavopiridol, and mixtures thereof;

the Proteasome inhibitor is selected from the group consisting of bortezomib, carfilzomib, and mixtures thereof;

Serine/threonine kinase (Raf) inhibitor is sorafenib;

the Tyrosine kinase inhibitor is selected from the group consisting of dasatinib, nilotinib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab pertuzumab, and mixtures thereof;

the Androgen receptor antagonist is selected from the group consisting of nandrolone decanoate, fluoxymesterone, Android, Prostaid, andromustine, bicalutamide, flutamide, apo-cyproterone, apoflutamide, chlormadinone acetate, Androcur, Tabi, cyproterone acetate, nilutamide, and mixtures thereof; and the Aromatase inhibitor is selected from the group consisting of anastrozole, letrozole, testolactone, exemestane, aminoglutethimide, formestane, and mixtures thereof.

29. A method for treating or inhibiting or controlling a cell proliferative disorder in a warm blooded animal in need thereof, wherein said method comprises administering to the said warm blooded animal a therapeutically effective amount of at least one selenophene compound of formula (I) according to claim 1, a pharmaceutically acceptable salt thereof, a solvate thereof, a hydrate thereof, or a stereoisomer thereof, wherein said cell proliferative disorder is selected from the group consisting of cancers of the breast, respiratory tract, brain, reproductive organs, digestive tract, urinary tract, eye, liver, skin, head and neck, thyroid, and parathyroid, lymphomas, sarcomas, and leukemias.

30. A method for treating, inhibiting, or controlling a cell proliferative disorder in a warm blooded animal in need thereof, wherein said method comprises administering to the said warm blooded animal a therapeutically effective amount of a pharmaceutical composition according to claim 25, wherein said cell proliferative disorder is selected from the group consisting of cancers of the breast, respiratory tract, brain, reproductive organs, digestive tract, urinary tract, eye, liver, skin, head and neck, thyroid, and parathyroid, lymphomas, sarcomas, and leukemias.

31. A method for treating, inhibiting, or controlling a cell proliferative disorder in a warm blooded animal in need thereof, wherein said method comprises administering to the said warm blooded animal a therapeutically effective amount of a pharmaceutical composition according to claim 26, wherein said cell proliferative disorder is selected from the group consisting of cancers of the breast, respiratory tract, brain, reproductive organs, digestive tract, urinary tract, eye, liver, skin, head and neck, thyroid, and parathyroid, lymphomas, sarcomas and leukemias.

32. A method for treating or inhibiting, or controlling a cell proliferative disorder according to claim 29, wherein said administration comprises the routes selected from the group consisting of intraperitoneal (IP), intravenous (IV), oral (PO), intramuscular (IM), intracutaneous (IC), intradermal (ID), intrauterine, intratumoral and intrarectal.

* * * * *